(12) United States Patent
Jensen et al.

(10) Patent No.: US 8,313,924 B2
(45) Date of Patent: Nov. 20, 2012

(54) MUTEINS OF TEAR LIPOCALIN AND METHODS FOR OBTAINING THE SAME

(75) Inventors: Kristian Jensen, Landshut (DE); Martin Huelsmeyer, Wolfersdorf (DE); Steffen Schlehuber, Ruppertsberg (DE); Andreas Hohlbaum, Paunzhausen (DE); Arne Skerra, Freising (DE); Eric Boudreau, Research Triangle Park, NC (US); Richard Jones, Basel (CH); Ian Kimber, Cheshire (GB); Rebecca Dearman, Cheshire (GB)

(73) Assignee: Pieris AG, Freising-Weihenstephan (DE)

( * ) Notice: Subject to any disclaimer, the term of this patent is extended or adjusted under 35 U.S.C. 154(b) by 391 days.

(21) Appl. No.: 12/309,820

(22) PCT Filed: Aug. 1, 2007

(86) PCT No.: PCT/EP2007/057971
§ 371 (c)(1),
(2), (4) Date: Jun. 11, 2009

(87) PCT Pub. No.: WO2008/015239
PCT Pub. Date: Feb. 7, 2008

(65) Prior Publication Data
US 2009/0305982 A1 Dec. 10, 2009

Related U.S. Application Data

(60) Provisional application No. 60/821,073, filed on Aug. 1, 2006, provisional application No. 60/912,013, filed on Apr. 16, 2007.

(51) Int. Cl.
*C12P 21/02* (2006.01)
*C12N 5/16* (2006.01)
*C07K 14/435* (2006.01)
*A61K 38/17* (2006.01)

(52) U.S. Cl. ............ 435/69.1; 435/320.1; 435/325; 530/350; 536/23.5; 514/21.2

(58) Field of Classification Search .......... None
See application file for complete search history.

(56) References Cited

U.S. PATENT DOCUMENTS

| 7,250,297 B1 | 7/2007 | Beste et al. |
| 7,585,940 B2 * | 9/2009 | Skerra et al. .............. 530/350 |
| 2007/0224633 A1 | 9/2007 | Skerra et al. |

FOREIGN PATENT DOCUMENTS

| EP | 1 270 725 A1 | 1/2003 |
| WO | WO 99/06873 A2 | 2/1999 |
| WO | WO 2005/019256 A2 | 3/2005 |
| WO | WO 2006/056464 A2 | 6/2006 |
| WO | WO 2007/107563 A2 | 9/2007 |

OTHER PUBLICATIONS

Lazar et al Mol. Cell. Biol., vol. 8, pp. 1247-1252, 1988.*
Wells, 1990, Biochemistry 29:8509-8517.*
Breustedt et al, The Journal of Biological Chemistry, 2005, vol. 280, No. 1, pp. 484-493.*
Beste et al., "Small antibody-like proteins with prescribed ligand specificities derived from the lipocalin fold," Proc. Natl. Acad. Sci. USA, Mar. 2, 1999, 96(5):1898-1903.
Gasymov et al., "Site-Directed Tryptophan Fluorescence Reveals the Solution Structure of Tear Lipocalin: Evidence for Features That Confer Promiscuity in Ligand Binding," Biochemistry, Dec. 11, 2001, 40(49):14754-14762.
Schlehuber et al., "Tuning ligand affinity, specificity, and folding stability of an engineered lipocalin variant—a so-called 'anticalin'—using a molecular random approach," Biophysical Chemistry, May 2, 2002, 96(2/03):213-228.
Schlehuber et al., "Anticalins in drug development," Biodrugs, Jan. 1, 2005, 19(5):279-288.
Schlehuber et al., "Anticalins as an alternative to antibody technology," Expert Opinion on Biological Therapy, Jan. 1, 2005, 5(11):1453-1462.
Skerra, Arne, "'Anticalins': a new class of engineering ligand-binding proteins with antibody-like properties," Reviews in Molecular Biotechnology, Jun. 2001, 74(4):257-275.

* cited by examiner

*Primary Examiner* — Bridget E Bunner
*Assistant Examiner* — Fozia Hamud
(74) *Attorney, Agent, or Firm* — Foley & Lardner LLP

(57) ABSTRACT

The present invention relates to novel muteins derived from human tear lipocalin. The invention also refers to a corresponding nucleic acid molecule encoding such a mutein and to a method for its generation. The invention further refers to a method for producing such a mutein. Finally, the invention is directed to a pharmaceutical composition comprising such a lipocalin mutein as well as to various uses of the mutein.

44 Claims, 34 Drawing Sheets

Fig. 1
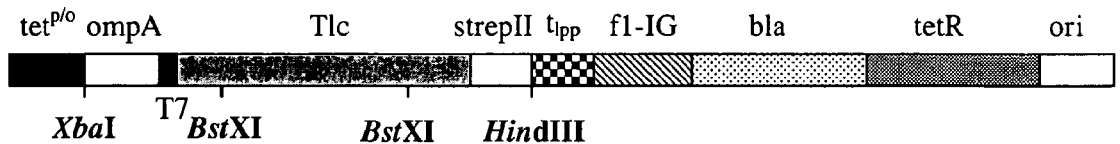
Fig. 2
```
MKKTAIAIAV ALAGFATVAQ ADASMTGGQQ MGASDEEIQD VSGTWYLKAM
TVDSRCPRAY YGSVTPMTLT TLEGGNLEAK VTMQRIGRSQ EVKAVLEKTD
EPGKYTASGG RHVAYIIRSH VKDHYIFYSE GLCPGQPVPG VWLVGRDPKN
NLEALEDFEK AAGARGLSTE SILIPRQSET SSPGSAWSHP QFEK
```
Fig. 3
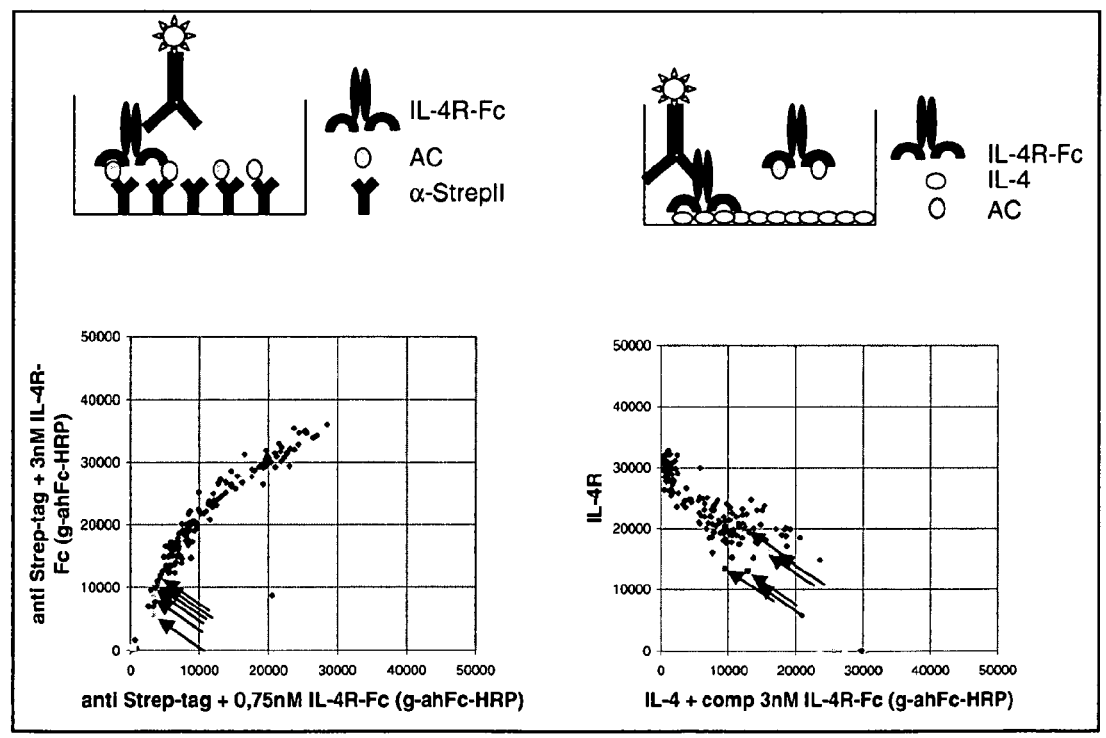

Fig. 4

S191.5 K12:
MKKTAIAIAVALAGFATVAQAASDEEIQDVSGTWYLKAMTVDSRCPRAYYKSVTPMTLTTLEGGNLEAKFTAQ
RNGRWQELKLVLEKTDEPGKYAASGGRHVAYIIRSHVKDHYIFYSEGLCPGQPVPGVWLVGRDPKNNLEALED
FEKAAGARGLSTESILIPRQSETSSPGSAWSHPQFEK

S148.3 J14AM2C2:
MKKTAIAIAVALAGFATVAQAASDEEIQDVSGTWYLKAMTVDSRCPRAYYESVTPMTLTTLEGGNLEAKFTLQ
RRGRWQEGKLVLEKTDEPGKYTASGGRHVAYIIRSHVKDHYIFYSEGLCPGQPVPGVWLVGRDPKNNLEALED
FEKAAGARGLSTESILIPRQSETSSPGSAWSHPQFEK

S191.4 B24:
MKKTAIAIAVALAGFATVAQAASDEEIQDVSGTWYLKAMTVDSRCPRAYYSSVTPMTLTTLEGGNLEAKFTAQ
RSGRWQEYKLVLEKTDEPGKYTASGGRHVAYIIRSHVKDHYIFHSEGLCPGQPVPGVWLVGRDPKNNLEALED
FEKAAGARGLSTESILIPRQSETSSPGSAWSHPQFEK

S191.4 K19:
MKKTAIAIAVALAGFATVAQAASDEEIQDVSGTWYLKAMTVDSRCPRAHYSSVTPMTLTTLEGGNLEAKLTLQ
RAGRWQEGKIVLEKTDEPGKYTASGGRHVAYIIRSHVKDHYIFYSEGLCPGQPVPGVWLVGRDPKNNLEALED
FEKAAGARGLSTESILIPRQSETSSPGSAWSHPQFEK

S191.5 H16:
MKKTAIAIAVALAGFATVAQAASDEEIQDVSGTWYLKAMTVDSRCPRAYYDSVTPMTLTTLEGGNLEAKGTLQ
RKGRPQEMKLVLEKTDEPGKYTASGGRHVAYIIRSHVKDHYIFYSEGLCPGQPVPGVWLVGRDPKNNLEALED
FEKAAGARGLSTESILIPRQSETSSPGSAWSHPQFEK

S197.8 D22:
MKKTAIAIAVALAGFATVAQAASDEEIQDVSGTWYLKAMTVDSRCPRAYYGSVTPMTLTTLEGGNLEAKLTLQ
RSGRWQESKVVLEKTDEPGKYTASGGRHVAYIIRSHVKDHYIFYSEGLCPGQPVPGVWLVGRDPKNNLEALED
FEKAAGARGLSTESILIPRQSETSSPGSAWSHPQFEK

Fig. 19
a)
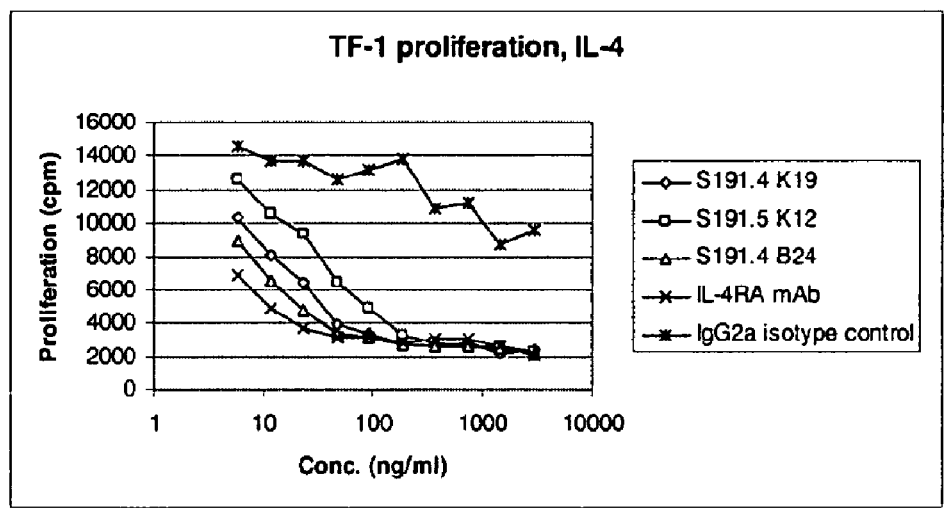
b)
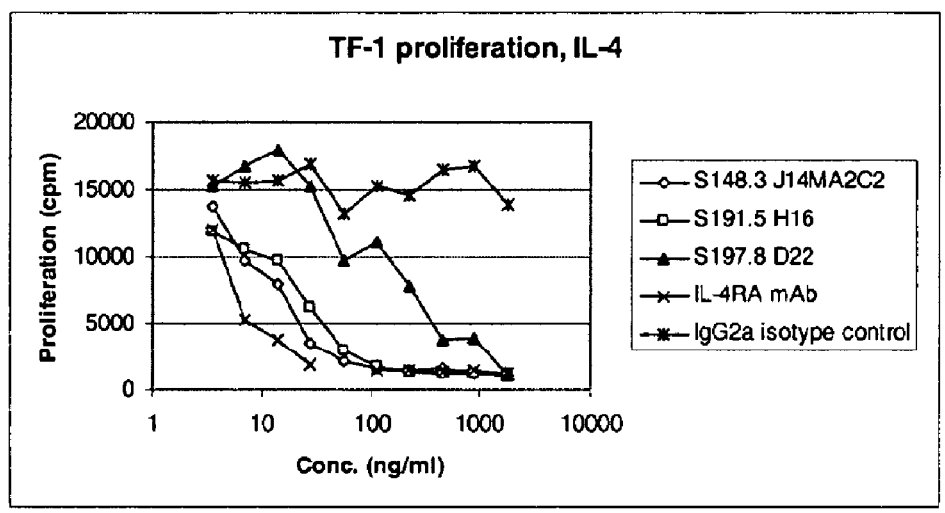

Fig. 19
c)
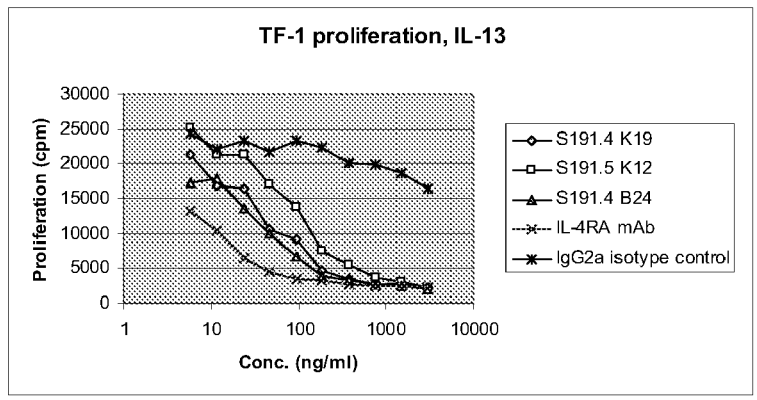
d)
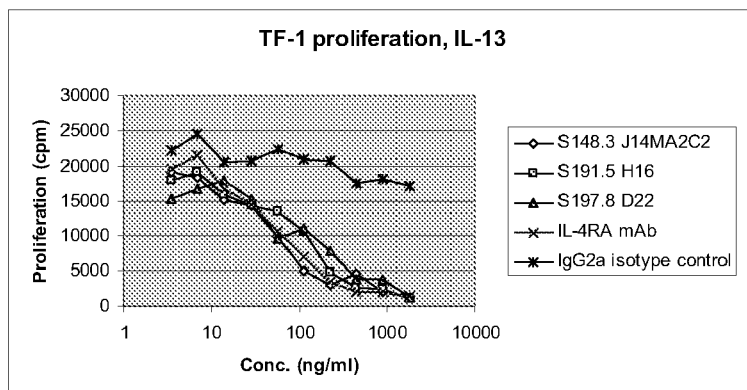
Fig. 20
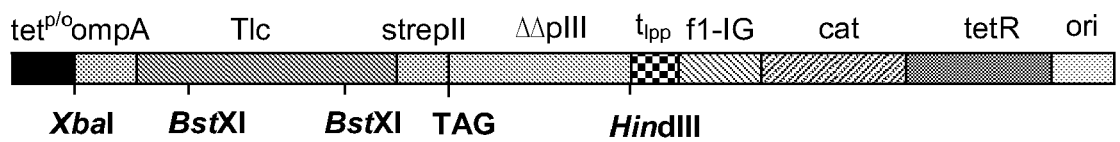

Fig. 21
Fig. 21a)
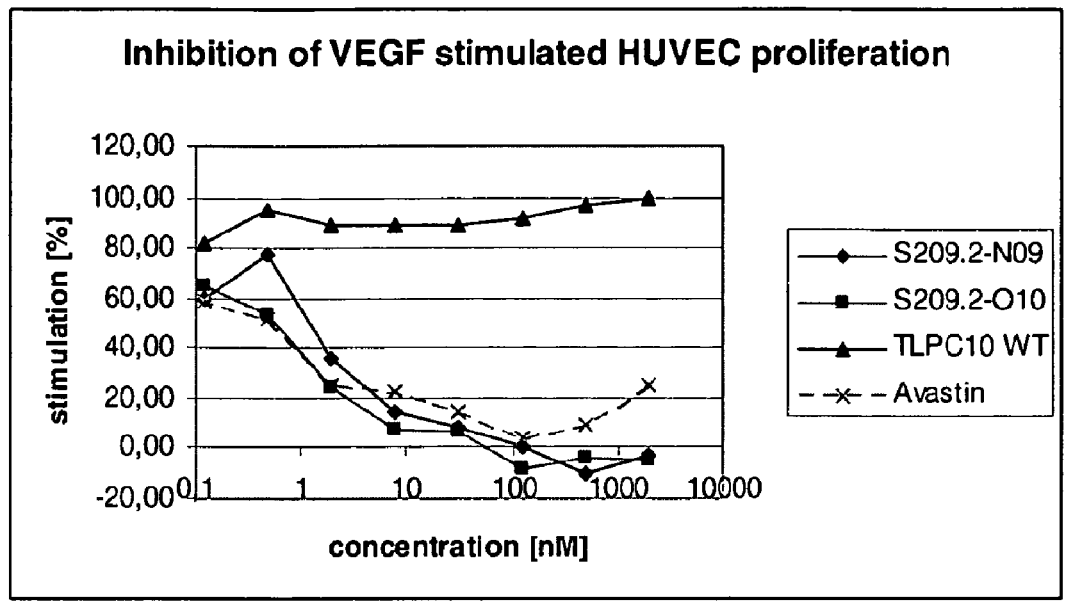
Fig. 21b)
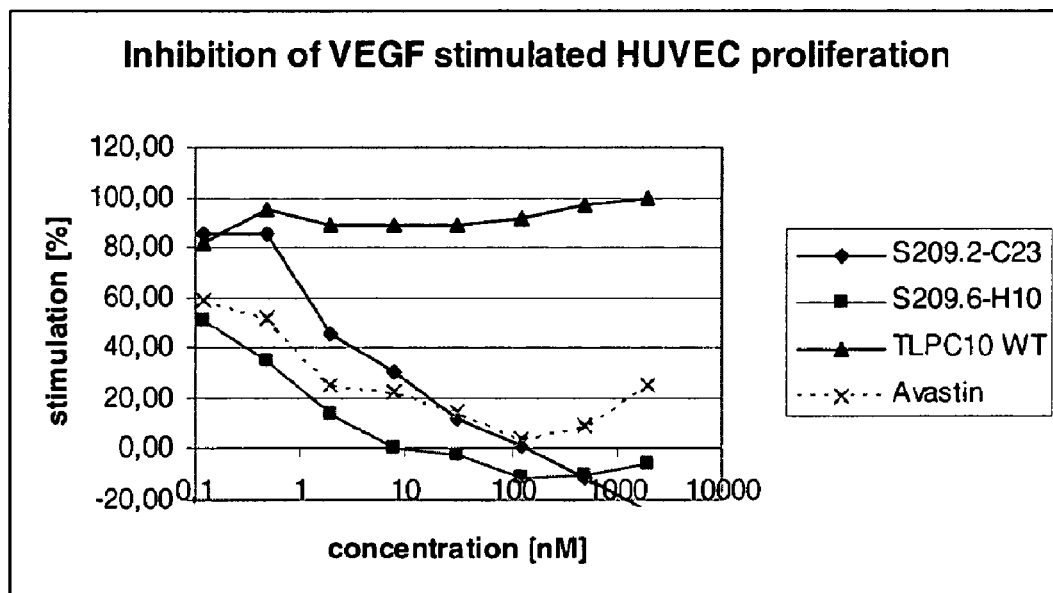

Fig. 25
a)
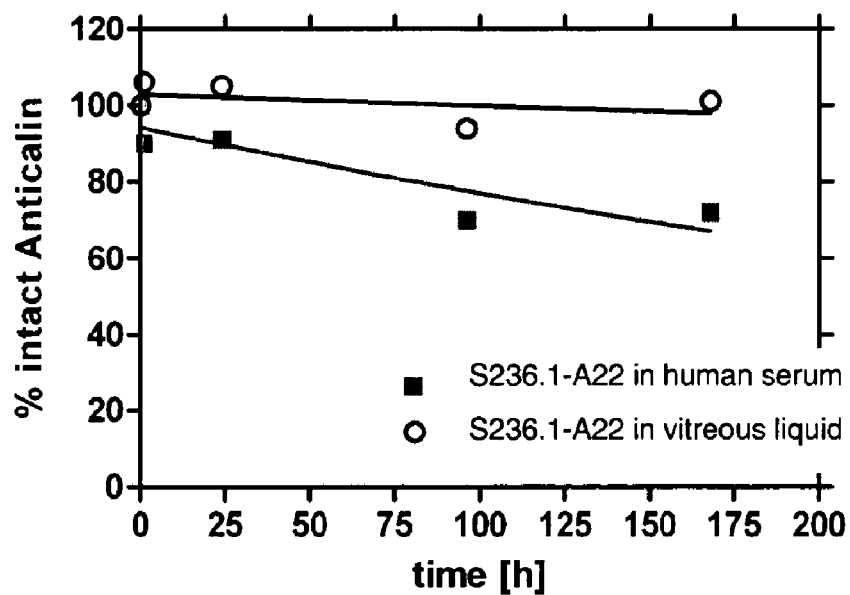
b)
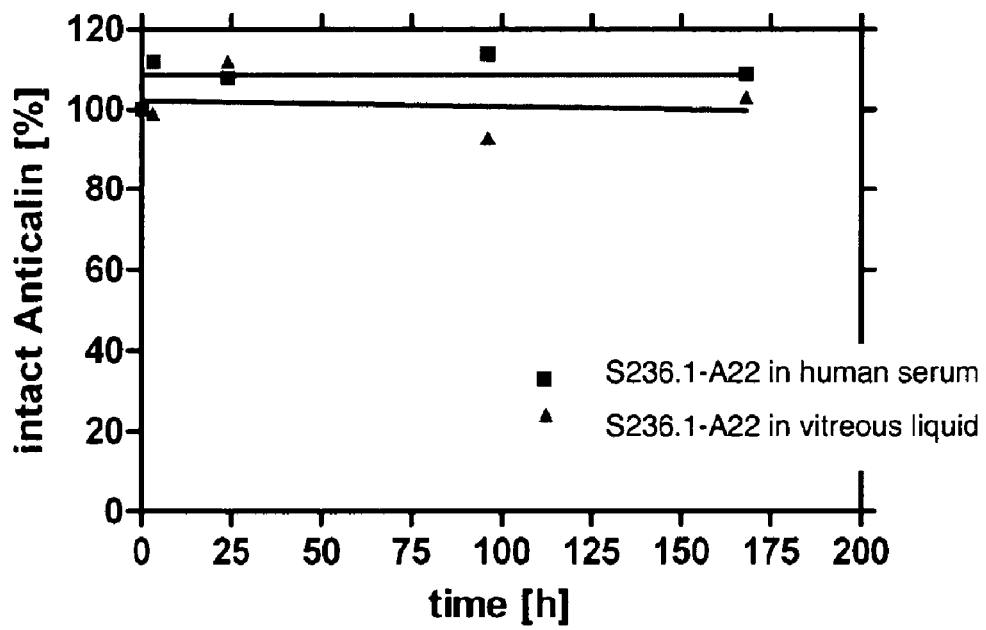

Biacore-measurements

S236.1-A22 (tear lipocalin mutein)           KD: 200pM

S236.1-A22-ABD (tear lipocalin mutein-ABD)   KD: 260pM

| Compound | IC50 [nM] |
|---|---|
| S236.1-A22 (lipocalin mutein) | 0.51 |
| Avastin | 0.56 |

| Compound | IC50 [nM] |
|---|---|
| S236.1-A22 (lipocalin mutein) | 4.5 |
| Avastin | 13 |

MUTEINS OF TEAR LIPOCALIN AND METHODS FOR OBTAINING THE SAME

CROSS-REFERENCE TO RELATED APPLICATIONS

This application is a National Stage application of PCT/EP2007/057971, filed Aug. 1, 2007, which claims priority from U.S. Provisional Applications 60/821,073, filed Aug. 1, 2006, and 60/912,013, filed Apr. 16, 2007.

The instant application contains a Sequence Listing which has been submitted in ANSI format via EFS-WEB and is hereby incorporated by reference in its entirety. Said ANSI copy, created on Jan. 23, 2012 is named sequence.txt and is 103 KB.

BACKGROUND OF THE INVENTION

1. Field of the Invention

The present invention relates to novel muteins derived from human tear lipocalin that bind a given non-natural ligand with detectable affinity. The invention also relates to corresponding nucleic acid molecules encoding such a mutein and to a method for their generation. The invention further relates a method for producing such a mutein. Finally, the invention is directed to a pharmaceutical composition comprising such a lipocalin mutein as well as to various uses of the mutein.

2. Description of Related Art

The members of the lipocalin protein family (Pervaiz, S., and Brew, K. (1987) *FASEB J.* 1, 209-214) are typically small, secreted proteins which are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homeostasis (reviewed, for example, in Flower, D. R. (1996) *Biochem. J.* 318, 1-14 and Flower, D. R. et al. (2000)*Biochim. Biophys. Acta* 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. One end of the barrel is sterically blocked by the N-terminal peptide segment that runs across its bottom as well as three peptide loops connecting the β-strands. The other end of the β-barrel is open to the solvent and encompasses a target-binding site, which is formed by four peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), *supra*; Flower, D. R. et al. (2000), *supra*, or Skerra, A. (2000) *Biochim. Biophys. Acta* 1482, 337-350).

Human tear pre-albumin, now called tear lipocalin (TLPC or Tlc), was originally described as a major protein of human tear fluid (approximately one third of the total protein content) but has recently also been identified in several other secretory tissues including prostate, nasal mucosa and tracheal mucosa. Homologous proteins have been found in rat, pig, dog and horse. Tear lipocalin is an unusual lipocalin member because of its high promiscuity for relative insoluble lipids and binding characteristics that differ from other members of this protein family (reviewed in Redl, B. (2000) *Biochim. Biophys. Acta* 1482, 241-248). A remarkable number of lipophilic compounds of different chemical classes such as fatty acids, fatty alcohols, phospholipids, glycolipids and cholesterol are endogenous ligands of this protein. Interestingly, in contrast to other lipocalins the strength of ligand (target) binding correlates with the length of the hydrocarbon tail both for alkyl amides and fatty acids. Thus, tear lipocalin binds most strongly the least soluble lipids (Glasgow, B. J. et al. (1995) *Curr. Eye Res.* 14, 363-372; Gasymov, O. K. et al. (1999) *Biochim. Biophys. Acta* 1433, 307-320).

The precise biological function of human tear lipocalin has not been fully elucidated so far and is still a matter of controversy. In tear fluid, it appears to be most important for the integrity of the tear film by removing lipids from the mucous surface of the eye to the liquid phase (reviewed in Gasymov, O. K. et al. (1999), *supra*). However, it displays additional activities in vitro that are very unusual among lipocalins, namely inhibition of cysteine proteinases as well as non-specific endonuclease activity (van't H of, W. et al. (1997) *J. Biol. Chem.* 272, 1837-1841; Yusifov, T. N. et al. (2000) *Biochem. J.* 347, 815-819). Recently, it has been demonstrated that tear lipocalin is able to bind several lipid peroxidation products in vitro resulting in the hypothesis that it might function as a physiological oxidative-stress-induced scavenger of potentially harmful lipophilic molecules (Lechner, M. et al. (2001) *Biochem. J.* 356, 129-135).

Proteins, which selectively bind to their corresponding targets by way of non-covalent interaction, play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used. The application of other proteins with defined ligand-binding characteristics, for example the lectins, has remained restricted to special cases.

Rather recently, members of the lipocalin family have become subject of research concerning proteins having defined ligand-binding properties. The PCT publication WO 99/16873 discloses polypeptides of the lipocalin family with mutated amino acid positions in the region of the four peptide loops, which are arranged at the end of the cylindrical β-barrel structure encompassing the binding pocket, and which correspond to those segments in the linear polypeptide sequence comprising the amino acid positions 28 to 45, 58 to 69, 86 to 99, and 114 to 129 of the bilin-binding protein of *Pieris brassicae*.

The PCT publication WO 00/75308 discloses muteins of the bilin-binding protein, which specifically bind digoxigenin, whereas the International Patent Applications WO 03/029463 and WO 03/029471 relate to muteins of the human neutrophil gelatinase-associated lipocalin (hNGAL) and apo-lipoprotein D, respectively. In order to further improve and fine tune ligand affinity, specificity as well as folding stability of a lipocalin variant various approaches using different members of the lipocalin family have been proposed (Skerra, A. (2001) *Rev. Mol. Biotechnol.* 74, 257-275; Schlehuber, S., and Skerra, A. (2002) *Biophys. Chem.* 96, 213-228), such as the replacement of additional amino acid residues. The PCT publication WO 2006/56464 discloses muteins of human neutrophile gelatinase-associated lipocalin with binding affinity for CTLA-4 in the low nanomolar range.

The PCT publication WO 2005/19256 discloses muteins of tear lipocalin with at least one binding site for different or the same target ligand and provides a method for the generation of such muteins of human tear lipocalin. According to this PCT application, certain amino acid stretches within the primary sequence of tear lipocalin, in particular the loop regions comprising amino acids 7-14, 24-36, 41-49, 53-66, 69-77, 79-84, 87-98, and 103-110 of mature human tear lipocalin, are subjected to mutagenesis in order to generate muteins with binding affinities. The resulting muteins have binding affinities for the selected ligand ($K_D$) in the nanomolar range, in most cases >100 nM.

BRIEF SUMMARY OF THE INVENTION

Despite this progress it would be still desirable to have a method for the generation of human tear lipocalin muteins that possess improved binding properties for a selected target molecule, for example in the picomolar range, simply for the reason to further improve the suitability of muteins of human tear lipocalin in diagnostic and therapeutic applications.

Accordingly, it is an object of the invention to provide human tear lipocalin muteins having high binding affinity for a given target.

DETAILED DESCRIPTION OF THE INVENTION

This object is accomplished by a method for the generation of a human tear lipocalin mutein having the features of the independent claims.

In a first aspect, the present invention provides a method for the generation of a mutein of human tear lipocalin, wherein the mutein binds a given non-natural ligand of human tear lipocalin with detectable binding affinity, including:
  (a) subjecting a nucleic acid molecule encoding a human tear lipocalin to mutagenesis at at least one codon of any of the amino acid sequence positions 26-34, 56-58, 80, 83, 104-106 and 108 of the linear polypeptide sequence of native mature human tear lipocalin, wherein at least one of the codons encoding cysteine residues at sequence positions 61 and 153 of the linear polypeptide sequence of the mature human tear lipocalin has been mutated to encode any other amino acid residue, thereby obtaining a plurality of nucleic acids encoding muteins of human tear lipocalin,
  (b) expressing the one or more mutein nucleic acid molecule(s) obtained in (a) in an expression system, thereby obtaining one or more mutein(s), and
  (c) enriching the one or more mutein(s) obtained in step (b) and having detectable binding affinity for a given non-natural ligand of human tear lipocalin by means of selection and/or isolation.

In this context it is noted that the inventors have surprisingly found that removal of the structural disulfide bond (on the level of a respective naïve nucleic acid library) of wild type tear lipocalin that is formed by the cystein residues 61 and 153 (cf. Breustedt, et al. (2005), The 1.8-Å crystal structure of human tear lipocalin reveals an extended branched cavity with capacity for multiple ligands. *J. Biol. Chem.* 280, 484-493) provides tear lipocalin muteins that are not only stably folded but in addition are also able to bind a given non-natural ligand with affinity in the low picomolar range. Without wishing to be bound by theory, it is also believed that the elimination of the structural disulde bond provides the further advantage of allowing for the (spontaneous) generation or deliberate introduction of non-natural artificial disulfide bonds into muteins of the invention (see Examples), thereby increasing the stability of the muteins, for example.

The term "mutagenesis" as used herein means that the experimental conditions are chosen such that the amino acid naturally occurring at a given sequence position of human tear lipocalin (Swiss-Prot data bank entry P31025) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

The coding sequence of human tear lipocalin (Redl, B. et al. (1992) *J. Biol. Chem.* 267, 20282-20287) is used as a starting point for the mutagenesis of the peptide segments selected in the present invention. For the mutagenesis of the recited amino acid positions, the person skilled in the art has at his disposal the various established standard methods for site-directed mutagenesis (Sambrook, J. et al. (1989), *supra*). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cyto sine or thymine; K=guanine or thymine; S=adenine or cyto sine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-β-D-ribofuranosyl)-3,4-dihydro-8H-pyrimindo-1,2-oxazine-7-one (Zaccolo et al. (1996) *J. Mol. Biol.* 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, Ge L, Plückthun A, Schneider K C, Wellnhofer G, Moroney S E. 1994 Trinucleotide phosphoramidites: ideal reagents for the synthesis of mixed oligonucleotides for random mutagenesis. *Nucleic Acids Res* 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid comprising the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (1989), *supra*). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

The term "human tear lipocalin" as used herein to refer to the mature human tear lipocalin with the SWISS-PROT Data Bank Accession Number P31025.

The term "non-natural ligand" refers to a compound, which does not bind to native mature human tear lipocalin under physiological conditions. The target (ligand) may be any chemical compound in free or conjugated form which exhibits features of an immunological hapten, a hormone such as steroid hormones or any biopolymer or fragment thereof, for example, a protein or protein domain, a peptide, an oligodeoxynucleotide, a nucleic acid, an oligo- or polysaccharide or conjugates thereof, a lipid or another macromolecule.

In one embodiment of the invention, the method for the generation of a mutein of human tear lipocalin includes mutating at least 2, 3, 4, 5, 6, 8, 10, 12, 14, 15, 16, or 17 of the codons of any of the amino acid sequence positions 26-34, 56-58, 80, 83, 104-106, and 108 of the linear polypeptide sequence of mature human tear lipocalin. In another embodiment all 18 of the codons of amino acid sequence positions 26, 27, 28, 29, 30, 31, 32, 33, 34, 56, 57, 58, 80, 83, 104, 105, 106, and 108 of the linear polypeptide sequence of mature human tear lipocalin are mutated.

In another aspect, the present invention includes a method for the generation of a mutein of human tear lipocalin, wherein the mutein binds a given non-natural ligand of human tear lipocalin with detectable binding affinity, including:
  (a) subjecting a nucleic acid molecule encoding a human tear lipocalin to mutagenesis at at least one codon of any of the amino acid sequence positions 34, 80, and 104 of the linear polypeptide sequence of mature human tear lipocalin, thereby obtaining a plurality of nucleic acids encoding muteins of human tear lipocalin,
  (b) expressing the one or more mutein nucleic acid molecule(s) obtained in (a) in an expression system, thereby obtaining one or more mutein(s), and
  (c) enriching the one or more mutein(s) obtained in step (b) and having detectable binding affinity for a given non-natural ligand of human tear lipocalin by means of selection and/or isolation.

In one embodiment of the afore-mentioned method, additionally at least 2, 3, 4, 5, 6, 8, 10, 12, 14, or 15 of the codons of any of the amino acid sequence positions 26-33, 56-58, 83, 105-106, and 108 of the linear polypeptide sequence of mature human tear lipocalin are mutated.

In a further embodiment of the invention, the methods according to the invention include the mutation of both of the codons encoding cysteine at positions 61 and 153 in the linear polypeptide sequence of mature human tear lipocalin. In one embodiment position 61 is mutated to encode an alanine, phenylalanine, lysine, arginine, threonin, asparagine, tyrosine, methionine, serine, proline or a tryptophane residue, to name only a few possibilities. In embodiments where position 153 is mutated, an amino acid such as a serine or alanine can be introduced at position 153.

In another embodiment of the invention as described herein, the codons encoding amino acid sequence positions 111 and/or 114 of the linear polypeptide sequence of mature human tear lipocalin are mutated to encode for example an arginine at position 111 and a tryptophane at position 114.

Another embodiment of the methods of the invention, involves mutagenesis of the codon encoding the cysteine at position 101 of the linear polypeptide sequence of mature human tear lipocalin so that this codon encodes any other amino acid. In one embodiment the mutated codon encoding position 101 encodes a serine. Accordingly, in some embodiments either two or all three of the cystein codons at position 61, 101 and 153 are replaced by a codon of another amino acid.

According to the method of the invention a mutein is obtained starting from a nucleic acid encoding human tear lipocalin. Such a nucleic acid is subjected to mutagenesis and introduced into a suitable bacterial or eukaryotic host organism by means of recombinant DNA technology. Obtaining a nucleic acid library of tear lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in its entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) *supra*; Lowman, H. B. (1997) *supra* or Rodi, D. J., and Makowski, L. (1999) *supra*), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

In accordance with this disclosure, step (c) further comprises in another embodiment of the above methods:
(i) providing as a given ligand a compound selected from the group consisting of a chemical compound in free or conjugated form that exhibits features of an immunological hapten, a peptide, a protein or another macromolecule such as a polysaccharide, a nucleic acid molecule (DNA or RNA, for example) or an entire virus particle or viroid, for example,
(ii) contacting the plurality of muteins with said ligand in order to allow formation of complexes between said ligand and muteins having binding affinity for said ligand, and
(iii) removing muteins having no or no substantial binding affinity.

In some embodiments of the invention, the ligand may be a protein or a fragment thereof. In one of these embodiments muteins binding the human T-cell coreceptor CD4 are excluded.

In one embodiment of the methods of the invention, the selection in step (c) is carried out under competitive conditions. Competitive conditions as used herein means that selection of muteins encompasses at least one step in which the muteins and the given non-natural ligand of human tear lipocalin (target) are brought in contact in the presence of an additional ligand, which competes with binding of the muteins to the target. This additional ligand may be a physiological ligand of the target, an excess of the target itself or any other non-physiological ligand of the target that binds at least an overlapping epitope to the epitope recognized by the muteins of the invention and thus interferes with target binding of the muteins. Alternatively, the additional ligand competes with binding of the muteins by complexing an epitope distinct from the binding site of the muteins to the target by allosteric effects.

An embodiment of the phage display technique (reviewed in Kay, B. K. et al. (1996), *supra*; Lowman, H. B. (1997) *supra* or Rodi, D. J., and Makowski, L. (1999), *supra*) using temperent M13 phage is given as an example of a selection method that can be employed in the present invention. Another embodiment of the phage display technology that can be used for selection of muteins of the invention is the hyperphage phage technology as described by Broders et al. (Broders et al. (2003) "Hyperphage. Improving antibody presentation in phage display." *Methods Mol. Biol.* 205:295-302). Other temperent phage such as f1 or lytic phage such as T7 may be employed as well. For the exemplary selection method, M13 phagemids are produced which allow the expression of the mutated lipocalin nucleic acid sequence as a fusion protein with a signal sequence at the N-terminus, preferably the OmpA-signal sequence, and with the capsid protein pIII of the phage M13 or fragments thereof capable of being incorporated into the phage capsid at the C-terminus. The C-terminal fragment ΔpIII of the phage capsid protein comprising amino acids 217 to 406 of the wild type sequence is preferably used to produce the fusion proteins. Especially preferred in one embodiment is a C-terminal fragment of pIII, in which the cysteine residue at position 201 is missing or is replaced by another amino acid.

Accordingly, a further embodiment of the methods of the invention involves operably fusing a nucleic acid coding for the plurality of muteins of human tear lipocalin and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may comprise additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasmid vector pTLPC27, now also called pTlc27 that is described here can be used for the preparation of a phagemid library encoding human tear lipocalin muteins. The inventive nucleic acid molecules coding for the tear lipocalin muteins are inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

The resulting library is subsequently superinfected in liquid culture with an appropriate M13-helper phage or hyperphage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the lipocalin muteins on their surface as a fusion with the infective coat protein pIII but no native capsid protein. During or after infection with helper phage or hyperphage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. In case of hyperphage display induction conditions result in a population of hyperphagemids carrying between three and five fusion proteins consisting of the lipocalin mutein and the capsid protein pIII. Various methods are known for isolating the phagemids, such as precipitation with polyethylene glycol. Isolation typically occurs after an incubation period of 6-8 hours.

The isolated phasmids can then be subjected to selection by incubation with the desired target, wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immuno-sticks" can preferably be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. A preferred method is the elution using buffers of pH 2.2, wherein the eluate is subsequently neutralized. Alternatively, a solution of the free target can be added in order to compete with the immobilized target for binding to the phagemids or target-specific phagemids can be eluted by competition with immunoglobulins or natural liganding proteins which specifically bind to the target of interest.

Afterwards, E. coli cells are infected with the eluted phagemids. Alternatively, the nucleic acids can be extracted from the eluted phagemids and used for sequence analysis, amplification or transformation of cells in another manner. Starting from the E. coli clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the muteins of the invention in sufficiently enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an E. coli strain is infected with the phagemids obtained from the selection cycles and the corresponding double stranded phasmid DNA is isolated. Starting from this phasmid DNA, or also from the single-stranded DNA extracted from the phagemids, the nucleic acid sequences of the selected muteins of the invention can be determined by the methods known in the art and the amino acid sequence can be deduced therefrom. The mutated region or the sequence of the entire tear lipocalin mutein can be subcloned on another expression vector and expressed in a suitable host organism. For example, the vector pTLPC26 now also called pTlc26 can be used for expression in E. coli strains such as E. coli TG1. The muteins of tear lipocalin thus produced can be purified by various biochemical methods. The tear lipocalin muteins produced, for example with pTlc26, carry the affinity peptide Strep-tag II (Schmidt et al., supra) at their C-termini and can therefore preferably be purified by streptavidin affinity chromatography.

The selection can also be carried out by means of other methods. Many corresponding embodiments are known to the person skilled in the art or are described in the literature. Moreover, a combination of methods can be applied. For example, clones selected or at least enriched by "phage display" can additionally be subjected to "colony screening". This procedure has the advantage that individual clones can directly be isolated with respect to the production of a tear lipocalin mutein with detectable binding affinity for a target.

In addition to the use of E. coli as host organism in the "phage display" technique or the "colony screening" method, other bacterial strains, yeast or also insect cells or mammalian cells can be used for this purpose. Further to the selection of a tear lipocalin mutein from a random library as described above, evolutive methods including limited mutagenesis can also be applied in order to optimize a mutein that already possesses some binding activity for the target with respect to affinity or specificity for the target after repeated screening cycles.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) J. Mol. Biol. 255, 589-603. Other methods of random mutagenesis that are suitable for such purposes include random insertion/deletion (RID) mutagenesis as described by Murakami, H et al. (2002) Nat. Biotechnol. 20, 76-81 or nonhomologous random recombination (NRR) as described by Bittker, J. A et al. (2002) Nat. Biotechnol. 20, 1024-1029. If desired, affinity maturation can also be carried out according to the procedure described in WO 00/75308 or Schlehuber, S. et al., (2000) J. Mol. Biol.

297, 1105-1120, where muteins of the bilin-binding protein having high affinity to digoxigenin were obtained.

In a further aspect, the present invention is directed to a mutein of human tear lipocalin having detectable binding affinity to a given non-natural ligand of human tear lipocalin, which is obtainable by or obtained by the above-detailed methods of the invention.

In one embodiment, the mutein of human tear lipocalin obtained according to the above methods includes the substitution of at least one or of both of the cysteine residues occurring at each of the sequences positions 61 and 153 by another amino acid and the mutation of at least one amino acid residue at any one of the sequence positions 26-34, 56-58, 80, 83, 104-106, and 108 of the linear polypeptide sequence of mature human tear lipocalin. The positions 24-36 are comprised in the AB loop, the positions 53-66 are comprised in the CD loop, the positions 69-77 are comprised in the EF loop and the positions 103-110 are comprised in the GH loop in the binding site at the open end of the β-barrel structure of tear lipocalin. The definition of these four loops is used herein in accordance with Flower (Flower, D. R. (1996), supra and Flower, D. R. et al. (2000), supra). Usually, such a mutein comprises at least 2, 3, 4, 5, 6, 8, 10, 12, 14, 15, 16, 17 or 18 mutated amino acid residues at the sequence positions 26-34, 56-58, 80, 83, 104-106, and 108 of the linear polypeptide sequence of mature human tear lipocalin. In a specific embodiment, the mutein comprises the amino acid substitutions Cys 61→Ala, Phe, Lys, Arg, Thr, Asn, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein.

In still another embodiment, the mutein comprises at least one additional amino acid substitution selected from Arg 111→Pro and Lys 114→Trp. A mutein of the invention may further comprise the cysteine at position 101 of the sequence of native mature human tear lipocalin substituted by another amino acid. This substitution may, for example, be the mutation Cys 101→Ser or Cys 101→Thr.

The non-natural ligand the mutein is binding to may be protein or a fragment thereof with the proviso that in some embodiments the human T-cell coreceptor CD4 may be excluded as non natural target.

The lipocalin muteins of the invention may comprise the wild type (natural) amino acid sequence outside the mutated amino acid sequence positions. On the other hand, the lipocalin muteins disclosed herein may also contain amino acid mutations outside the sequence positions subjected to mutagenesis as long as those mutations do not interfere with the binding activity and the folding of the mutein. Such mutations can be accomplished very easily on DNA level using established standard methods (Sambrook, J. et al. (1989) Molecular Cloning: A Laboratory Manual, 2nd Ed., Cold Spring Harbor Laboratory Press, Cold Spring Harbor, N.Y.). Possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein (see for example, the experimental section in which muteins with truncated N- and C-terminus are generated).

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. However, it is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. Exemplary possibilities of such a mutation to introduce a cysteine residue into the amino acid sequence of a human tear lipocalin mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective tear lipocalin mutein. The mutein S236.1-A22 into which a cysteine is introduced at any these sequence positions (see Example 46) is an illustrative example of such muteins of the invention.

The present invention also encompasses muteins as defined above, in which the first four N-terminal amino acid residues of the sequence of mature human tear lipocalin (His-His-Leu-Leu; positions 1-4) and/or the last two C-terminal amino acid residues (Ser-Asp; positions 157-158) of the sequence of mature human tear lipocalin have been deleted (cf. also the Examples and the attached Sequence Listings).

The lipocalin muteins of the invention are able to bind the desired target with detectable affinity, i.e. with a dissociation constant of at least 200 nM. Presently preferred in some embodiments are lipocalin muteins, which bind the desired target with a dissociation constant for a given target of at least 100, 20, 1 nM or even less. The binding affinity of a mutein to the desired target can be measured by a multitude of methods such as fluorescence titration, competition ELISA or surface plasmon resonance (BIAcore).

It is readily apparent to the skilled person that complex formation is dependent on many factors such as concentration of the binding partners, the presence of competitors, ionic strength of the buffer system etc. Selection and enrichment is generally performed under conditions allowing the isolation of lipocalin muteins having, in complex with the desired target, a dissociation constant of at least 200 nM. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate. Alternatively, selection can be performed under conditions, which favour fast formation of the complex between the mutein and the target, or in other words a high $k_{on}$ rate. As a further illustrative alternative, the screening can be performed under conditions that select for improved thermostability of the muteins (compared to either wild type tear lipocalin or a mutein that already has affinity towards a pre-selected target)

A tear lipocalin mutein of the invention typically exists as monomeric protein. However, it is also possible that an inventive lipocalin mutein is able to spontaneously dimerise or oligomerise. Although the use of lipocalin muteins that form stable monomers may be preferred for some applications, e.g. because of faster diffusion and better tissue penetration, the use of lipocalin muteins that spontaneously form stable homodimers or multimers may be advantageous in other instances, since such multimers can provide for a (further) increased affinity and/or avidity to a given target. Furthermore, oligomeric forms of the lipocalin mutein may have slower dissociation rates or prolonged serum half-life. If dimerisation or multimerisation of muteins that form stable monomers is desired, this can for example be achieved by fusing respective oligomerization domains such as jun-fos domains or leucin-zippers to muteins of the invention or by the use of "Duocalins" (see also below).

A tear lipocalin mutein of the invention may be used for complex formation with a given target. The target may be a non-natural target/ligand. The target (ligand) may be any chemical compound in free or conjugated form which exhibits features of an immunological hapten, a hormone such as steroid hormones or any biopolymer or fragment thereof, for example, a protein or protein domain, a peptide, an oligodeoxynucleotide, a nucleic acid, an oligo- or polysaccharide or conjugates thereof. In one embodiment of the invention the target is a protein with the proviso that the human T-cell coreceptor CD4 is excluded. The protein can be any globular soluble protein or a receptor protein, for example, a transmembrane protein involved in cell signaling, a component of the immune systems such as an MHC molecule or cell surface receptor that is indicative of a specific disease. The mutein may also be able to bind only fragments of a protein. For example, a mutein can bind to a domain of a cell surface receptor, when it is part of the receptor anchored in the cell membrane as well as to the same domain in solution, if this domain can be produced as a soluble protein as well. However the invention is by no means limited to muteins that only bind such macromolecular targets. But it is also possible to obtain muteins of tear lipocalin by means of mutagenesis which show specific binding affinity to ligands of low(er) molecular weight such as biotin, fluorescein or digoxigenin.

In one embodiment of the invention the ligand that is bound by the tear lipocalin mutein is a protein or fragment thereof selected from the group of vascular endothelial growth factor (VEGF), vascular endothelial growth factor receptor 2 (VEGF-R2), and interleukin 4 receptor alpha chain (IL-4 receptor alpha) or fragments thereof. Also included as ligands are an extracellular region or a domain of VEGF-R2 or IL-4 receptor alpha. These ligands are typically of mammalian origin. In one embodiment these ligands are of human origin, but they may also be of mouse, rat, porcine, equine, canine, feline or bovine or cynomolgus origin, to name only a few illustrative examples.

Human VEGF may be selected from the group consisting of VEGF-A, VEGF-B, VEGF-C, and VEGF-D and may have the amino acid sequences set forth in SWISS PROT Data Bank Accession Nos. P15692, P49765, P49767, and 043915 (SEQ ID Nos.: 22-25) or of fragments thereof. One such exemplary fragment consists of amino acids 8 to 109 of VEGF-A. Human vascular endothelial growth factor receptor 2 (VEGF-R2) may have the amino acid sequence of SWISS PROT Data Bank Accession No. P35968 (SEQ ID NO:21) or of fragments thereof. Illustrative examples of such fragments include the extracellular Ig-like C2-type domains 1 to 7 of VEGF-R2, comprising amino acids 46 to 110, 141 to 207, 224 to 320, 328 to 414, 421 to 548, 551 to 660, and 667 to 753, respectively. Human interleukin-4 receptor alpha chain may have the amino acid sequence of SWISS PROT Data Bank Accession No. P24394 (SEQ ID NO: 20) or of fragments thereof. An illustrative example of a fragment of human interleukin-4 receptor alpha chain includes amino acids 26 to 232 of IL-4 receptor alpha.

In general, the term "fragment", as used herein with respect to protein ligands of the tear lipocalin muteins of the invention, relates to N-terminally and/or C-terminally shortened protein or peptide ligands, which retain the capability of the full length ligand to be recognized and/or bound by a mutein according to the invention.

Therefore, another aspect of the present invention is directed to a mutein of human tear lipocalin that comprises at least one mutated amino acid residue at any two or more of the sequence positions 24-36, 53-66, 79-84, and 103-110 of the linear polypeptide sequence of the mature human tear lipocalin, and binds to IL-4 receptor alpha, VEGF-R2 or VEGF.

Human tear lipocalin muteins binding IL-4 receptor alpha may act as IL-4 antagonists and/or IL-13 antagonists. In one embodiment, the human tear lipocalin muteins act as antagonists of human IL-4 and/or IL-13. In another embodiment, the mutein is cross-reactive with the cynomolgus ligands such as IL-4 and/or IL-13 and as such acts as an antagonist of cynomolgus IL-4 receptor alpha.

A human tear lipocalin mutein of the invention that binds IL-4 receptor alpha may comprise with respect to the amino acid sequence of mature human tear lipocalin at least two amino acid substitutions of native amino acid residues by cysteine residues at any of positions 26-34, 56-58, 80, 83, 104-106, and 108 of native mature human tear lipocalin. Generally, such a mutein binds an extracellular region or a domain of IL-4 receptor alpha with a $K_D$ of 200 nM or less, 100 nM or less, 20 nM or less, or 1 nM or even less with a $K_D$ in the picomolar range. Thus, the invention also encompasses tear lipocalin muteins that bind IL-4 receptor with a $K_D$ of 900 pM or less, 600 pM or less, 500 pM or less, 250 pM, 100 pM or less, 60 pM or less or 40 pM or less. Suitable methods to determine $K_D$ values of a mutein-ligand complex are known to those skilled in the art and include fluorescence titration, competition ELISA, calorimetric methods, such as isothermal titration calorimetry (ITC), and surface plasmon resonance. Examples for such methods are detailed below (See, e.g., Examples 6, 8, 14, 16, 22, 24, and 27).

In this context it is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its ligand) given here may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

In a specific embodiment of the invention such a mutein comprises with respect to the amino acid sequence of mature human tear lipocalin at least 6, 8, 10, 12, 14 or 16 amino acid substitutions selected from the group consisting of Arg 26→Ser, Pro; Glu 27→Arg; Phe 28→Cys; Glu 30→Arg; Met 31→Ala; Asn 32→Tyr, His; Leu 33→Tyr; Glu 34→Gly, Ser, Ala, Asp, Lys, Asn, Thr, Arg; Leu 56→Gln; Ile 57→Arg; Ser 58→Ile, Ala, Arg, Val, Thr, Asn, Lys, Tyr, Leu, Met; Asp 80→Ser; Lys 83→Arg; Glu 104→Leu; Leu 105→Cys; His 106→Pro; and Lys 108→Gln.

Additionally, such a mutein may further comprise at least one amino acid substitution selected from the group consisting of Met 39→Val; Thr 42→Met, Ala; Thr 43→Ile, Pro, Ala; Glu 45→Lys, Gly; Asn 48→Asp, His, Ser, Thr; Val 53→Leu, Phe, Ile, Ala, Gly, Ser; Thr 54 →Ala, Leu; Met 55→Leu, Ala, Ile, Val, Phe, Gly, Thr, Tyr; Glu 63→Lys, Gln, Ala, Gly, Arg; Val 64→Gly, Tyr, Met, Ser, Ala, Lys, Arg, Leu, Asn, His, Thr, Ile; Ala 66→Ile, Leu, Val, Thr, Met; Glu 69→Lys, Gly; Lys 70→Arg, Gln, Glu; Thr 78→Ala; Ile 89→Val; Asp 95→Asn, Ala, Gly; and Tyr 100→His.

In one embodiment, the human tear lipocalin mutein binding IL-4 receptor alpha comprises the amino acid substitutions: Arg 26→Ser, Glu 27→Arg, Phe 28→Cys, Glu 30→Arg; Met 31→Ala, Leu 33→Tyr, Leu 56→Gln, Ile 57→Arg, Asp 80→Ser, Lys 83→Arg, Glu 104→Leu, Leu 105→Cys, His 106→Pro, and Lys 108→Gln.

In another embodiment, the human tear lipocalin mutein binding IL-4 receptor alpha comprises one of the following sets of amino acid substitutions:

(1) Arg 26→Ser; Glu 27→Arg; Phe 28→Cys; Glu 30→Arg; Met 31→Ala; Asn 32→Tyr; Leu 33→Tyr; Glu 34→Gly; Leu 56→Gln; Ile 57→Arg; Ser 58 →Ile; Asp 80→Ser; Lys 83→Arg; Glu 104→Leu; Leu 105→Cys; His 106→Pro; Lys 108→Gln;

(2) Arg 26→Ser; Glu 27→Arg; Phe 28→Cys; Glu 30→Arg; Met 31→Ala; Asn 32→Tyr; Leu 33→Tyr; Glu 34→Lys; Leu 56→Gln; Ile 57→Arg; Ser 58 →Asn; Asp 80→Ser; Lys 83→Arg; Glu 104→Leu; Leu 105→Cys; His 106 →Pro; Lys 108→Gln;

(3) Arg 26→Ser; Glu 27→Arg; Phe 28→Cys, Glu 30→Arg; Met 31→Ala; Asn 32 →Tyr; Leu 33→Tyr; Leu 56→Gln; Ile 57→Arg; Ser 58→Arg; Asp 80→Ser; Lys 83→Arg; Glu 104→Leu; Leu 105→Cys; His 106→Pro; Lys 108→Gln;

(4) Arg 26→Ser; Glu 27→Arg; Phe 28→Cys; Glu 30→Arg; Met 31→Ala; Asn 32→Tyr; Leu 33→Tyr; Glu 34→Ser; Leu 56→Gln; Ile 57→Arg; Asp 80 →Ser; Lys 83→Arg; Glu 104→Leu; Leu 105→Cys; His 106→Pro; Lys 108 →Gln;

(5) Arg 26→Ser; Glu 27→Arg; Phe 28→Cys; Glu 30→Arg; Met 31→Ala; Asn 32→His; Leu 33→Tyr; Glu 34→Ser; Leu 56→Gln; Ile 57→Arg; Ser 58 →Ala; Asp 80→Ser; Lys 83→Arg; Glu 104→Leu; Leu 105→Cys; His 106 →Pro; Lys 108→Gln;

(6) Arg 26 Ser; Glu 27→Arg; Phe 28→Cys; Glu 30→Arg; Met 31→Ala; Asn 32→Tyr; Leu 33→Tyr; Glu 34→Asp; Leu 56→Gln; Ile 57→Arg; Ser 58 →Lys; Asp 80→Ser; Lys 83→Arg; Glu 104→Leu; Leu 105→Cys; His 106 →Pro; Lys 108→Gln; and (7) Arg 26→Ser; Glu 27→Arg; Phe 28→Cys; Glu 30→Arg; Met 31→Ala; Asn 32 →Tyr; Leu 33→Tyr; Glu 34→Gly; Leu 56→Gln; Ile 57→Arg; Asp 80→Ser; Lys 83→Arg; Glu 104→Leu; Leu 105→Cys; His 106→Pro; Lys 108→Gln.

The human tear lipocalin mutein binding IL-4 receptor alpha may comprise, consists essentially of or consist of any one of the amino acid sequences set forth in SEQ ID NOs.: 2-8 or a fragment or variant thereof. In one embodiment, the mutein according to the invention comprises, consists essentially of or consists of the amino acid sequence set forth in SEQ ID NO: 5 or 6 or a fragment or variant thereof.

The term "fragment" as used in the present invention in connection with the muteins of the invention relates to proteins or peptides derived from full-length mature human tear lipocalin that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature human tear lipocalin and are usually detectable in an immunoassay of mature human tear lipocalin.

The term "variant" as used in the present invention relates to derivatives of a protein or peptide that comprise modifications of the amino acid sequence, for example by substitution, deletion, insertion or chemical modification. Preferably, such modifications do not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In a further aspect, the present invention is directed to a mutein of human tear lipocalin binding to Vascular Endothelial Growth Factor Receptor 2 (VEGF-R2) or an extracellular region or a domain thereof. Usually, such a mutein acts as a VEGF antagonist and binds an extracellular region or a domain of VEGF-R2 with a $K_D$ of 200 nM or less, 100 nM or less, 20 nM or less, 15 nM or less, 10 nM or less or even 1 nM or less.

Such a mutein may comprise with respect to the amino acid sequence of mature human tear lipocalin at least 6, 8, 10, 12, 14 or 16 amino acid substitutions selected from the group consisting of Arg 26→Ser; Glu 27→Ile; Glu 30→Ser; Met 31→Gly; Asn 32→Arg; Leu 33→Ile; Glu 34→Tyr; Leu 56→Lys, Glu, Ala, Met; Ile 57→Phe; Ser 58→Arg; Asp 80→Ser, Pro; Lys 83→Glu, Gly; Glu 104→Leu; Leu 105→Ala; His 106→Val; and Lys 108→Thr and may further comprise at least one amino acid substitution selected from the group consisting of Leu 41→Phe; Glu 63→Lys; Val 64→Met; Asp 72→Gly; Lys 76 →Arg, Glu; Ile 88→Val, Thr; Ile 89→Thr; Arg 90→Lys; Asp 95→Gly; Phe 99→Leu; and Gly 107→Arg, Lys, Glu.

In one specific embodiment, such a mutein comprises the amino acid substitutions: Arg 26 →Ser, Glu 27→Ile, Glu 30→Ser, Met 31→Gly, Asn 32→Arg, Leu 33→Ile, Glu 34→Tyr, Ile 57→Phe, Ser 58→Arg, Lys 83→Glu, Glu 104→Leu, Leu 105→Ala, His 106 →Val, and Lys 108→Thr.

A human tear lipocalin mutein of the invention that binds to an extracellular region or a domain of VEGF-R2 with detectable affinity may comprise one of the following sets of amino acid substitutions:

(1) Arg 26→Ser, Glu 27→Ile, Glu 30→Ser, Met 31→Gly, Asn 32→Arg, Leu 33 →Ile, Glu 34→Tyr, Leu 56→Lys, Ile 57→Phe, Ser 58→Arg, Asp 80→Ser, Lys 83→Glu, Glu 104→Leu, Leu 105→Ala, His 106→Val, Lys 108→Thr;

(2) Arg 26→Ser, Glu 27→Ile, Glu 30→Ser, Met 31→Gly, Asn 32→Arg, Leu 33 →Ile, Glu 34→Tyr, Leu 56→Glu, Ile 57→Phe, Ser 58→Arg, Asp 80→Ser, Lys 83→Glu, Glu 104→Leu, Leu 105→Ala, His 106→Val, Lys 108→Thr;

(3) Arg 26→Ser, Glu 27→Ile, Glu 30→Ser, Met 31→Gly, Asn 32→Arg, Leu 33 →Ile, Glu 34→Tyr, Leu 56→Ala, Ile 57→Phe, Ser 58→Arg, Asp 80→Ser, Lys 83 →Glu, Glu 104→Leu, Leu 105→Ala, His 106→Val, Lys 108→Thr; and (4) Arg 26→Ser, Glu 27→Ile, Glu 30→Ser, Met 31→Gly, Asn 32→Arg, Leu 33 →Ile, Glu 34→Tyr, Leu 56→Glu, Ile 57→Phe, Ser 58→Arg, Asp 80→Pro, Lys 83→Glu, Glu 104→Leu, Leu 105→Ala, His 106→Val, Lys 108→Thr.

In one embodiment of the invention, the mutein binding to VEGF-R2 comprises, consists essentially of or consists of any one of the amino acid sequences set forth in SEQ ID Nos.: 34-39.

In a still further aspect, the present invention is directed to a mutein of human tear lipocalin binding to Vascular Endothelial Growth Factor (VEGF). Usually, such a mutein acts a VEGF antagonist by inhibiting the binding of VEGF to the VEGF receptor and binds VEGF with a $K_D$ of 200 nM or less, 100 nM or less, 20 nM, 5 nM or less or even 1 nM or less.

Such a mutein obtainable by the methods of the invention may comprise with respect to the amino acid sequence of mature human tear lipocalin at least 6, 8, 10, 12, 14, 16 amino acid substitutions selected from the group consisting of Arg 26→Ser, Pro, Val, Leu, Ile; Glu 27 →Gly; Phe 28→Ala; Pro 29→Leu; Glu 30→Arg; Met 31→Cys; Asn 32→Leu; Leu 33→Ala; Glu 34→Gly; Leu 56→His, Arg, Tyr, Gln; Ile 57→Val, Thr, Leu; Ser 58→Lys; Asp 80→Ile; Lys 83→Ile, Val; Glu 104→Cys; His 106→Asn, Ser, Asp; and Lys 108→Ala, Val and may further comprise at least one amino acid substitution selected from the group consisting of Val 36→Met; Thr 37→Ala; Met 39→Thr; Thr 40→Ala, Ser; Asn 48→Asp; Ala 51→Val; Lys 52→Arg; Thr 54→Val; Met 55→Val; Ser 61→Pro; Lys 65 →Arg; Ala 66→Val; Val 67→Ile; Glu 69→Gly, Ser, Thr; Lys 76→Arg, Ile, Ala, Met, Pro; Tyr 87→Arg, His, Lys, Gln; Ile 89→Thr, Val, Gly, His, Met, Lys; Arg 90→Gly; Ile 98 →Val; and Gly 107→Glu.

In one embodiment, such a mutein of human tear lipocalin that binds VEGF comprises the amino acid substitutions: Glu 27→Gly, Phe 28→Ala, Pro 29→Leu, Glu 30→Arg, Met 31→Cys, Asn 32→Leu, Leu 33→Ala, Glu 34→Gly, Asp 80→Ile, Lys 83→Ile, Glu 104→Cys, and Lys 108→Val.

In another specific embodiment, the mutein of human tear lipocalin that binds VEGF may comprise one of the following sets of amino acid substitutions:

(1) Arg 26→Ser; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Asn; Lys 108→Val;

(2) Arg 26→Pro; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Glu; Asp 80→Ile; Lys 83→Ile; Glu 104→Cys; His 106→Ser; Lys 108→Val;

(3) Arg 26→Pro; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Asn; Lys 108→Val;

(4) Arg 26→Pro; Glu 27→Gly; Phe 28→Ala; Pro 29→Leu; Glu 30→Arg; Met 31 →Cys; Asn 32→Leu; Leu 33→Ala; Glu 34→Gly; Leu 56→Arg; Ser 58→Lys; Asp 80→Ile; Lys 83→Ile; Glu 104→Cys; His 106→Ser; Lys 108→Val;

(5) Arg 26→Pro; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Ser; Lys 108→Val;

(6) Arg 26→Ser; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Ser; Lys 108→Val;

(7) Arg 26→Val; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Ser; Lys 108→Val;

(8) Arg 26→Leu; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Ser; Lys 108→Val; and (9) Arg 26→Ile; Glu 27→Gly; Phe 28→Ala; Pro 29→Leu; Glu 30→Arg; Met 31 →Cys; Asn 32→Leu; Leu 33→Ala; Glu 34→Gly; Leu 56→His; Ser 58→Lys; Asp 80→Ile; Lys 83→Ile; Glu 104→Cys; His 106→Ser; Lys 108→Val.

In one embodiment of the invention, the mutein binding to VEGF comprises, consists essentially of or consists of any one of the amino acid sequences set forth in SEQ ID Nos.: 26-33 or SEQ ID Nos.: 44-47.

Also included in the scope of the present invention are the above muteins, which have been altered with respect to their potential immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class 1 molecules (Altuvia et al. (1995) *J. Mol. Biol.* 249: 244-250).

Such an approach may also be utilized to identify potential T-cell epitopes in the muteins of the invention and to make depending on its intended use a selection of a specific mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) Hybridoma 19(6):463-471) and may be adapted to the muteins of the present invention.

The muteins thus obtained may possess a minimized immunogenicity, which is desirable for their use in therapeutic and diagnostic applications, such as those described below.

For some applications, it is also useful to employ the muteins of the invention in a labeled form. Accordingly, the invention is also directed to lipocalin muteins which are conjugated to a label selected from the group consisting of enzyme labels, radioactive labels, colored labels, fluorescent labels, chromogenic labels, luminescent labels, haptens, digoxigenin, biotin, metal complexes, metals, and colloidal gold. The mutein may also be conjugated to an organic molecule. The term "organic molecule" as used herein preferably denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

In general, it is possible to label the lipocalin mutein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins of the invention may, however, also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, e al., Diphtheria-toxin receptor-targeted brain drug delivery. *International Congress Series.* 2005 1277:185-198 or Gaillard P J, et al. Targeted delivery across the blood-brain barrier. *Expert Opin Drug Deliv.* 2005 2(2): 299-309. Such moieties are for example available under the trade name 2B-Trans™ (to-BBB technologies BV, Leiden, N L).

As indicated above, a mutein of the invention may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partners for extending the half-life of a lipocalin mutein of the invention include albumin (Osborn, B. L. et al. (2002) Pharmacokinetic and pharmacodynamic studies of a human serum albumin-interferon-alpha fusion protein in cynomolgus monkeys *J. Pharmacol. Exp. Ther.* 303, 540-548), or an albumin binding protein, for example, a bacterial albumin binding domain, such as the one of streptococcal protein G (König, T. and Skerra, A. (1998) Use of an albumin-binding domain for the selective immobilisation of recombinant capture antibody fragments on ELISA plates. *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, H is, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002). "Albumin binding as a general strategy for improving the pharmacokinetics of proteins." *J Biol Chem* 277, 35035-35043).

In other embodiments, albumin itself or a biological active fragment of albumin can be used as conjugation partner of a lipocalin mutein of the invention. The term "albumin" comprises all mammal albumins such as human serum albumin or bovine serum albumin or rat albumine. The albumin or fragment thereof can be recombinantly produced as described in U.S. Pat. No. 5,728,553 or European patent applications EP 0 330 451 and EP 0 361 991. Recombinant human albumin (Recombumin®) Novozymes Delta Ltd. (Nottingham, UK) can be conjugated or fused to a lipocalin mutein in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of a mutein of the invention is to fuse to the N- or C-terminus of a mutein of the invention long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, preferably polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. Nos. 6,500,930 or 6,620,413, carbohydrate oligo- and polymers such as starch or hydroxyethyl starch (HES) can be conjugated to a mutein of the invention for the purpose of serum half-life extension.

If one of the above moieties is conjugated to the human tear lipocalin mutein of the invention, conjugation to an amino acid side chain can be advantageous. Suitable amino acid side chains may occur naturally in the amino acid sequence of human tear lipocalin or may be introduced by mutagenesis. In case a suitable binding site is introduced via mutagenesis, one possibility is the replacement of an amino acid at the appropriate position by a cysteine residue. In one embodiment, such mutation includes at least one of Thr 40Cys, Glu 73→Cys, Arg 90→Cys, Asp 95→Cys or Glu 131→Cys substitution. The newly created cysteine residue at any of these positions can in the following be utilized to conjugate the mutein to moiety prolonging the serum half-life of the mutein, such as PEG or an activated derivative thereof.

In another embodiment, in order to provide suitable amino acid side chains for conjugating one of the above moieties to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein it may be advantageous to use them in the form of fusion proteins. In some embodiments, the inventive human tear lipocalin mutein is fused at its N-terminus or its C-terminus to a protein, a protein domain or a peptide such as a signal sequence and/or an affinity tag.

For pharmaceutical applications a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugates described above, the fusion partner may be an Fc part of an immunoglobulin, a CH3 domain of an immunoglobulin, a CH4 domain of an immuglobulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) *supra J. Pharmacol. Exp. Ther.* 303, 540-548), or an albumin binding protein, for example, a bacterial albumin binding domain, such as the one of streptococcal protein G (König, T. and Skerra, A. (1998) *supra J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" comprises all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-5-transferase, the albumin-binding domain of protein G, protein A, antibody fragments, oligomerization domains, lipocalin muteins of same or different binding specificity (which results in the formation of "Duocalins", cf. Schlehuber, S., and Skerra, A. (2001), Duocalins, engineered ligand-binding proteins with dual specificity derived from the lipocalin fold. *Biol. Chem.* 382, 1335-1342) or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target. Affinity tags such as the Strep-tag® or Strep-tag® II (Schmidt, T. G. M. et al. (1996) *J. Mol. Biol.* 255, 753-766), the myc-tag, the FLAG-tag, the $His_6$-tag or the HA-tag or proteins such as glutathione-5-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also comprises lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional mutein.

Therefore, the present invention also includes a nucleic acid sequence encoding a mutein according to the invention comprising a mutation at least one codon of any of the amino acid sequence positions 26-34, 56-58, 80, 83, 104-106 and 108 of the linear polypeptide sequence of native mature human tear lipocalin, wherein the codons encoding at least one of the cysteine residues at sequence positions 61 and 153 of the linear polypeptide sequence of the mature human tear lipocalin have been mutated to encode any other amino acid residue.

The invention as disclosed herein also includes nucleic acid molecules encoding tear lipocalin muteins, which comprise additional mutations outside the indicated sequence positions of experimental mutagenesis. Such mutations are often tolerated or can even prove to be advantageous, for example if they contribute to an improved folding efficiency, serum stability, thermal stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome.

In one embodiment, the nucleic acid molecule is comprised in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York N.Y.; Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), *supra*). Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), *supra*). The host cell is then cultured under conditions, which allow expression of the heterologous DNA and thus the synthesis of the corresponding polypeptide. Subsequently, the polypeptide is recovered either from the cell or from the cultivation medium.

In some tear lipocalin muteins of the invention, the naturally occurring disulfide bond between Cys 61 and Cys 153 is removed. Accordingly, such muteins (or any other tear lipocalin mutein that does not comprise an intramolecular disulfide bond) can be produced in a cell compartment having a reducing redox milieu, for example, in the cytoplasma of Gram-negative bacteria. In case a lipocalin mutein of the invention comprises intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. (2002) "High level production of functional antibody Fab fragments in an oxidizing bacterial cytoplasm." *J. Mol. Biol.* 315, 1-8.).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams, P. et al. (1997) *Chemical Approaches to the Synthesis of Peptides and Proteins*. CRC Press, Boca Raton, Fields, G. B., and Colowick, S. P. (1997) *Solid-Phase Peptide Synthesis*. Academic Press, San Diego, or Bruckdorfer, T. et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition comprising at least one inventive mutein of human tear lipocalin or a fusion protein or conjugate thereof and a pharmaceutically acceptable excipient.

The lipocalin muteins according to the invention can be administered via any parenteral or non-parenteral (enteral) route that is therapeutically effective for proteinaceous drugs. Parenteral application methods comprise, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drug delivery, i.e. either via inhalation of aerosols (which can also be used in intranasal administration) or intracheal instiallation is given by J. S. Patton et al. The lungs as a portal of entry for systemic drug delivery. Proc. Amer. Thoracic Soc. 2004 Vol. 1 pages 338-344, for example). Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of the tear lipocalin mutein can be used. However, if wanted, the mutein may also be given in a sustained release formulation, for example liposomal dispersions or hydrogel-based polymer microspheres, like PolyActive™ or OctoDEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the muteins of the present invention can be formulated into compositions using pharmaceutically acceptable ingredients as well as established methods of preparation (Gennaro, A. L. and Gennaro, A. R. (2000) *Remington: The Science and Practice of Pharmacy*, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

Another aspect of the present invention relates to a method of treating a disease or disorder, comprising administering a pharmaceutical composition comprising a mutein as defined above to a subject in need thereof.

The subject in need of such a treatment may be a mammal, such as a human, a dog, a mouse, a rat, a pig, an ape such as cymologous to name only a few illustrative examples.

The precise nature of the diseases and disorders that are to be treated according to the method of the invention depends on the ligand that the utilized mutein is intended to bind. Accordingly, the muteins of the present invention can be use to treat any disease as long as a target molecule that is known to be involved in the development of the disease or disorder can be displayed to the expression product of a nucleic acid library of the present invention or displayed to otherwise obtained muteins of tear lipocalin.

The above described muteins binding IL-4 receptor alpha with high affinity or pharmaceutical compositions containing them may be utilized in a method of treating a disease or disorder associated with an increase of the Th2 immune response. Such disease or disorder may, for example, be an allergic reaction or an allergic inflammation. The allergic inflammation, in turn, may be associated with allergic asthma, rhinitis, conjunctivitis or dermatitis (cf., Hage et al., Crystal Structure of the Interleukin-4 Receptor alpha chain complex reveals a mosaic binding interface, i Cell, Vol. 97, 271-281, Apr. 16, 1999 or Mueller et al, Structure, binding and antagonists in the IL-4/IL-13 receptor system, Biochemica et Biophysica Acta (2002), 237-250).

In this context it is noted that a variety of tumor cells express a greater number of high affinity IL-4 receptors than normal cells. Such cells include solid human tumor such as melanoma, breast cancer, ovarian carcinoma, mesothelioma, glioblastoma, astrocytoma, renal cell carcinoma, head and neck carcinoma, AIDS associated Kaposi's sarcoma=AIDS KS, hormone dependent and independent prostate carcinoma cells, and primary cultures from prostate tumors, for example (cf., Garland L, Gitlitz B, et al., Journal of Immunotherapy. 28: 376-381, No. 4, July-August 2005; Rand R W, Kreitman R J, et al. Clinical Cancer Research. 6: 2157-2165, June 2000; Husain S R, Kreitman R J, et al. Nature Medicine. 5: 817-822, July 1999; Puri R K, Hoon D S, et al. Cancer Research. 56: 5631-5637, 15 Dec. 1996, 10. Debinski W, Puri R, et al, or Husain S R, Behari N, et al. Cancer Research. 58: 3649-3653, 15 Aug. 1998, Kawakami K, Leland P, et al. Cancer Research. 60: 2981-2987, 1 Jun. 2000; or Strome S E, Kawakami K, et al. Clinical Cancer Research. 8: 281-286, January 2002, for example. Specific examples of cells with documents overexpression of IL-4 receptors include, but are not limited to, Burkitt lymphoma cell line Jijoye (B-cell lymphom), prostate carcinoma (LNCaP, DU145), head and neck carcinoma (SCC, KCCT873), Pranceatic cancer (PANC-1 cell line), SCC-25: 13.000 (+/−500) h head and neck cancer cell line (ATCC). IL4R alpha chain plays a major role in IL4-internalization. Accordingly, when fused or conjugated to a toxin, the tear lipocalin muteins binding to IL-4 Receptor alpha chain can therefore also be used for the treatment of tumors (cancer). Examples of suitable toxins include *Pseudomonas* exotoxin, pertussis-toxin, diphtheria toxin, ricin, saporin, pseudomonas exotoxin, calicheamicin or a derivative thereof, a taxoid, a maytansinoid, a tubulysin and a dolastatin analogue. Examples of dolastatin analogues include, but are not limited to, auristatin E, monomethylauristatin E, auristatin PYE and auristatin PHE.

For the treatment of cancer, it is also possible to conjugate muteins binding to IL-4 Receptor alpha chain to a cystostatic agent. Examples of such cystostatic agents include Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin.

In this connection it is also pointed out that fusions or conjugates of tear lipocalin muteins of the invention with toxins or cystostatic agent are of course not limited to muteins with affinity to IL-4 Receptor alpha chain. Rather, as immediately evident for the person skilled in the art, any tear lipocalin mutein that binds to a receptor expressed on a surface of cancer cells can be used in form of a fusion protein or a conjugate for the treatment of cancer.

The human tear lipocalin muteins binding VEGF-R2 or VEGF with high affinity or pharmaceutical compositions containing them may be utilized in a method for the treatment of a disease or disorder connected to an increased vascularization such as cancer, neovascular wet age-related macular degeneration (AMD), diabetic retinopathy or macular edema, retinopathy of prematurity or retinal vein occlusion. Such a cancer may be selected from the group consisting of carcinomas of the gastrointestinal tract, rectum, colon, prostate, ovaries, pancreas, breast, bladder, kidney, endometrium, and lung, leukaemia, and melanoma, to name only a few illustrative examples.

As is evident from the above disclosure, a mutein of the present invention or a fusion protein or a conjugate thereof can be employed in many applications. In general, such a mutein can be used in all applications antibodies are used, except those with specifically rely on the glycosylation of the Fc part.

Therefore, in another aspect of the invention, the invented muteins of human tear lipocalin are used for the detection of a given non-natural ligand of human tear lipocalin. Such use may comprise the steps of contacting the mutein with a sample suspected of containing the given ligand under suitable conditions, thereby allowing formation of a complex between the mutein and the given ligand, and detecting the complexed mutein by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins of human tear lipocalin disclosed herein may also be used for the separation of a given non-natural ligand of human tear lipocalin. Such use may comprise the steps of contacting the mutein with a sample supposed to contain said ligand under suitable conditions, thereby allowing formation of a complex between the mutein and the given ligand, and separating the mutein/ligand complex from the sample.

In both the use of the mutein for the detection of a given non-natural ligand as well as the separation of a given ligand, the mutein and/or the target may be immobilized on a suitable solid phase.

The human tear lipocalin muteins of the invention may also be used to target a compound to a preselected site. For such a purpose the mutein is contacted with the compound of interest in order to allow complex formation. Then the complex comprising the mutein and the compound of interest are delivered to the preselected site. This use is in particular suitable, but not restricted to, for delivering a drug (selectively) to a preselected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the preselected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

Thus, the present invention also involves the use of the human tear lipocalin muteins of the invention for complex formation with a given non-natural ligand.

Another related and preferred use of a mutein described herein is target validation, i.e. the analysis whether a polypeptide assumed to be involved in the development or progress of a disease or disorder is indeed somehow causative of that disease or disorder. This use for validating a protein as a pharmacological drug target takes advantage of the ability of a mutein of the present invention to specifically recognize a surface area of a protein in its native conformation, i.e. to bind to a native epitope. In this respect, it is to be noted that this ability has been reported only for a limited number of recombinant antibodies. However, the use of an inventive mutein for validation of a drug target is not limited to the detection of proteins as targets, but also includes the detection of protein domains, peptides, nucleic acid molecules, organic molecules or metal complexes.

BRIEF DESCRIPTION OF THE DRAWINGS

The invention is further illustrated by the following non-limiting Examples and the attached drawings in which:

FIG. 1 shows a map of the expression vector pTLPC10 (SEQ ID NO:1).

FIG. 2 shows the polypeptide sequence of S148.3 J14 (SEQ ID NO: 2), a mutein of human tear lipocalin possessing binding affinity for the IL-4 receptor alpha.

FIG. 3 shows the method of affinity screening via ELISA and the results obtained for muteins with affinity for IL-4 receptor alpha.

FIG. 4 shows the polypeptide sequences of the muteins with the highest affinity for IL-4 receptor alpha (SEQ ID NOs.:3-8).

FIGS. 19a to 19d show a TF-1 cell proliferation assay in presence of IL-4 (FIG. 19a, FIG. 19b) or IL-13 (FIG. 19c, FIG. 19d) and human tear lipocalin muteins of the invention (S191.5 K12, S148.3 J14AM2C2, S191.4 B24, S191.4 K19, S191.5 H16, and S197.8 D22 [SEQ ID NOs: 3-8]).

FIG. 20 shows a map of the expression vector pTLPC27 (SEQ ID NO:9).

FIGS. 21a to 21d show a proliferation assay with endothelial cells cultured from human umbilical vein (HUVEC) in presence of human VEGF165 and human tear lipocalin muteins of the invention (S209.2 C23, S209.2 D16, S209.2 N9, S209.6 H7, S209.6 H10, S209.2 M17, S209.2 O10 [SEQ ID NOs: 27-33]), wildtype tear lipocalin (gene product of pTLPC10; control) or Avastin® (Roche; control).

FIG. 25 shows the results of stability test of the tear lipocalin mutein S236.1-A22 (SEQ ID NO:44) in human plasma and vitreous liquid (FIG. 25A) and results of stability tests of a fusion protein of the mutein S236.1-A22 with an albumin-binding domain (ABD) (SEQ ID NO:51) (FIG. 25B).

FIGS. 38a and 38b show the results of a Schild analysis of the IL-4 receptor alpha binding mutein S191.4 B24 (SEQ ID NO:4).

FIGS. 39a-39c show the result of an affinity assessment of the IL-4 receptor alpha binding mutein S191.4 B24 (SEQ ID NO:4) for human primary B cells.

FIG. 1 shows the expression vector pTLPC10 which encodes a fusion protein comprising the OmpA signal sequence (OmpA), the T7 affinity tag and a mutated human tear lipocalin (Tlc) followed by the Strep-tag II. Both the BstXI-restriction sites used for the cloning of the mutated gene cassette and the restriction sites flanking the structural gene are labeled. Gene expression is under the control of the tetracycline promoter/operator (tet$^{p/o}$). Transcription is terminated at the lipoprotein transcription terminator ($t_{lpp}$). The vector further comprises an origin of replication (ori), the intergenic region of the filamentous phage f1 (f1-IG), the ampicillin resistance gene (amp) and the tetracycline repressor gene (tetR). A relevant segment of the nucleic acid sequence of pTLPC10 is reproduced together with the encoded amino acid sequence in the sequence listing as SEQ ID NO:1. The segment begins with the XbaI restriction site and ends with the HindIII restriction site. The vector elements outside this region are identical with the vector pASK75, the complete nucleotide sequence of which is given in the German patent publication DE 44 17 598 A1.

FIG. 2 shows the primary structure of a human tear lipocalin mutein of the invention (S148.3 J14) that exhibits binding affinity for IL-4 receptor alpha. The first 21 residues (underlined) constitute the signal sequence, which is cleaved upon periplasmic expression. The N-terminal T7-tag (italic) and the C-terminal Streptag-II (bold) are part of the characterized protein. FIG. 2 also shows that 4 N-terminal amino acid residues (H1 H2 L3 A4) as well as the two last C-terminal amino acid residues (S157 and D158) are deleted in this illustrative mutein of the invention.

FIG. 3 shows results from affinity screening experiments. Monoclonal anti-StrepTag antibody (Qiagen) was coated onto the ELISA plate in order to capture the expressed muteins of human tear lipocalin and binding of IL-4 receptor alpha-Fc (R&D Systems; 3 nM and 0.75 nM) to the captured muteins was detected using an horseradish peroxidase (HRP)-conjugated polyclonal antibody against the Fc domain of IL-4 receptor alpha-Fc. Affinity improved clones give higher signals (left). IL-4 was coated onto the ELISA plate and IL-4 receptor alpha-Fc (3 nM) was incubated with the expressed muteins. Binding of IL-4 receptor alpha-Fc having an unoccupied IL-4 binding site was detected using a HRP-conjugated polyclonal antibody against the Fc domain of IL-4 receptor alpha-Fc. Antagonistic affinity improved clones give lower signals (right). The signals corresponding to the mutein of the invention S148.3 J14 (SEQ ID NO:2) are marked with arrows and the signals from individual clones are depicted by diamonds.

FIG. 4 shows the polypeptide sequences of the six muteins of human tear lipocalin with the highest binding affinity for IL-4 receptor alpha (S191.5 K12, S148.3 J14AM2C2, S191.4 B24, S191.4 K19, S191.5H16, and S197.8 D22 [SEQ ID Nos: 3-8]) obtained by affinity maturation of SEQ ID NO:2 (S148.3 J14). The first 21 residues (underlined) of the represented primary structure constitute the signal sequence, which is cleaved upon periplasmic expression. The C-terminal StrepTag-II (bold) is part of the characterized protein. Also FIG. 4 shows that, for example, the first 4 N-terminal amino acid residues (HHLA) as well as the two last C-terminal amino acid residues (SD) can be deleted in a tear lipocalin mutein of the invention without affecting the biological function of the protein.

FIG. 5-11 show Biacore measurements of the muteins of human tear lipocalin with affinity for IL-4 receptor alpha (S148.3 J14, S191.5 K12, S148.3 J14AM2C2, S191.4 B24, S191.4 K19, S191.5H16, and S197.8 D22 [SEQ ID Nos: 2-8]). ~400 RU of IL-4 receptor alpha-Fc was captured on a CM-5 chip, which had previously been coated with an anti human-Fc monoclonal antibody. Subsequently, mutein in different concentrations (FIG. 5: 20 nM; 40 nM; 80 nM; 160 nM; 320 nM) or in a single concentration of 25 nM (FIG. 6-11) was passed over the flowcell and changes in resonance units recorded. Reference signals from a flow cell that was equally treated apart from not having any IL-4 receptor alpha-Fc was subtracted and the resulting data fitted to a 1:1 Langmuir model using the BIAevaluation software. Due to the slow dissociation kinetics of the interaction in the experiments illustrated in FIGS. 6-11 double referencing was used by subtracting the signals from a flow cell that was equally treated apart from not having any IL-4 receptor alpha-Fc and subtracting the signal from an experiment where only sample buffer was injected. The resulting data was fitted to a 1:1 Langmuir model with mass-transport limitation using the BIAevaluation software. In FIGS. 6-11 the result of one representative out of five experiments is shown.

FIG. 12 shows competition ELISA measurements of a human tear lipocalin mutein with binding affinity for IL-4 receptor alpha (S148.3 J14; SEQ ID NO:2). IL-4 (20 µg/ml) was coated onto an ELISA plate and IL-4 receptor alpha-Fc (15 nM) was incubated together with various concentrations of human tear lipocalin mutein or IL-4 receptor-specific monoclonal antibody (MAB230, R&D Systems) for 1 h at room temperature. The IL-4 receptor alpha-Fc and mutein mixture was the given to the IL-4 coated plates for 30 min at ambient temperature. Bound IL-4 receptor alpha-Fc was detected with a goat anti-human-Fc-HRP-conjugated antibody. The data was fitted to the expression: $0.5*(-m0+m2-m1+sqrt((-m0+m2-m1)^2+4*m1*m2))$. Ki is given by the variable m1. The result of one representative out of three experiments is shown.

FIG. 13-18 show competition ELISA measurements of the human tear lipocalin muteins with binding affinity for IL-4 receptor alpha and wildtype tear lipocalin (TLPC10; gene product of pTLPC10) as control. IL-4 receptor alpha-specific monoclonal antibody MAB230 (R&D Systems) against IL-4 receptor was coated onto an ELISA plate and biotinylated IL-4 receptor alpha (IL-4R alpha-bio; 0.5 nM) was incubated together with various concentrations of the invented muteins or TLPC10 for 1 h at ambient temperature. The IL-4R alpha-bio and mutein mixture was incubated in the MAB230-coated plates for 30 min at ambient temperature. Bound IL-4R alpha-bio was detected with Extravidin-HRP. The data were fitted to the expression: $0.5*(-m0+m2-m1+sqrt((-m0+m2-m1)^2+4*m1*m2))$. $K_D$ is given by the variable m1. The result of one representative out of three experiments is shown.

FIG. 19 shows the results of TF-1 cell proliferation assays. TF-1 cells were incubated for 1 hour at 37° C. with the indicated muteins, an IL-4 receptor alpha-specific monoclonal antibody or a IgG2a antibody isotype control in a dilution series before addition of 0.8 ng/ml IL-4 (a, b) or 12 ng/ml IL-13 (c, d) for 72 h. Proliferation was measured by $^3$H-thymidine incorporation.

FIG. 20 shows the phasmid vector pTLPC27 which encodes a fusion protein comprising the OmpA signal sequence (OmpA), Tlc followed by the Strep-tag II, and a truncated form of the M13 coat protein pIII, comprising amino acids 217 to 406 (pIII). An amber stop codon, which is partially translated to Gln in SupE amber suppressor host strain, is located between the Tlc coding region, including the Strep-tagII, and the coding region for the truncated phage coat protein pIII to allow soluble expression of the Tlc mutein without the M13 coat protein pill when employing a non-suppressor *E. coli* strain. Both the BstXI-restriction sites used for the cloning of the mutated gene cassette and the restriction sites flanking the structural gene are labeled. Gene expression is under the control of the tetracycline promoter/operator ($tet^{p/o}$). Transcription is terminated at the lipoprotein transcription terminator ($t_{lpp}$). The vector further comprises an origin of replication (ori), the intergenic region of the filamentous phage f1 (f1-IG), the chloramphenicol resistance gene (cat) coding for chloramphenicol acetyl transferase and the tetracycline repressor gene (tetR). A relevant segment of the nucleic acid sequence of pTLPC27 is reproduced together with the encoded amino acid sequence in the sequence listing as SEQ ID NO:9.

FIG. 21 shows the results of a proliferation assay employing the human tear lipocalin muteins with binding affinity for human VEGF, wildtype tear lipocalin (TLPC10) or VEGF-specific therapeutic antibody Avastin®. Approximately 1.400 HUVEC cells were seeded in complete medium and after overnight incubation at 37° C., cells were washed and basal medium containing 0.5% FCS, hydrocortisone and gentamycin/amphotericin was added. VEGF-specific mutein S209.2-C23, S209.2-D16, S209.2-N9, S209.6-H7, S209.6-H10, S209.2-M17, S209.2-O10 (SEQ ID NOs: 27-33), wildtype tear lipocalin (gene product of pTLPC10; as control) or therapeutic VEGF-specific monoclonal antibody Avastin® (Roche; as control) was added at the indicated concentration in triplicate wells. After 30 min, either human VEGF165 or human FGF-2, as a control for proliferation not induced by VEGF (not shown), was added and the viability of the cells was assessed after 6 days with CellTiter 96 Aqueous One chromogenic assay (Promega).

FIG. 22 shows Biacore measurements of the PEGylated mutein S148.3 J14 (SEQ ID NO:2) of human tear lipocalin with affinity for IL-4 receptor alpha. ~400 RU of IL-4 receptor alpha-Fc was captured on a CM-5 chip, which had previously been coated with an anti human-Fc monoclonal antibody. Subsequently, mutein in different concentrations (200 nM; 67 nM; 22 nM was passed over the flowcell and changes in resonance units were recorded. Reference signals from a flow cell that was equally treated apart from not having any IL-4 receptor alpha-Fc was subtracted and the resulting data were fitted to a 1:1 Langmuir model using the BIAevaluation software.

FIG. 23 shows exemplary Biacore measurements of the binding of human tear lipocalin mutein S236.1-A22 (SEQ ID NO:44) to immobilized $VEGF_{8-109}$. $VEGF_{8-109}$ was immobilized on a CM5 chip using standard amine chemistry. Lipocalin mutein S236.1-A22 was applied with a flow rate of 30 µl/min at six concentrations from 500 nM to 16 nM. Evaluation of sensorgrams was performed with BIA T100 software to determine $k_{on}$, $k_{off}$ and $K_D$ of the mutein.

FIG. 24 shows affinity measurements of the mutein S236.1-A22 (SEQ ID NO:44) that was immobilized on a sensor chip with different forms of VEGF. Affinity measurements were performed essentially as described in Example 9 of WO 2006/56464 with the modifications that the mutein was immobilized and 70 µl of sample containing the different VEGF variants was injected at a concentration of 250 nM. The qualitative comparison of the results illustrate that the truncated form $hVEGF_{8-109}$ and $hVEGF_{121}$ show basically identical sensorgrams indicating similar affinity to the tear lipocalin mutein S236.1-A22 (SEQ ID NO:44). The splice form $hVEGF_{165}$ also shows strong binding to the lipocalin mutein, while the respective mouse ortholog $mVEGF_{164}$ has slightly reduced affinity.

FIG. 25 shows a stability test of VEGF-binding mutein S236.1-A22 at 37° C. in PBS and human serum that was performed essentially as described in Example 15 of the International patent application WO2006/056464 except that the concentration utilized was 1 mg/ml. No alteration of the mutein could be detected during the seven day incubation period in PBS as judged by HPLC-SEC (data not shown). Incubation of the lipocalin mutein in human serum resulted in a drop of affinity after 7 days to approx. 70% compared to the reference (FIG. 25a). The stability of the ABD-fusion of S236.1-A22 (SEQ ID NO:51) in human serum was also tested as described above. No loss of activity could be detected during the seven day incubation period (FIG. 25b)

FIG. 26 shows the expression vector pTLPC51 which encodes a fusion protein comprising the OmpA signal sequence (OmpA), a mutated human tear lipocalin (Tlc), fused to an albumin-binding domain (abd), followed by a Strep-tag II. Both the BstXI-restriction sites used for the cloning of the mutated gene cassette and the restriction sites flanking the structural gene are labeled. Gene expression is under the control of the tetracycline promoter/operator ($tet^{p/o}$). Transcription is terminated at the lipoprotein transcription terminator ($t_{lpp}$). The vector further comprises an origin of replication (ori), the intergenic region of the filamentous phage f1 (f1-IG), the ampicillin resistance gene (amp) and the tetracycline repressor gene (tetR). A relevant segment of the nucleic acid sequence of pTLPC51 is reproduced together with the encoded amino acid sequence in the sequence listing as SEQ ID NOs:48 and 49. The segment begins with the XbaI restriction site and ends with the HindIII restriction site. The vector elements outside this region are identical with the vector pASK75, the complete nucleotide sequence of which is given in the German patent publication DE 44 17 598 A1.

FIG. 27 shows affinity measurements of the ABD-fusion of tear lipocalin mutein S236.1-A22 (A22-ABD) (SEQ ID NO:51) (200 pM) towards recombinant $VEGF_{8-109}$ using surface plasmon resonance (Biacore). Affinity measurements were performed essentially as described in Example 9 of WO 2006/56464 with the modifications that approximately 250 RU of recombinant $VEGF_{8-109}$ was directly coupled to the sensor chip using standard amine chemistry. 40 µl of the mutein was injected at a concentration of 400 nM. The affinity was found basically unaltered and measured to be 260 µM.

FIG. 28 shows a test of the functionality of the lipocalin mutein A22-ABD (ABD-fusion of S236.1-A22) in the presence of human serum albumin by assessing its ability to inhibit VEGF induced HUVEC proliferation. HUVEC (Promocell) were propagated on gelatine-coated dishes and used between passages P2 and P8. On day 1, 1400 cells were seeded per well in a 96 well plate in complete medium. On day 2, cells were washed and 100 µl of basal medium containing 0.5% FCS, hydrocortisone and gentamycin/amphotericin was added. Proliferation was stimulated with 20 ng/ml $VEGF_{165}$ or 10 ng/ml FGF-2 which were mixed with the lipocalin mutein S236.1-A22-ABD (SEQ ID NO:51), incubated for 30 min and added to the wells. Viability was determined on day 6 and the results expressed as % inhibition. Human serum albumin (HSA, 5 µM) was added where indicated. At 5 µM HSA, >99.8% of A22-ABD is associated with HSA at any given time.

FIG. 29 shows the inhibition of VEGF induced HUVEC proliferation by muteins of the invention. HUVEC (Promocell) were propagated on gelatine-coated dishes and used between passages P2 and P8. On day 1, 1400 cells were seeded per well in a 96 well plate in complete medium. On day 2, cells were washed and 100 µl of basal medium containing 0.5% FCS, hydrocortisone and gentamycin/amphotericin was added. Proliferation was stimulated with 20 ng/ml VEGF165 or 10 ng/ml FGF-2 which were mixed with the lipocalin mutein S236.1-A22 (SEQ ID NO:44), incubated for 30 min and added to the wells. Viability was determined on day 6 and the results expressed as % inhibition.

FIG. 30 shows the Inhibition of VEGF-mediated MAP Kinase activation in HUVEC by muteins of the present invention. HUVEC were seeded in 96-well plates at 1,400 cells per well in standard medium (Promocell, Heidelberg). On the following day, FCS was reduced to 0.5% and cultivation was continued for 16 h. Cells were then starved in 0.5% BSA in basal medium for 5 h. HUVEC were stimulated with $VEGF_{165}$ (Reliatech, Braunschweig) for 10 min in the presence of increasing concentrations of tear lipocalin mutein A22 or Avastin (bevacizumab, Genentech/Roche) in order to obtain a dose-response curve. Phosphorylation of the MAP kinases ERK1 and ERK2 was quantified using an ELISA according to the manufacturer's manual (Active Motif, Rixensart, Belgium). The IC 50 value was determined to be 4.5 nM for the mutein A22 (SEQ ID NO:44) and 13 nM for Avastin®.

FIG. 31 shows a vascular permeability assay with local administration of tear lipocalin mutein. Duncan-Hartley guinea pigs weighing 350±50 g were shaved on the shoulder and on the dorsum. The animals received an intravenous injection via the ear vein of 1 ml of 1% Evan's Blue dye. Thirty minutes later 20 ng $VEGF_{165}$ (Calbiochem) was mixed with test substance or control article at a tenfold molar excess and injected intradermally on a 3×4 grid. Thirty minutes later, animals were euthanized by $CO_2$ asphyxiation. One hour after the VEGF injections, the skin containing the grid pattern was removed and cleaned of connective tissue. The area of dye extravasation was quantified by use of an image analyzer (Image Pro Plus 1.3, Media Cybernetics).

FIG. 32 shows a chick chorioallantoic membrane (CAM) assay. Collagen onplants containing FGF-2 (500 ng), VEGF (150 ng) and tear lipocalin mutein (1.35 µg) or Avastin (10 µg) as indicated were placed onto the CAM of 10 day chicken embryos (4/animal, 10 animals/group). At 24 h the tear lipocalin mutein or Avastin were reapplied topically to the onplant at the same dose. After 72 h onplants were collected and images were captured. The percentage of positive grids containing at least one vessel was determined by a blinded observer. The median angiogenic index is reported for the VEGF antagonists S209.2-O10 (SEQ ID NO:33) and Avastin® as well as wild type tear lipocalin control as the fraction of positive grids.

FIG. 33 shows the determination of pharmacokinetic (PK) parameters for A22 and A22-ABD in mice. Pharmacokinetic (PK) parameters (half-life plasma concentration, bioavailibity) for tear lipocalin mutein S236.1 A22 (SEQ ID NO:44) (4 mg/kg) after i.v. and the fusion protein of muteiin S236.1 A22 with ABD (SEQ ID NO:51) (5.4 mg/kg) following i.v. or i.p. single bolus administration were determined in NMRI mice. Plasma was prepared from terminal blood samples taken at pre-determined timepoints and the concentrations of the lipocalin mutein were determines by ELISA. Results were analyzed using WinNonlin software (Pharsight Corp., Mountain View, USA). $T_{1/2}$ A22 i.v.: 0.42 h; $T_{1/2}$ A22-ABD i.v.: 18.32 h; $T_{1/2}$ A22-ABD i.p.: 20.82 h. The bioavailability following i.p. administration of the fusion protein A22-ABD was 82.5%.

FIG. 34 shows a vascular permeability assay with systemic administration of tear lipocalin mutein. Twelve hours prior to the experiment, test substances or controls were injected intravenously into 3 animals per group. Group 1: PBS vehicle; Group 2: Avastin, 10 mg/kg; Group 3: mutein S236.1 A22-ABD, 6.1 mg/kg; Group 4: TLPC51: 6.1 mg/kg. At time=0 Evan's Blue was injected. Thirty minutes later, 4 doses of VEGF (5, 10, 20 or 40 ng) were injected intradermally in triplicate on a 3×4 grid. Thirty minutes after the VEGF injections the animals were sacrificed and dye extravasation was quantified by use of an image analyzer (Image Pro Plus 1.3, Media Cybernetics).

FIG. 35 shows the effect of the muteins of the invention in a tumor xenograft model. Irradiated (2.5 Gy, $Co^{60}$) Swiss nude mice were inoculated subcutaneously with $1×10^7$ A673 rhabdomyosarcoma cells (ATTC) in matrigel into the right flank (n=12 per group). Treatments were administered intraperitoneally and were initiated on the same day and continued for 21 days. Group 1: PBS vehicle, daily; Group 2: Avastin (bevacizumab, Genentech/Roche), 5 mg/kg every 3 days; Group 3: lipocalin mutein A22-ABD (SEQ ID NO:51), daily, 3.1 mg/kg; Group 4: TLPC51, daily, 3.1 mg/kg. The dose of the lipocalin mutein A22-ABD was chosen to achieve the constant presence of an equimolar number of VEGF binding sites of the mutein and Avastin based on the A22-ABD PK data and estimated serum half life of antibodies in mice. Tumor size was measured twice weekly with a calliper and the tumor volume was estimated according to the formula (length×width$^2$)/2. Mice were sacrificed when the tumor volume exceeded 2,000 mm$^3$.

FIG. 36 shows the results of an Eotaxin-3 secretion assay with A549 cells. A549 cells were stimulated with 0.7 nM IL-4 or 0.83 nM IL-13 respectively in the absence and presence of increasing concentrations of the IL-4 receptor alpha binding mutein S191.4 B24 (SEQ ID NO:4). Eotaxin-3 secretion was assessed after 72 hours by measuring Eotaxin 3 concentrations in the cell culture supernatent using a commercially available kit.

FIG. 37 shows the IL-4/IL-13 induced CD23 expression on stimulated peripheral blood mononuclear cells (PBMCs) after 48 h in the absence and presence of increasing concentrations of the IL-4 receptor alpha binding mutein S191.4 B24 (SEQ ID NO:4). Total human PBMCs were isolated from buffy coat. Increasing concentrations of the IL-4 receptor alpha binding mutein S191.4 B24 were added and cells were stimulated with IL-4 or IL-13 at final concentrations of 1.0 nM or 2.5 nM, respectively. After 48 hours, activated, CD23 expressing $CD14^+$ monocytes were quantified by flow cytometry.

FIG. 40 shows the results of a bioavailability test of the IL-4 receptor alpha binding mutein S191.4 B24 after intravenous, subcutaneous or intratracheal administration. Sprague-Dawley rats received a single dose of the mutein S191.4 B24 at 4 mg/kg via the indicated routes. Intratracheal administration was performed with a microspray dosing device (Penn-Century, USA). Plasma samples were obtained at predetermined time points and subjected to a sandwich ELISA analysis in order to determine the remaining concentrations of the functionally active mutein. Concentrations were analyzed by non-compartmental PK analysis. Bioavailability was 100% after subcutaneous administration and 13.8% following intratracheal delivery.

FIG. 41 shows an in vitro potency assessment of the mutein S236.1-A22 (SEQ ID NO:44) either unPEGylated or PEGylated with PEG20, PEG30 or PEG40 compared to human tear lipocalin wt. The $IC_{50}$ values were determined via titration of the respective human tear lipocalin mutein in a VEGF-stimulated HUVEC proliferation assay and determining the proliferation inhibition.

EXAMPLES

Figure 5:
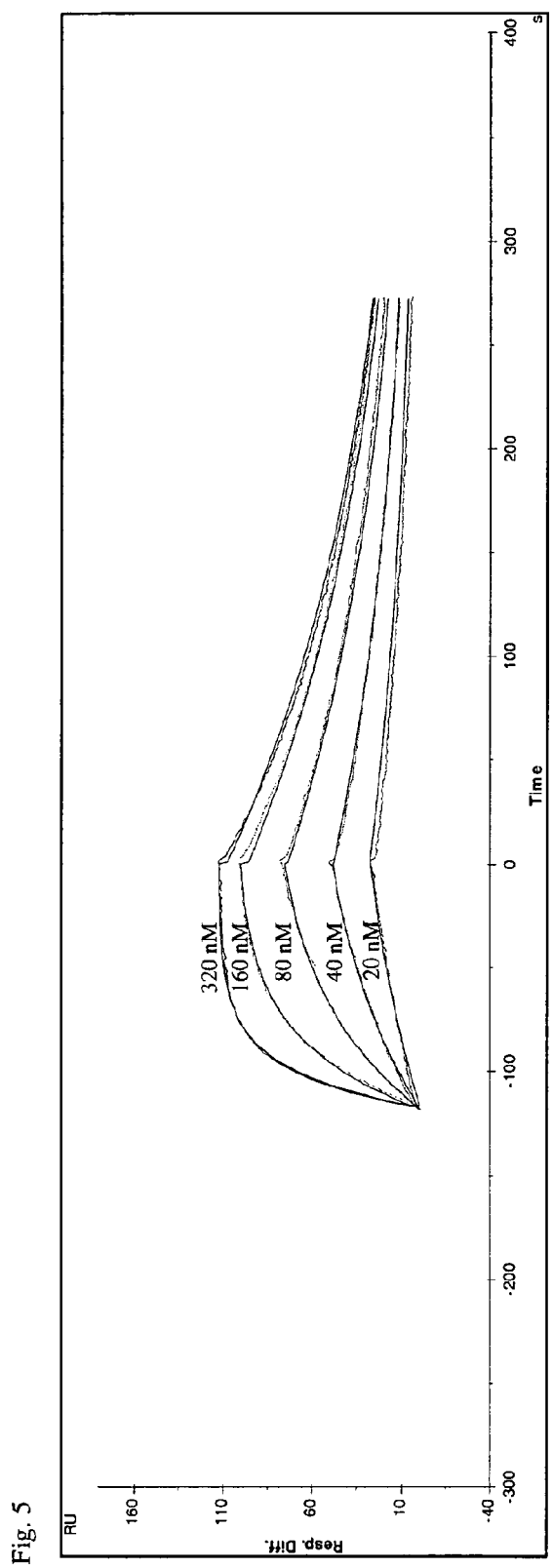
FIG. 5 shows BIAcore measurements of the binding of a human tear lipocalin mutein of the invention (S148.3 J14; SEQ ID NO:2) to IL-4 receptor alpha.
Figure 6:
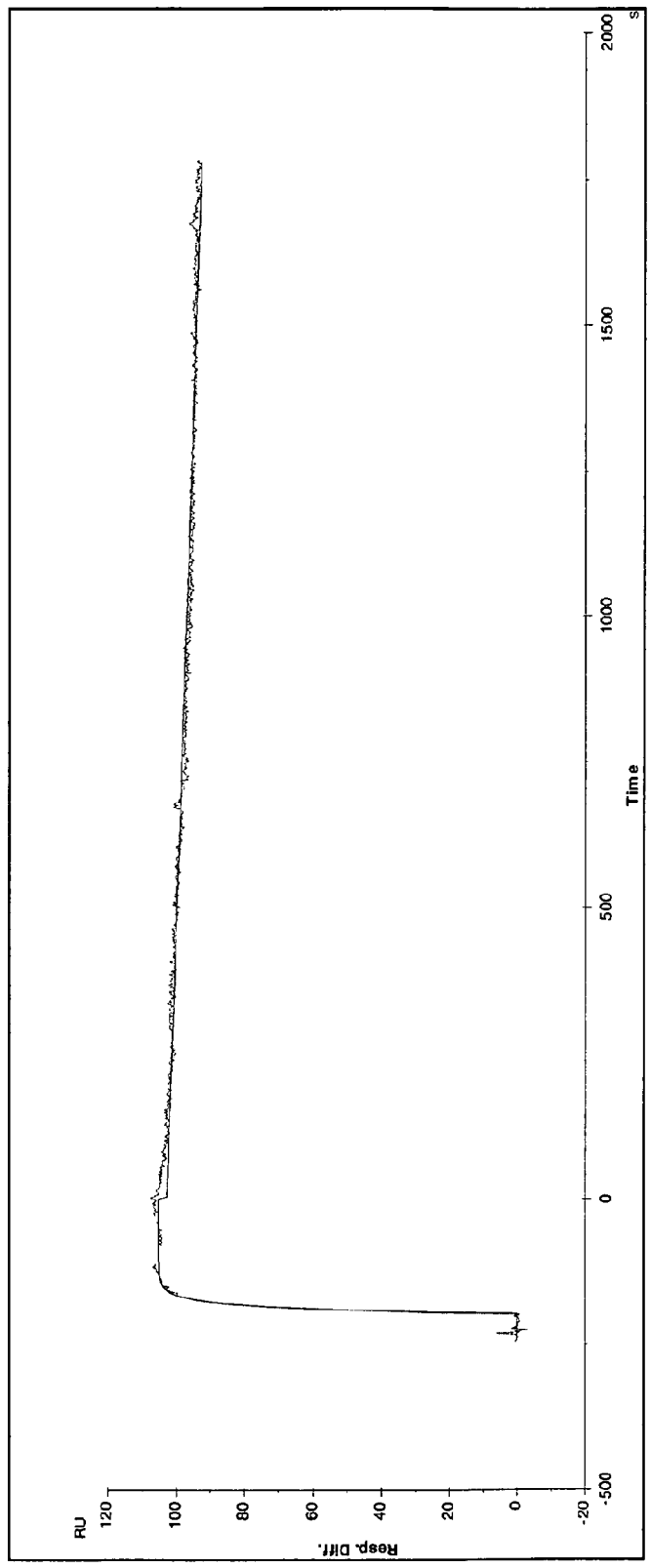
FIG. 6 shows BIAcore measurements of the binding of a human tear lipocalin mutein of the invention (S191.5 K12; SEQ ID NO:3) to IL-4 receptor alpha.
Figure 7:
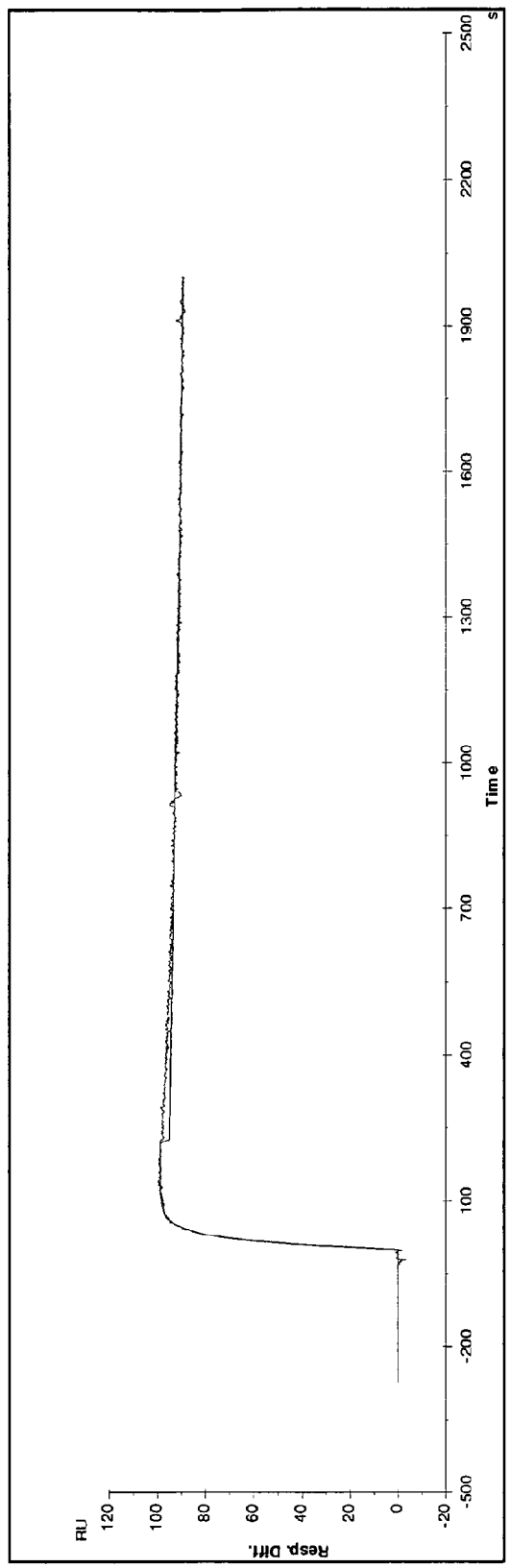
FIG. 7 shows BIAcore measurements of the binding of a human tear lipocalin mutein of the invention (S148.3 J14AM2C2; SEQ ID NO:4) to IL-4 receptor alpha.
Figure 8:
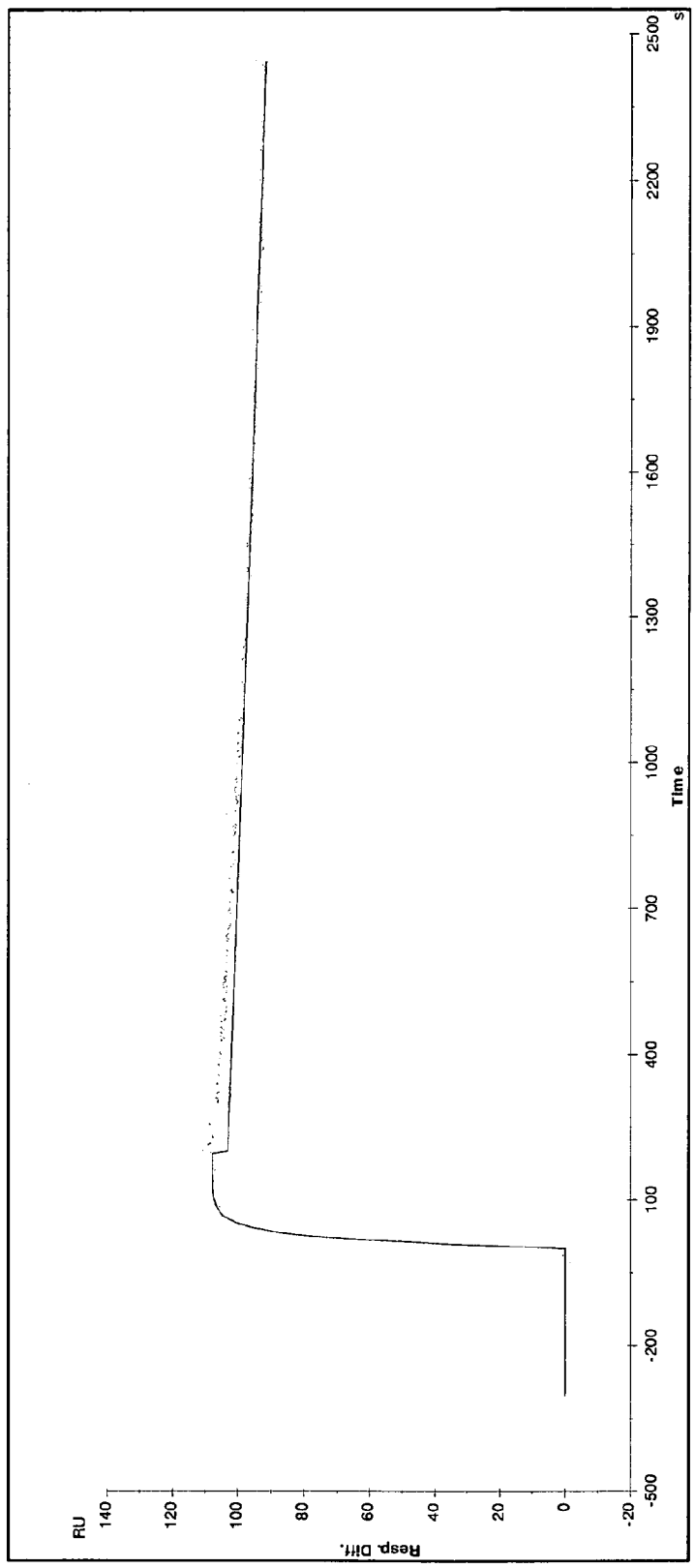
FIG. 8 shows BIAcore measurements of the binding of a human tear lipocalin mutein of the invention (S191.4 B24; SEQ ID NO:5) to IL-4 receptor alpha.
Figure 9:
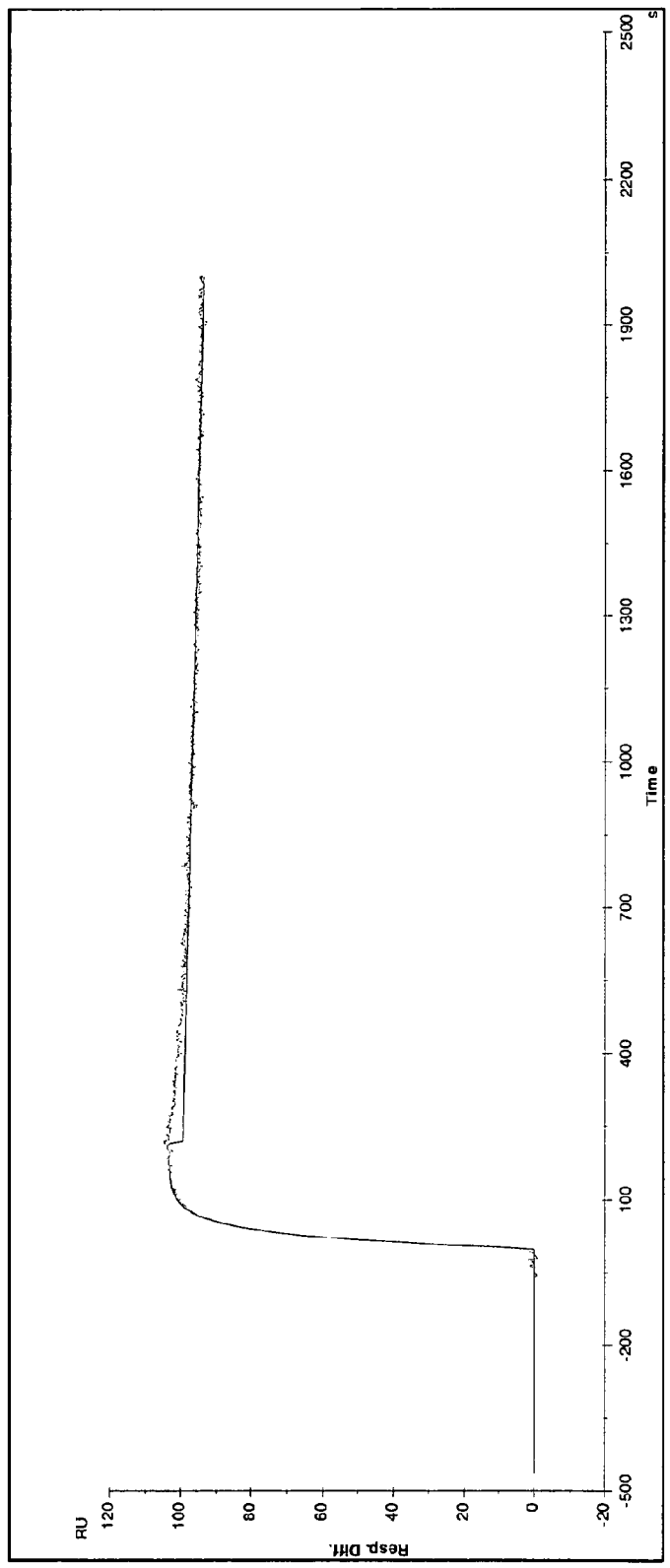
FIG. 9 shows BIAcore measurements of the binding of a human tear lipocalin mutein of the invention (S191.4 K19; SEQ ID NO:6) to IL-4 receptor alpha.
Figure 10:
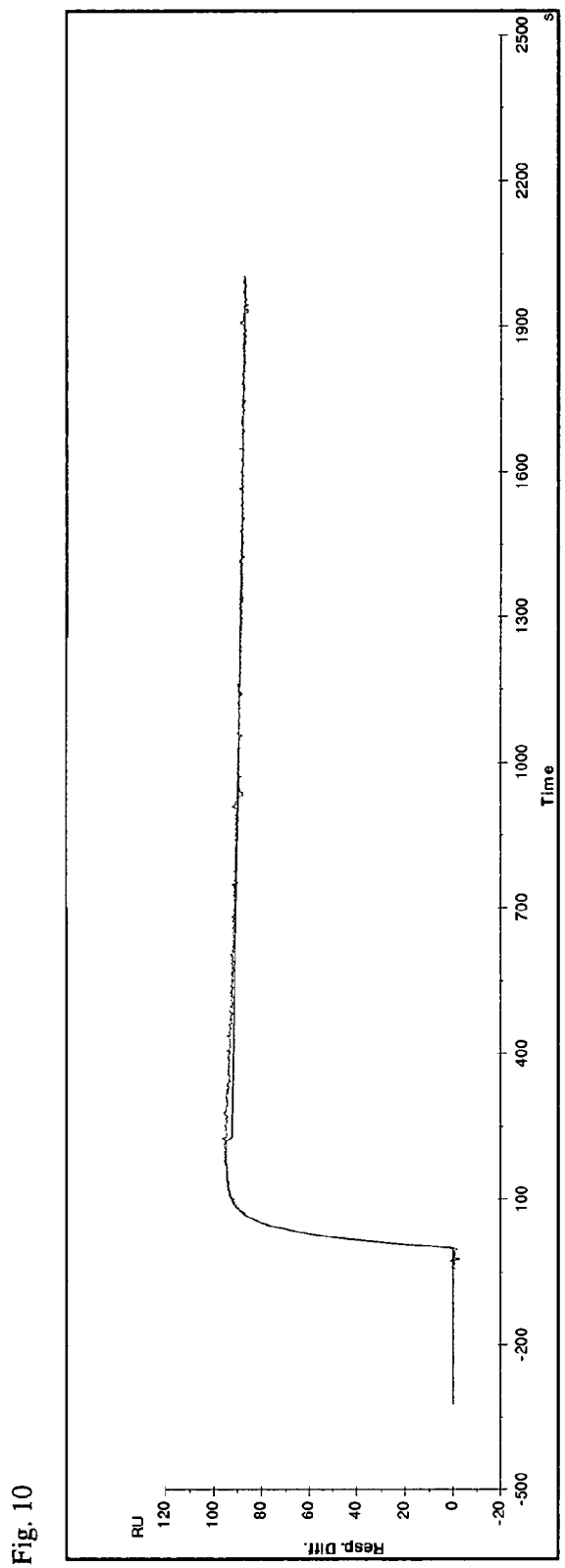
FIG. 10 shows BIAcore measurements of the binding of a human tear lipocalin mutein of the invention (S191.5H16; SEQ ID NO:7) to IL-4 receptor alpha.
Figure 11:
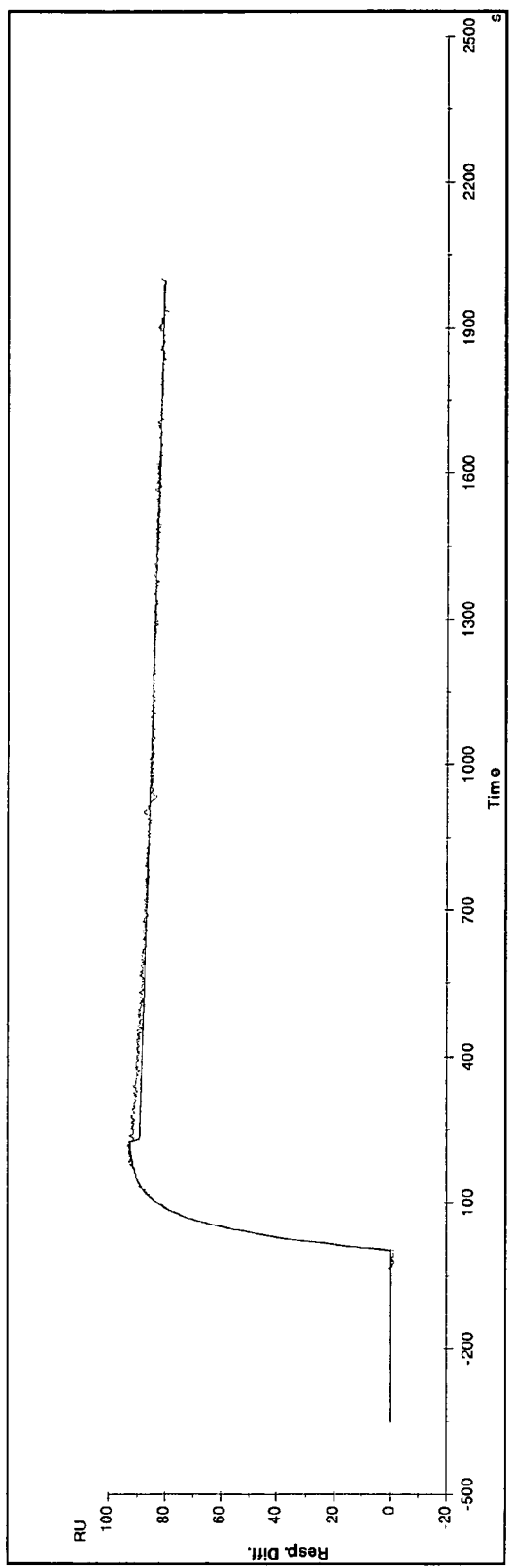
FIG. 11 shows BIAcore measurements of the binding of a human tear lipocalin mutein of the invention (S197.8 D22; SEQ ID NO:8) to IL-4 receptor alpha.
Figure 12:
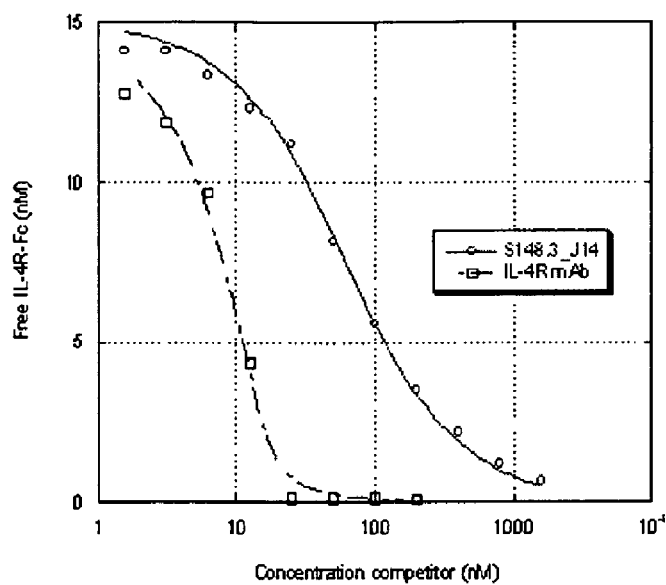
FIG. 12 shows competition ELISA measurements of the binding of a human tear lipocalin mutein of the invention (S148.3 J14; SEQ ID NO:2) to IL-4 receptor alpha.
Figure 13:
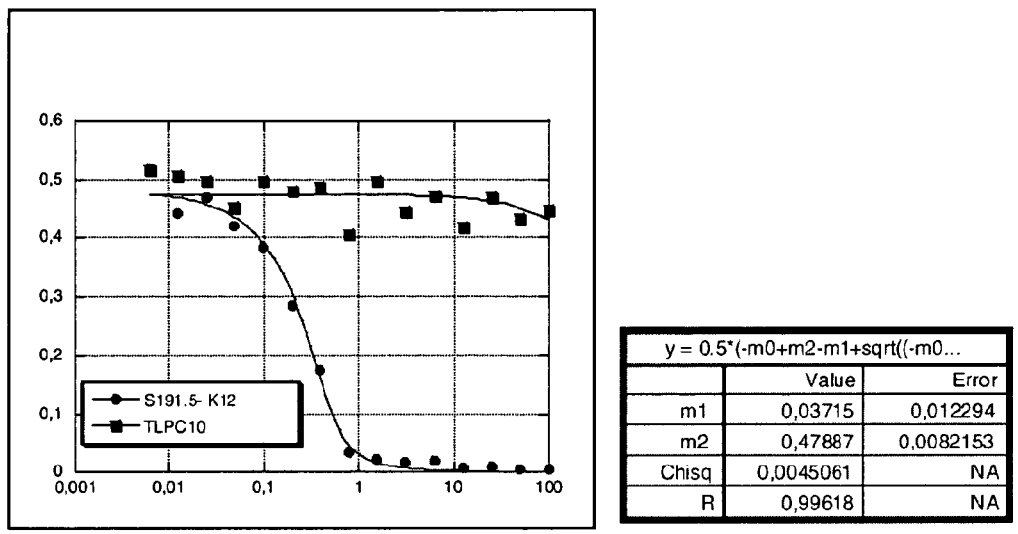
FIG. 13 shows competition ELISA measurements of the binding of a human tear lipocalin mutein of the invention (S191.5 K12; SEQ ID NO:3) to IL-4-receptor alpha.
Figure 14:
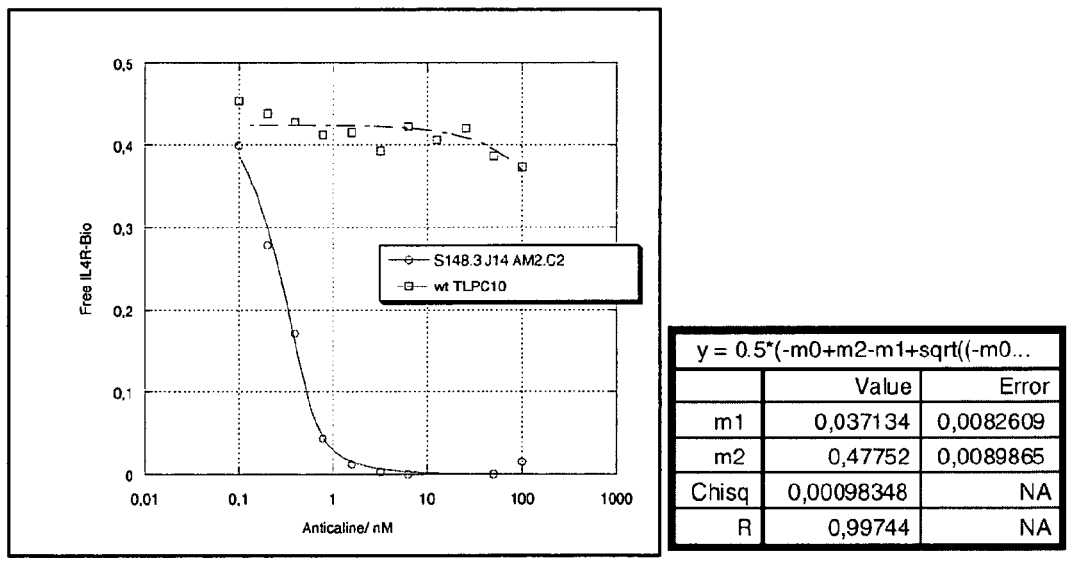
FIG. 14 shows competition ELISA measurements of the binding of a human tear lipocalin mutein of the invention (S148.3 J14AM2C2; SEQ ID NO:4) to IL-4 receptor alpha.
Figure 15:
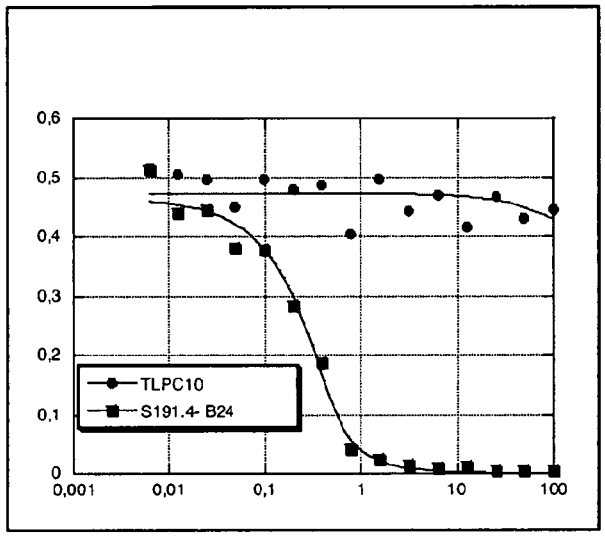
FIG. 15 shows competition ELISA measurements of the binding of a human tear lipocalin mutein of the invention (S191.4 B24; SEQ ID NO:5) to IL-4 receptor alpha.
Figure 16:
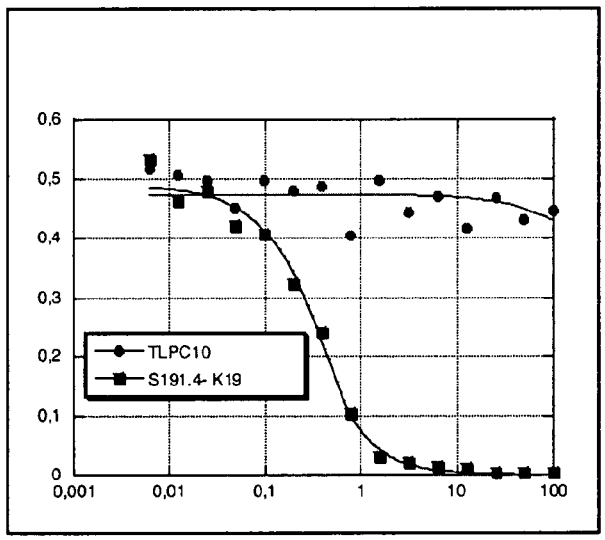
FIG. 16 shows competition ELISA measurements of the binding of a human tear lipocalin mutein of the invention (S191.4 K19; SEQ ID NO:6) to IL-4-receptor alpha.
Figure 17:
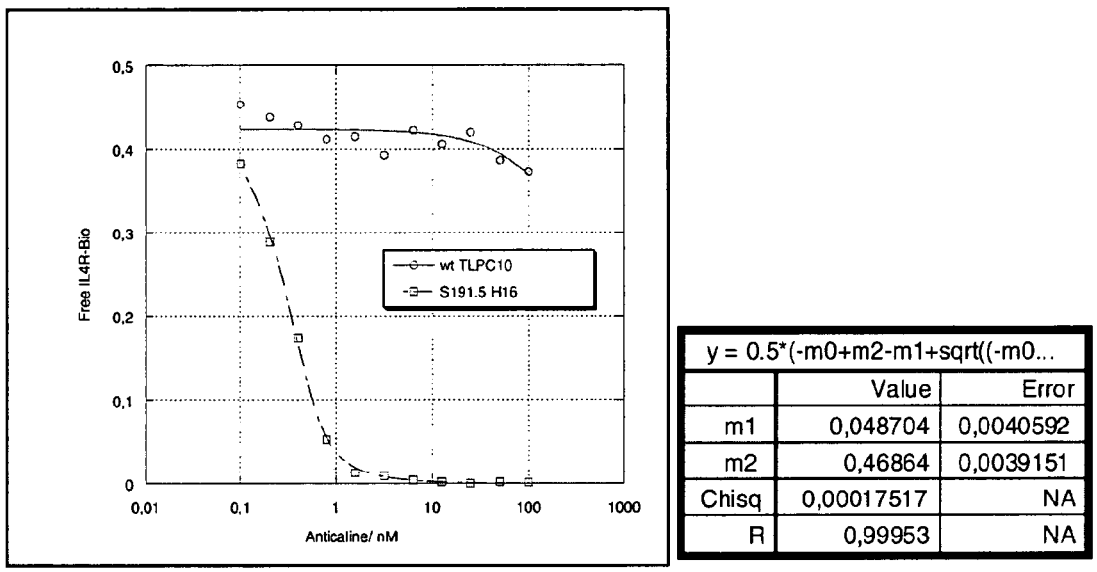
FIG. 17 shows competition ELISA measurements of the binding of a human tear lipocalin mutein of the invention (S191.5H16; SEQ ID NO:7) to IL-4-receptor alpha.
Figure 18:
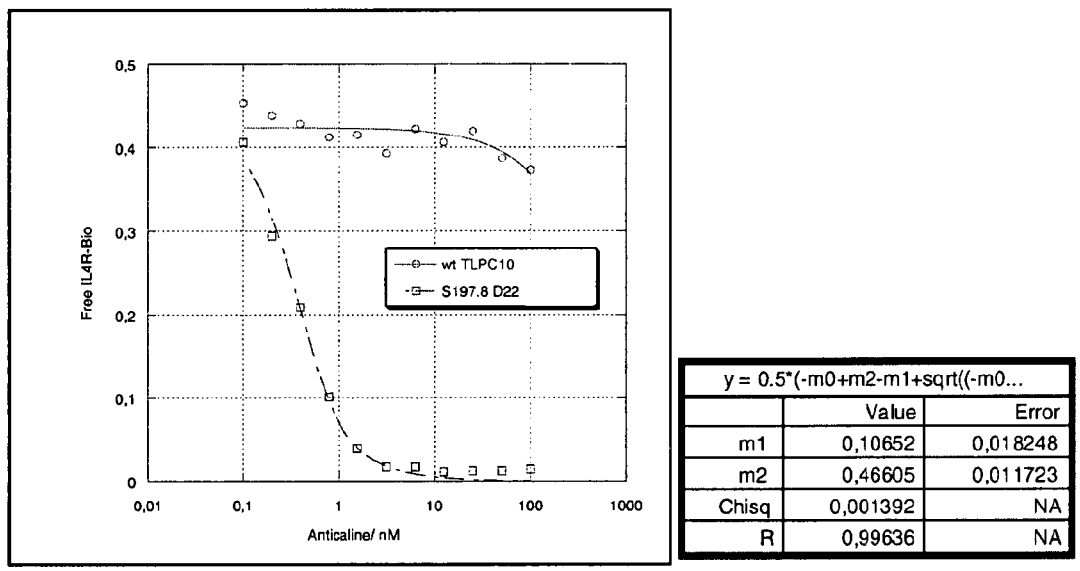
FIG. 18 shows competition ELISA measurements of the binding of a human tear lipocalin mutein of the invention (S197.8 D22; SEQ ID NO:8) to IL-4 receptor alpha

Unless otherwise indicated, established methods of recombinant gene technology were used, for example, as described in Sambrook et al. (*supra*).

Example 1

Generation of a Library with 2×10$^9$ Independent TLC Muteins

A random library of tear lipocalin (Tlc) with high complexity was prepared by concerted mutagenesis of the 18 selected amino acid positions 26, 27, 28, 29, 30, 31, 32, 33, 34, 56, 57, 58, 80, 83, 104, 105, 106, and 108 of the mature wild type human tear lipocalin. To this end, a gene cassette wherein the corresponding codons were randomized in a targeted fashion was assembled via polymerase chain reaction (PCR) with degenerate primer oligodeoxynucleotides in two steps according to a strategy described before (Skerra, A. (2001) "Anticalins": a new class of engineered-ligand-binding proteins with antibody-like properties. *J. Biotechnol.* 74, 257-275). In this library design the first 4 N-terminal amino acid residues (HHLA) as well as the two last C-terminal amino acid residues (SD) of the wild type sequence of tear lipocalin were deleted (for this reason, all tear lipocalin muteins shown in the attached Sequence Listing have Ala5 of the wild type sequence as N-terminal residue and Gly156 as C-terminal residue (the latter optionally fused to an affinity tag, for example)).

In the first step of the generation of the random library, a PCR fragment with randomized codons for the first and second exposed loop of Tlc was prepared using primers TL46 (SEQ ID NO: 10) and TL47 (SEQ ID NO:11) while another PCR fragment with randomized codons for the third and fourth exposed loop of Tlc was prepared in parallel, using primers TL48 (SEQ ID NO:12) and TL49 (SEQ ID NO:13). In the second step these two PCR fragments were combined with a connecting oligodeoxynucleotide and used as templates in a PCR reaction with primers AN-14 (SEQ ID NO:14), TL50 bio (SEQ ID NO:15) and TL51 bio (SEQ ID NO:16) to yield the assembled randomized gene cassette.

The two PCR reactions (1a and 1b) for the first step were each performed in a volume of 100 μl using 10 ng pTLPC10 plasmid DNA (FIG. 1) for each reaction as template, together with 50 pmol of each pair of primers (TL46 and TL47, or TL48 and TL49, respectively), which were synthesized according to the conventional phosphoramidite method. In addition, the reaction mixture contained 10 µl 10×Taq reaction buffer (100 mM Tris/HCl pH 9.0, 500 mM KCl, 15 mM MgCl$_2$, 1% v/v Triton X-100) and 2 µl dNTP-Mix (10 mM dATP, dCTP, dGTP, dTTP). After bringing to volume with water, 5 u Taq DNA polymerase (5 u/µl, Promega) were added and 20 cycles of 1 minute at 94° C., 1 minute at 58° C. and 1.5 minutes at 72° C. were carried out in a programmable thermocycler with a heated lid (Eppendorf), followed by an incubation for 5 minutes at 60° C. for completion. The amplification products with the desired size of 135 bp and 133 bp, respectively, were isolated by preparative agarose gel electrophoresis using GTQ Agarose (Roth) and the Wizard DNA extraction kit (Promega).

For the second PCR step a 1000 µl mixture was prepared, wherein approximately 500 fmol of both fragments from PCR reactions 1a and 1b were used as templates in the presence of 500 pmol of each of the flanking primers TL50 bio (SEQ ID NO:15) and TL51 bio (SEQ ID NO:16) and 10 pmol of the mediating primer AN-14 (SEQ ID NO:14). Both flanking primers carried a biotin group at their 5'-ends, thus allowing the separation of the PCR product after BstXI cleavage from incompletely digested product via streptavidin-coated paramagnetic beads. In addition, the reaction mix contained 100 µl 10×Taq buffer, 20 µl dNTP-Mix (10 mM dATP, dCTP, dGTP, dTTP), 50 u Taq DNA polymerase (5 u/µl, Promega) and water to bring it to the final volume of 1000 µl. The mixture was divided into 100 µl aliquots and PCR was performed with 20 cycles of 1 minute at 94° C., 1 minute at 57° C., 1.5 minutes at 72° C., followed by a final incubation for 5 minutes at 60° C. The PCR product was purified using the E.Z.N.A. Cycle-Pure Kit (PeqLab).

For subsequent cloning, this fragment representing the central part of the library of Tlc muteins in nucleic acid form was first cut with the restriction enzyme BstXI (Promega) according to the instructions of the manufacturer and then purified by preparative agarose gel electrophoresis as described above, resulting in a double-stranded DNA-fragment of 301 base pairs in size.

DNA fragments not or incompletely digested were removed via their 5'-biotin tags using streptavidin-coated paramagnetic beads (Merck). To this end, 150 µl of the commercially available suspension of the streptavidin-coated paramagnetic particles (at a concentration of 10 mg/ml) was washed three times with 100 µl TE buffer (10 mM Tris/HCl pH 8.0, 1 mM EDTA). The particles were then drained with the help of a magnet and mixed with 70 pmol of the digested DNA fragment in 100 µl TE buffer for 15 minutes at room temperature. The paramagnetic particles were then collected at the wall of the Eppendorf vessel with the aid of a magnet and the supernatant containing the purified, fully digested DNA fragment was recovered for use in the following ligation reaction.

The vector pTLPC27 (FIG. 20) was cut with the restriction enzyme BstXI (Promega) according to the instructions of the manufacturer and the obtained large vector fragment was purified by preparative agarose gel electrophoresis as described above, resulting in a double-stranded DNA-fragment of 3772 base pairs in size representing the vector backbone.

For the ligation reaction, 40 pmol of the PCR fragment and 40 pmol of the vector fragment (pTLPC27) were incubated in the presence of 1074 Weiss Units of T4 DNA ligase (Promega) in a total volume of 10.76 ml (50 mM Tris/HCl pH 7.8, 10 mM MgCl$_2$, 10 mM DTT, 1 mM ATP, 50 µg/ml BSA) for 48 h at 16° C. The DNA in the ligation mixture was then precipitated 1.5 h by adding 267 µl yeast tRNA (10 mg/ml solution in H$_2$O (Roche)), 10.76 ml 5 M ammonium acetate, and 42.7 ml ethanol. After precipitation, the DNA pellet was washed with 70% EtOH and then dried. At the end the DNA was dissolved to a final concentration of 200 µg/ml in a total volume of 538 µl of water.

The preparation of electrocompetent bacterial cells of *E. coli* strain XL1-Blue (Bullock et al., supra) was carried out according to the methods described by Tung and Chow (*Trends Genet.* 11 (1995), 128-129) and by Hengen (*Trends Biochem. Sci.* 21 (1996), 75-76). 1 l LB medium (10 g/L Bacto Tryptone, 5 g/L Bacto Yeast Extract, 5 g/L NaCl, pH 7.5) was adjusted to an optical density at 600 nm of OD$_{600}$=0.08 by addition of an overnight culture of XL1-Blue and was incubated at 140 rpm and 26° C. in a 2 l Erlenmeyer flask. After reaching an OD$_{600}$=0.6, the culture was cooled for 30 minutes on ice and subsequently centrifuged for 15 minutes at 4000 g and 4° C. The cells were washed twice with 500 ml ice-cold 10% w/v glycerol and finally re-suspended in 2 ml of ice-cold GYT-medium (10% w/v glycerol, 0.125% w/v yeast extract, 0.25% w/v tryptone). The cells were then aliquoted (200 µl), shock-frozen in liquid nitrogen and stored at −80° C.

Electroporation was performed with a Micro Pulser system (BioRad) in conjunction with cuvettes from the same vendor (electrode distance 2 mm) at 4° C. Aliquots of 10 µl of the ligated DNA solution (containing 1 µg DNA) was mixed with 100 µl of the cell suspension, first incubated for 1 minute on ice, and then transferred to the pre-chilled cuvette. Electroporation was performed using parameters of 5 ms and 12.5 kV/cm field strength and the suspension was immediately afterwards diluted in 2 ml ice-cold SOC medium (20 g/L Bacto Tryptone, 5 g/L Bacto Yeast Extract, 10 mM NaCl, 2.5 mM KCl, pH 7.5, autoclaved, before electroporation 10 ml/L 1 M MgCl$_2$ and 1 M MgSO$_4$ with 20 ml/L 20% Glucose were added), followed by incubation for 60 min at 37° C. and 140 rpm. After that, the culture was diluted in 2 L 2×YT medium (16 g/L Bacto Tryptone, 10 g/L Bacto Yeast Extract, 5 g/L NaCl, pH 7.5) containing 100 µg/ml chloramphenicol (2 YT/Cam), resulting in an OD$_{550}$ of 0.26. The culture was incubated at 37° C. until the OD$_{550}$ had risen again by 0.6 units.

By employing a total of 107.6 µg ligated DNA in 54 electroporation runs, a total of about 2.0×10$^9$ transformants were obtained. The transformants were further used for the preparation of phagemids coding for the library of the Tlc muteins as fusion proteins.

For preparation of the phagemid library, 4 l of the culture from above were infected with 1.3×10$^{12}$ pfu VCS-M13 helper phage (Stratagene). After agitation at 37° C. for 45 min the incubation temperature was lowered to 26° C. After 10 min of temperature equilibration 25 µg/l anhydrotetracycline was added in order to induce gene expression for the fusion protein between the Tlc muteins and the phage coat protein. Phagemid production was allowed for 11 h at 26° C. After removal of the bacteria by centrifugation the phagemids were precipitated from the culture supernatant twice with 20% (w/v) polyethylene glycol 8000 (Fluka), 15% (w/v) NaCl and finally dissolved in PBS (4 mM KH$_2$PO$_4$, 16 mM Na$_2$HPO$_4$, 115 mM NaCl).

Example 2

Phagemid Presentation and Selection of Tlc Muteins with Affinity for IL-4 Receptor Alpha Phagemid display and selection was performed employing the phagemids obtained from Example 1 essentially as described in WO 2006/56464 Example 2 with the following modifications: The target protein (IL-4 receptor alpha, Peprotech) was employed at a concentration of 200 nM and was presented to the library as biotinylated protein with subsequent capture of the phage-target complex using streptavidin beads (Dynal). Alternatively, the target protein was employed as Fc-fusion protein (IL-4 receptor alpha-Fc, R&D Systems) at a concentration of 200 nM and subsequent capture of the phage-target complex using protein G beads (Dynal) and by immobilization of Fc-fusion protein on anti-human Fc capture antibody (Jackson Immuno Research) coated immunosticks (Nunc) according to the instructions of the manufacturer. Three or four rounds of selection were performed.

Example 3

Identification of IL-4 Receptor Alpha-Specific Muteins Using High-Throughput ELISA Screening Screening of the muteins selected according to Example 2 was performed essentially as described in Example 3 of WO 2006/56464 with the following modifications: Expression vector was pTLPC10 (FIG. 1). Target protein used was IL-4 receptor alpha-Fc (R&D Systems) and IL-4 receptor alpha (Peprotech) both at 2 µg/ml.

Screening 5632 clones, selected as described in Example 2, lead to the identification of 2294 primary hits indicating that successful isolation of muteins from the library had taken place. Using this approach the clone S148.3 J14 (SEQ ID NO:2) was identified. The sequence of S148.3 J14 is also depicted in FIG. 2.

Example 4

Affinity Maturation of the Mutein S148.3 J14 Using Error-Prone PCR

Generation of a library of variants based on the mutein S148.3 J14 (SEQ ID NO:2) was performed essentially as described in Example 5 of WO 2006/56464 using the oligonucleotides TL50 bio (SEQ ID NO:15) and TL51 bio (SEQ ID NO:16) resulting in a library with 3 substitutions per structural gene on average.

Phagemid selection was carried out as described in Example 2 but employing limited target concentration (2 nM, 0.5 nM and 0.1 nM of IL-4 receptor alpha, Peprotech Ltd), extended washing times together with an antagonistic monoclonal antibody against IL-4 receptor alpha (MAB230, R&D Systems; 1 hour washing time and 2 hours washing time) or short incubation times (30 seconds, 1 minute and 5 minutes). Three or four rounds of selection were performed.

Example 5

Affinity Maturation of the Mutein S148.3 J14 Using a Site-Directed Random Approach A library of variants based on the mutein S148.3 J14 (SEQ ID NO:2) was designed by randomization of the positions 34, 53, 55, 58, 61, 64 and 66 to allow for all 20 amino acids on these positions. The library was constructed essentially as described in Example 1 with the modification that the deoxynucleotides TL70 (SEQ ID NO:17), TL71 (SEQ ID NO:18) and TL72 (SEQ ID NO:19) were used instead of TL46, TL47, and AN-14, respectively.

Phagemid selection was carried out as described in Example 2 using limited target concentration (0.5 nM and 0.1 nM of IL-4 receptor alpha, Peprotech) combined with extended washing times together with a competitive monoclonal antibody against IL-4 receptor alpha (MAB230, R&D Systems; 1 hour washing) or short incubation times (10 minutes), respectively. Three or four rounds of selection were performed.

Example 6

Affinity Screening of IL-4 Receptor Alpha-Binding Muteins Using High-Throughput ELISA Screening Screening was performed as described in Example 3 with the modification that a concentration of 3 nM IL-4 receptor alpha-Fc (R&D Systems) was used and the additions that i) a monoclonal anti-Strep tag antibody (Qiagen) was coated onto the ELISA plate in order to capture the produced muteins and binding of IL-4 receptor alpha-Fc (R&D Systems, 3 nM and 0.75 nM) to the captured muteins of tear lipocalin was detected using a HRP (horseradish peroxidase)-conjugated polyclonal antibody against the Fc domain of IL-4 receptor alpha-Fc. Additionally in an alternative screening setup ii) IL-4 was coated onto the ELISA plate and IL-4 receptor alpha-Fc (R&D Systems, 3 nM) was incubated with the expressed muteins and binding of IL-4 receptor alpha-Fc with an unoccupied IL-4 binding site was detected using a HRP-conjugated polyclonal antibody against the Fc domain of IL-4 receptor alpha-Fc.

A result from such a screen is depicted in FIG. 3. A large number of muteins selected as described in Example 4 and 5 were identified having improved affinity for IL-4 receptor alpha as compared to the mutein S148.3 J14 (SEQ ID NO:2) which served as the basis for affinity maturation. Using this approach the muteins S191.5 K12, S191.4 B24, S191.4 K19, S191.5H16, S197.8 D22 and S148.3 J14AM2C2 (SEQ ID NOs.:3-8) were identified. The sequences of S191.5 K12, S191.4 B24, S191.4 K19, S191.5H16, S197.8 D22 and S148.3 J14AM2C2 are also depicted in FIG. 4.

Example 7

Production of IL-4 Receptor Alpha-Binding Muteins

For preparative production of IL-4 receptor alpha-specific muteins, E. coli K12 strain JM83 harbouring the respective mutein encoded on the expression vector pTLPC10 (FIG. 1) was grown in a 2 L shake flask culture in LB-Ampicillin medium according to the protocol described in Schlehuber, S. et al. (*J. Mol. Biol.* (2000), 297, 1105-1120). When larger amounts of protein were needed, the E. coli strain W3110 harbouring the respective expression vector was used for the periplasmatic production via bench top fermenter cultivation in a 1 l or 10 l vessel based on the protocol described in Schiweck, W., and Skerra, A. *Proteins* (1995) 23, 561-565).

The muteins were purified from the periplasmic fraction in a single step via streptavidin affinity chromatography using a column of appropriate bed volume according to the procedure described by Skerra, A. & Schmidt, T. G. M. (2000) (Use of the Strep-tag and streptavidin for detection and purification of recombinant proteins. *Methods Enzymol.* 326A, 271-304). To achieve higher purity and to remove any aggregated recombinant protein, a gel filtration the muteins was finally carried out on a Superdex 75 HR 10/30 column (24-ml bed volume, Amersham Pharmacia Biotech) in the presence of PBS buffer. The monomeric protein fractions were pooled, checked for purity by SDS-PAGE, and used for further biochemical characterization.

Example 8

Affinity Measurement Using Biacore

Affinity measurements were performed essentially as described in Example 9 of WO 2006/56464 with the modifications that approximately 400 RU of IL-4 receptor alpha-Fc (R&D Systems) was immobilized (instead of 2000 RU of human CTLA-4 or murine CTLA-4-Fc used as target in WO 2006/56464) and 100 µl of mutein was injected at a concentration of 25 nM (instead of 40 µl sample purified lipocalin muteins at concentrations of 5-0.3 µM as used in WO 2006/56464).

Results from the affinity measurements employing S148.3 J14, S191.5 K12, S191.4 B24, S191.4 K19, S191.5H16, S197.8 D22 and S148.3 J14AM2C2 are depicted in FIGS. 5-11 and are summarized in Table I.

TABLE I

Affinities of selected muteins of the invention for IL-4 receptor alpha as determined by Biacore. Averages (standard deviation) of five experiments are shown.

| Clone | Affinity Biacore (pM) | $k_{on}$ (1/Ms × 10$^5$) | $k_{off}$ (1/s × 10$^{-5}$) |
|---|---|---|---|
| S148.3 J14 | 37500 | 1.4 | 517 |
| S191.5 K12 | 13.5 (2.9) | 58 (27) | 7.7 (3.3) |
| S148.3 AM2C2 | 17.9 (2.7) | 23 (1.7) | 4.2 (0.7) |
| S191.4 B24 | 19.3 (3.3) | 26 (6.7) | 4.9 (1.0) |
| S191.4 K19 | 20.1 (14) | 17 (2.7) | 3.6 (2.8) |
| S191.5 H16 | 24.3 (12) | 17 (1.8) | 4.1 (1.6) |
| S197.8 D22 | 55.8 (4.2) | 11 (1.3) | 6.3 (1.0) |

Example 9

Identification of Antagonists of IL-4 Using an Inhibition ELISA

Inhibition of the interaction between IL-4 and IL-4 receptor alpha by the selected muteins was evaluated in an inhibition ELISA. Therefore, a constant concentration of IL-4 receptor alpha (0.5 nM biotinylated IL-4 receptor alpha, Peprotech, or 15 nM IL-4 receptor alpha-Fc, R&D Systems) was incubated with a dilution series of tear lipocalin mutein and the amount of IL-4 receptor alpha with an unoccupied IL-4 binding site was quantified in an ELISA where the plate had been coated with IL-4 or an antagonistic anti IL-4 receptor alpha monoclonal antibody. Bound biotinylated IL-4 receptor alpha was detected using HRP-conjugated Extravidin (Sigma) and compared to a standard curve of defined amounts of biotinylated IL-4 receptor alpha. Results from measurements employing the muteins of S148.3 J14, S191.5 K12, S191.4 B24, S191.4 K19, S191.5H16, S197.8 D22 and S148.3 J14AM2C2 are depicted in FIGS. 12-18 and are summarized in Table II.

TABLE II

Antagonistic ability and affinities for IL-4 receptor alpha of selected tear lipocalin muteins of the invention as determined by competition ELISA. Averages (standard deviation) of three experiments are shown.

| Clone | Affinity Competition ELISA (pM) |
|---|---|
| S148.3 J14 | 17300 |
| S191.5 K12 | 25.3 (9.9) |
| S148.3 AM2C2 | 40.7 (14.8) |
| S191.4 B24 | 49.2 (14) |
| S191.4 K19 | 120 (32) |
| S191.5 H16 | 61.7 (11.4) |
| S197.8 D22 | 140 (37) |

Example 10

Identification of Antagonists of IL-4 and IL-13 Signalling Using a TF-1 Proliferation Assay IL-4 and IL-13-stimulated TF-1 cell proliferation assays were performed essentially as described in Lefort et al. (Lefort S., Vita N., Reeb R., Caput D., Ferrara P. (1995) FEBS Lett. 366(2-3), 122-126). The results from a TF-1 proliferation assay is depicted in FIG. 19 and shows that the high affinity variants S191.5 K12, S191.4 B24, S191.4 K19, S191.5H16, S197.8 D22 and S148.3 J14AM2C2 are potent antagonists of IL-4 as well as IL-13 induced signalling and proliferation.

Example 11

Anti-IL-4 Receptor Alpha Muteins of Human Tear Lipocalin Inhibit the STAT6 Mediated Pathway TF-1 cells were cultured in RPMI 1640 containing 10% heat-inactivated fetal calf serum, 2 mM L-glutamine, 100 Units/ml penicillin, 100 µg/ml streptomycin and supplemented with 2 ng/ml recombinant human granulocyte-macrophage colony-stimulating factor. The cells were seeded at 5×10$^4$ cells/ml in a total volume of 20 ml medium in 100 mm diameter tissue culture dishes, split and reseeded at this concentration every 2 to 3 days and cultured at 37° C. in a humidified atmosphere of 5% $CO_2$.

TF-1 cells were harvested by centrifugation at 1200 rpm for 5 min and washed twice by centrifugation at 1200 rpm for 5 min in RPMI 1640 containing 1% heat-inactivated fetal calf serum, 2 mM L-glutamine, 100 Units/ml penicillin and 100 µg/ml streptomycin (RPMI-1% FCS). Cells were resuspended at 1×10$^6$ cells/ml in RPMI-1% FCS, plated out at 1 ml in 24 well plates and cultured overnight. On the following day, TF-1 cells were cultured for 1 hr with 20 µg/ml of IL-4 receptor alpha-specific muteins or with negative control muteins. Further aliquots of cells were cultured with medium alone for 1 hr at 37° C. in a humidified atmosphere of 5% $CO_2$ in air. Subsequently, human recombinant IL-4 or IL-13 was added at a final concentration of 0.8 ng/ml or 12 ng/ml respectively and the cultures were incubated for 10 min at 37° C. in a humidified atmosphere of 5% $CO_2$ in air.

Cells were fixed for 10 min at room temperature (RT) by the addition of 42 µl of 37% formaldehyde (1.5% final concentration) and transferred to 5 ml round bottomed polystyrene tubes (BD Falcon). Cells were washed with 2 ml PBS containing 1% FCS (PBS-FCS), pelleted by centrifugation at 1200 rpm for 5 min and the supernatant was discarded. Cells were permeabilized by the addition of 500 µl ice-cold methanol whilst vortexing vigorously. After 10 min incubation at 4° C. the cells were washed twice by centrifugation at 1200 rpm for 5 min with 2 ml of PBS-FCS. The cells were resuspended in 100 µl of PBS-FCS and stained with 20 µl of anti-phosphorylated STAT-6 phycoerythrin (PE)-labelled antibody (clone Y641; BD Biosciences) for 30 min at RT protected from light. Finally, the cells were washed twice with 2 ml of PBS-FCS by centrifugation at 1200 rpm for 5 min and resuspended in 500 µl of PBS-FCS. The cells were analyzed by flow cytometry using a FACScalibur cytometer (BD Biosciences). Data were collected from at least 10000 gated cells.

The ability of the IL-4 receptor alpha-specific muteins S191.4 B24 (SEQ ID NO:5) and S191.4 K19 (SEQ ID NO:6) to inhibit IL-4 and IL-13 mediated STAT-6 phosphorylation in TF-1 cells was measured by flow cytometry. A gate was set on intact cells to exclude 99% of the control unstained population on the basis of FL2 values (channel 2 fluorescence; PE intensity) using control TF-1 cells (unstimulated and unstained) on the basis of cell size (forward scatter; FSC) and cell granularity (side scatter; SSC). A further aliquot of unstimulated cells was stained with anti-phosphorylated STAT-6 PE-labelled antibody.

Results of the STAT-6 phosphorylation assay clearly show that the IL-4 receptor alpha-specific muteins S191.4 B24 and S191.4 K19 markedly inhibit IL-4 and IL-13 induced STAT-6 phosphorylation in TF-1 cells (data summarized in Table III).

TABLE III

Ability of S191.4 B24 and S191.4 K19 (SEQ ID NO: 5 and 6) to inhibit STAT-6-phosphorylation-induced in TF-cells by IL-4 and IL-13 was measured by flow cytometry. The percentage of gated cells staining positive for STAT-6 phosphorylation and the median fluorescence intensity (MFI) of all gated cells are depicted.

| Treatment | % Positive | MFI |
|---|---|---|
| Unstained | 1 | 3.8 |
| Stained unstimulated | 6 | 5.8 |
| IL-4 | 75 | 15.8 |
| IL-13 | 77 | 16.4 |
| pTLPC10 + IL-4 (neg control) | 72 | 13.1 |
| pTLPC10 + IL-13 (neg control) | 84 | 18.6 |
| S191.4 K19 + IL-4 | 6 | 4.9 |
| S191.4 K19 + IL-13 | 8 | 5.0 |
| S191.4 B24 + IL-4 | 6 | 4.8 |
| S191.4 B24 + IL-13 | 11 | 5.5 |

Example 12

Anti-Human IL-4 Receptor Alpha Muteins are Cross-Reactive Against Cynomolgus Peripheral Blood Lymphocytes Whole blood from healthy human volunteers was collected by the clinical pharmacology unit (CPU) at Astra Zeneca (Macclesfield, UK) in 9 ml lithium-heparin tubes. Samples of heparinized whole blood from cynomolgus (pooled from a minimum of two animals) were obtained from Harlan Sera-Lab (Bicester, UK) or B and K Universal Ltd (Hull, UK).

Human and cynomolgus whole blood was diluted 1:5 with erythrocyte lysis buffer (0.15 M $NH_4Cl$, 1.0 mM $KHCO_3$, 0.1 mM EDTA, pH 7.2-7.4) and following inversion incubated at room temperature for 10 min. Cells were centrifuged at 1200 rpm for 5 min and supernatant removed. Cells were resuspended in lysis buffer and the procedure repeated until the supernatant no longer contained hemoglobin. Cells were re-suspended in the same volume of freezing medium (1:10, dimethyl sulfoxide: fetal calf serum) as the original volume of blood and transferred to cryogenic vials. Each vial contained the cells from 1 ml of blood. Cells were frozen overnight at −80° C. and transferred to liquid nitrogen for storage.

Frozen peripheral blood cells were rapidly thawed at 37° C. and washed with FACS buffer (PBS/1% FCS). Cell pellets were re-suspended in FACS buffer (1 ml buffer/vial). 100 µl aliquots were placed into 96 well round-bottomed plates, 100 µl of FACS buffer added per well, the plates centrifuged at 1200 rpm for 5 min at 4° C. and the supernatant discarded. Subsequently, cells were resuspended by vortexing at low speed and 100 µl of diluted primary antibody (anti-CD124 or IgG1 isotype control, eBioscience, 10 µg/ml) or anti-IL-4 receptor alpha muteins (10 µg/ml) were added and cells were incubated on ice for 30 min. Cells were washed once by the addition of 100 µl FACS buffer and centrifugation at 1200 rpm for 5 min at 4° C., the supernatant was discarded and the cells were resuspended by vortexing at low speed. This was repeated twice more using 200 µl of FACS buffer to wash cells. After the final centrifugation the cell pellet was re-suspended in 100 µl of the appropriate secondary antibody at 5 µg/ml (biotinylated anti-human lipocalin-1 antibody (R&D Systems) or biotinylated rat anti-mouse IgG (Insight Biotechnology Ltd)) and cells were incubated on ice for 30 min. Cells were washed once in 100 µl of FACS buffer by centrifugation at 1200 rpm for 5 min at 4° C., the supernatant discarded and cells resuspended by vortexing at low speed. Two further washes were performed using 200 µl of FACS buffer and centrifugation at 1200 rpm for 5 min at 4° C. After the final centrifugation the cell pellet was re-suspended in 100 µl of the detection reagent (phycoerthyrin [PE]-labelled streptavidin (eBioscience); 1.25 µg/ml) and incubated for 30 min on ice in the dark. After three further wash steps as before, the cells were taken up in 200 µl FACS buffer, transferred into 40×6 mm test tubes and analyzed by flow cytometry using a FACScalibur cytometer. Control cells were unstained. Using the unstained control cells, an intact lymphocyte cell gate was set on cell size (forward scatter; FSC) and cell granularity (side scatter; SSC) (Chrest, F. J. et al. (1993). Identification and quantification of apoptotic cells following anti-CD3 activation of murine G0 T cells. *Cytometry* 14: 883-90). This region was unaltered between samples analyzed on the same day. A marker was drawn to discriminate between IL-4 receptor alpha$^+$ and IL-4 receptor alpha$^-$ populations, based on FL2 (channel 2 fluorescence; PE intensity) values in the control unstained population; marker 1 (M1) IL-4R$\alpha^+$ cells was set on the basis of exclusion of 99% of the unstained population. For each sample, data from at least $1 \times 10^4$ cells were acquired.

Muteins S191.5 K12, S.148.3 J14-AM2C2, S.191.4 B24, S.191.4 K19, and S.197.8 D22 (SEQ ID NOs: 3-6 and 8) displayed high levels of binding to cynomolgus lymphocytes, IL-4 receptor alpha$^+$ cells varied between 61% and 80% and MFI values varied between 6.0 and 9.2 (Table 2). Variant S.191.5 H16 (SEQ ID NO:7) also specifically binds to cynomolgus lymphocytes but with reduced affinity compared to the remaining muteins (41% IL-4 receptor alpha$^+$ cells; MFI values 4.1).

In parallel, the ability of these IL-4 receptor alpha-specific muteins to bind to peripheral blood lymphocytes from one human donor was also analyzed by flow cytometry. All anti-IL-4 receptor alpha muteins exhibited considerably higher levels of binding to human cells than those observed for the pTLPC10 negative control. IL-4 receptor alpha$^+$ cells varied between 60% and 76% and MFI values varied between 7.4 and 9.7. Cells stained with pTLPC10 negative control displayed low levels of nonspecific binding, with 9% cells recorded as IL-4 receptor alpha$^+$ with MFI values of 3.2. Muteins S191.5 K12, S.191.4 B24, and S.191.4 K19 (SEQ ID NOs: 3, 5 and 6) displayed similar binding affinity to peripheral blood lymphocyte of a second human donor (data not shown).

TABLE IV

Ability of IL-4 receptor alpha-specific muteins to bind human and cynomolgus peripheral blood lymphocytes, analyzed by flow cytometry. The percentage of gated cells staining positive for IL-4 receptor alpha and the median fluorescence intensity (MFI) of all gated cells are shown.

| Treatment | Human peripheral blood cells | | Cynomolgus peripheral blood cells | |
|---|---|---|---|---|
| | % Positive | MFI | % Positive | MFI |
| Unstained | 1 | 2.4 | 1 | 1.7 |
| pTLPC10 (neg control) | 9 | 3.2 | 5 | 1.9 |
| S.191.4 K19 | 72 | 8.9 | 65 | 6.6 |
| S.191.5 K12 | 74 | 9.7 | 78 | 9.0 |
| S.191.4 B24 | 74 | 9.3 | 80 | 9.2 |
| S.148.3 J14-AM2C2 | 76 | 9.6 | 68 | 6.8 |
| S.191.5 H16 | 72 | 9.0 | 42 | 4.1 |
| S.197.8 D22 | 72 | 9.3 | 70 | 7.1 |

Example 13

Phagemid Presentation and Selection of Tlc Muteins with Affinity for Human VEGF

Phagemid display and selection employing the phagemids obtained from Example 1 was performed essentially as described in Example 2 with the following modifications: The target protein, i.e. a recombinant fragment of human VEGF-A (VEGF$_{8-109}$, amino acids 8-109 of the mature polypeptide chain) was employed at a concentration of 200 nM and was presented to the phagemid library as biotinylated protein with subsequent capture of the phage-target complex using streptavidin beads (Dynal) according to the instructions of the manufacturer. Four rounds of selection were performed.

The target protein was obtained by introducing the nucleic acids coding for amino acids 8 to 109 of the mature polypeptide chain of human VEGF A (SWISS PROT Data Bank Accession No. P15692) into the expression vector pET11c (Novagen). Therefore, BamHI and NdeI restriction sites were introduced at the 3' and the 5' end of the cDNA of the human VEGF fragment, respectively, and used for subcloning of the VEGF gene fragment.

E. coli BL21(DE3) was transformed with the resulting expression plasmid and cytoplasmic production of VEGF$_{8-109}$ was achieved after induction of an expression culture in ampicillin-containing LB medium with IPTG for 3 h at 37° C. After centrifugation at 5000 g for 20 min the cell pellet was resuspended in 200 ml PBS for each 2 l of culture broth and again centrifuged at 5000 g for 10 min prior to incubation at −20° C. over night. Each cell pellet obtained from 500 ml culture broth was resuspended in 20 ml 20 mM Tris-HCl (pH 7.5), 5 mM EDTA and sonificated on ice, four times for 10 seconds. After centrifugation for 10 min with 10000 g at 4° C., inclusion bodies were solubilized with 15 ml pre-chilled IB buffer (2 M urea, 20 mM Tris-HCl (pH 7.5), 0.5 M NaCl), sonificated and centrifuged as above. Afterwards, the cell pellets were solubilized with 20 ml IB buffer and again centrifuged like above prior to solubilization in 25 ml solubilization buffer (7.5 M urea, 20 mM Tris-HCl (pH 7.5), 4 mM DTT). The cell suspension was stirred for 2 h at ambient temperature, centrifuged at 40000 g for 15 min at 4° C. and the supernatant containing the recombinant VEGF was filtrated (0.45 µm). Refolding was achieved by dialysis (3.5 kDa molecular weight cut-off) at ambient temperature over night against 5 l buffer 1 (20 mM Tris-HCl (pH 8.4), 400 mM NaCl, 1 mM Cystein) followed by dialysis against 5 l buffer 2 (20 mM Tris-HCl (pH 8.4), 1 mM Cystein) and 2 subsequent dialysis steps with 5 l buffer 3 (20 mM Tris-HCl (pH 8.4)). After centrifugation (40000 g, 20 min, 4° C.) and concentration the recombinant VEGF fragment was purified according to standard methodologies by subsequent ion exchange chromatograpy (Q-Sepharose) and size exclusion chromatography (Superdex 75).

Example 14

Identification of VEGF-Binding Muteins Using a High-Throughput ELISA Screen

Screening of the Tlc muteins obtained in Example 13 was performed essentially as described in Example 3 with the modification that the recombinant target protein VEGF$_{8-109}$ obtained from Example 11 was employed at 5 µg/ml and was directly coated to the microtitre plate. Screening of altogether 2124 clones lead to the identification of 972 primary hits indicating that successful isolation of muteins from the library had taken place. Using this approach the Tlc mutein S168.4-L01 (SEQ ID NO:26) was identified.

Example 15

Affinity Maturation of Tlc Mutein S168.4-L01 Using Error-Prone PCR

Generation of a library of variants based on mutein S168.4-L01 was performed essentially as described in Example 4 using the oligonucleotides TL50 bio (SEQ ID NO:15) and TL51 bio (SEQ ID NO:16) resulting in a library with 5 substitutions per structural gene on average.

Phagemid selection was carried out as described in Example 13 using limited target concentration (10 nM, 1 nM and 0.2 nM VEGF$_{8-109}$), or short incubation times (1 and 5 minutes) with and without limiting target concentrations (10 nM, 100 nM). Four rounds of selection were performed.

Example 16

Affinity Screening of VEGF-Binding Muteins Using a High-Throughput ELISA Screen

Screening of the muteins selected in Example 15 was performed as described in Example 14 with the modification that a monoclonal anti-T7 tag antibody (Novagen) was coated onto the ELISA plate in order to capture the produced muteins and binding of biotinylated VEGF$_{8-109}$ (500 nM and 50 nM) to the captured Tlc muteins was detected using HRP-conjugated Extravidin.

A large number of clones were identified having improved affinity as compared to the mutein S168.4-L01, which served as the basis for affinity maturation. Using this approach clones S209.2-C23, S209.2-D16, S209.2-N9, S209.6-H7, S209.6-H10, S209.2-M17, S209.2-O10 (SEQ ID NOs:27-33) were identified.

Example 17

Production of VEGF Binding Muteins

Production was performed essentially as described in Example 7.

Example 18

Affinity Determination of VEGF-Specific Muteins Employing Biacore

Affinity measurements were performed essentially as described in Example 8 with the modification that approximately 250 RU of recombinant VEGF was directly coupled to the sensor chip using standard amine chemistry. 40 µl of the Tlc muteins obtained from Example 15 was injected at a concentration of 400 nM.

Results from the affinity determinations of the muteins S209.2-C23, S209.2-D16, S209.2-N9, S209.6-H7, S209.6H10, S209.2-M17 and S209.2-O10 (SEQ ID NOs:27-33) are summarized in Table V.

TABLE V

Affinities of selected muteins of the invention for VEGF as determined by Biacore measurements at 25° C.

| Clone | $k_{on}$ [$10^4$ 1/Ms] | $k_{off}$ [$10^{-5}$ 1/s] | Affinity [nM] |
|---|---|---|---|
| S209.2-C23 | 3.6 | 1.3 | 0.37 |
| S209.2-D16 | 3.8 | 3 | 0.79 |
| S209.2-N9 | 5.9 | 7.1 | 1.2 |
| S209.6-H7 | 6.4 | 4.4 | 0.68 |
| S209.6-H10 | 4.6 | 4.4 | 0.97 |
| S209.2-M17 | 2.8 | 2.0 | 0.72 |
| S209.2-O10 | 3.2 | 0.67 | 0.21 |

Example 19

Identification of Antagonists of VEGF Using an Inhibition ELISA

Inhibition of the interaction between VEGF and VEGF Receptor 2 (VEGF-R2) was evaluated in an inhibition ELISA. To this end, a constant concentration of biotinylated VEGF$_{8-109}$ (1 nM) was incubated with a dilution series of the respective Tlc mutein and the amount of VEGF with an unoccupied VEGF-R2 binding site was quantified in an ELISA where an anti-VEGF antibody interfering with the VEGF/VEGF-R2 interaction (MAB293, R&D Systems) had been coated. Bound VEGF was detected using HRP-conjugated Extravidin (Sigma) and compared to a standard curve of defined amounts of VEGF. Results from measurements employing muteins S209.2-C23, S209.2-D16, S209.2-N9, S209.6-H7, S209.6-H10, S209.2-M17 and S209.2-O10 (SEQ ID NOs:27-33) are summarized in Table VI.

TABLE VI

Antagonistic ability and affinities for VEGF of selected tear lipocalin muteins of the invention as determined by competition ELISA.

| Clone | Affinity Competition ELISA Ki [nM] |
|---|---|
| S209.2-C23 | 2.3 |
| S209.2-D16 | 3.9 |
| S209.2-N9 | 2.8 |
| S209.6-H7 | 2.4 |
| S209.6-H10 | 1.3 |
| S209.2-M17 | 2.0 |
| S209.2-O10 | 0.83 |

Example 20

Identification of VEGF Antagonists Using a HUVEC Proliferation Assay

Figure 21C:
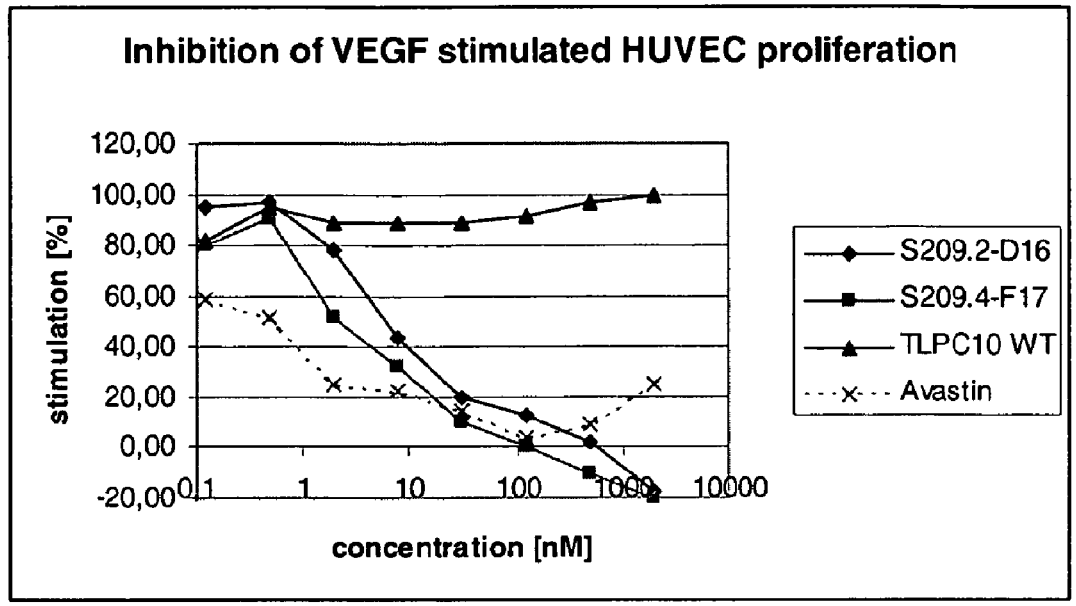
Figure 21D:
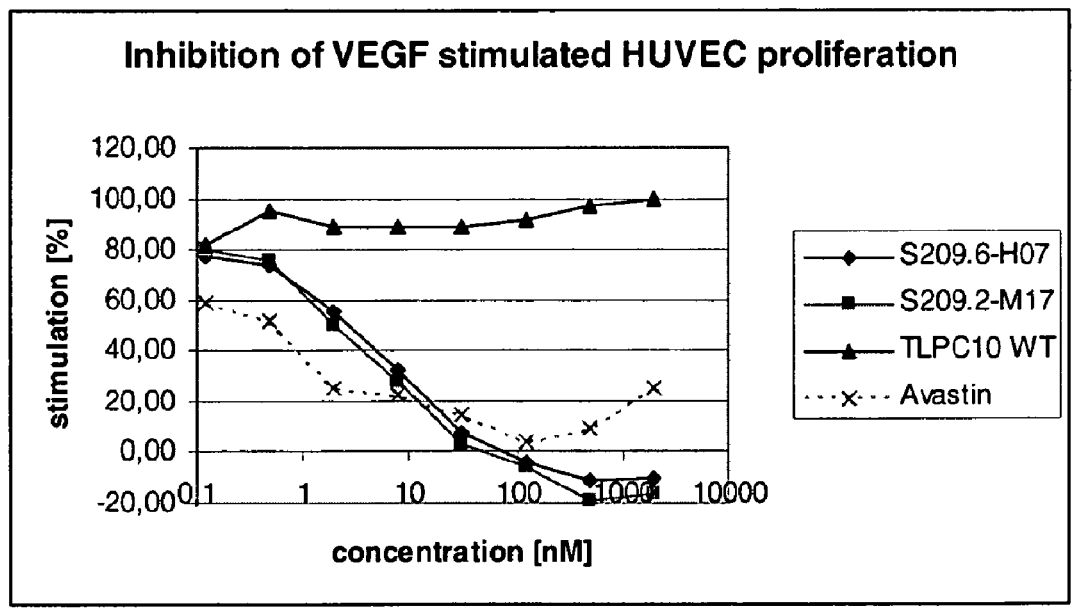

Inhibition of VEGF and FGF-2 stimulated HUVEC cell proliferation was assessed essentially as previously described (Korherr C., Gille H, Schafer R., Koenig-Hoffmann K., Dixelius J., Egland K. A., Pastan I. & Brinkmann U. (2006) *Proc. Natl. Acad. Sci.* (USA) 103 (11) 4240-4245) with the following modifications: HUVEC cells (Promocell) were grown according to the manufacturer's recommendations and used between passage 2 and 6. On day one, 1.400 cells were seeded in complete medium (Promocell). On the following day, cells were washed and basal medium containing 0.5% FCS, hydrocortisone and gentamycin/amphotericin but no other supplements (Promocell) was added. VEGF-specific mutein S209.2-C23, S209.2-D16, S209.2-N9, S209.6-H7, S209.6-H10, S209.2-M17, S209.2-O10 (SEQ ID NOs:27-33), wild-type tear lipocalin (gene product of pTLPC10; as control) or VEGF-specific therapeutic monoclonal antibody Avastin® (Roche; as control) was added in a dilution series at the indicated concentration in triplicate wells and after 30 min either human VEGF165 (R&D Systems) or human FGF-2 (Reliatech) was added. Viability of the cells was assessed after 6 days with CellTiter 96 Aqueous One (Promega) according to the manufacturer's instructions. Results from measurements employing muteins S209.2-C23, S209.2-D16, S209.2-N9, S209.6-H7, S209.6-H10, S209.2-M17 and S209.2-O10 (SEQ ID NOs:27-33) are shown in FIG. 21. All muteins of the invention show marked inhibition of VEGF-induced proliferation of HUVEC cells, which is comparable to or better than the Avastin®-induced inhibition, whereas wildtype tear lipocalin does not inhibit VEGF-induced cell proliferation. FGF-2-induced cell proliferation is not affected by any of the VEGF-specific muteins, TLPC10 or Avastin® (not shown).

Example 21

Phagemid Presentation and Selection of Tlc Muteins Against VEGF-R2

Phagemid display and selection employing the phagemids obtained from Example 1 was performed essentially as described in Example 2 with the following modifications: Target protein VEGF-R2-Fc (R&D Systems) was employed at a concentration of 200 nM and was presented to the library as Fc-fusion protein with subsequent capture of the phage-target complex using protein G beads (Dynal) according to the instructions of the manufacturer. Four rounds of selection were performed.

Example 22

Identification of VEGF-R2-Binding Muteins Using a High-Throughput ELISA Screen Screening was performed essentially as described in Example 3 with the modification that the target protein VEGF-R2-Fc (R&D Systems) was used at a concentration of 2.5 µg/ml.

Screening of 1416 clones, obtained from the procedure described under Example 21 lead to the identification of 593 primary hits indicating that successful isolation of muteins from the library of the invention had taken place. Using this approach the mutein S175.4 H11 (SEQ ID NO:34) was identified.

Example 23

Affinity Maturation of VEGF-R2-Specific Mutein S175.4 H11 Using Error-Prone PCR Generation of a library of variants based on the mutein S175.4 H11 was performed essentially as described in Example 4 using the oligodeoxynucleotides TL50 bio (SEQ ID NO:15) and TL51 bio (SEQ ID NO:16) resulting in a library with 2 substitutions per structural gene on average.

Phagemid selection was carried out as described in Example 21 using limited target concentration (5 nM, 1 nM and 0.2 nM of VEGF-R2-Fc), extended washing times (1 h) in the presence of competing recombinant $VEGF_{81-109}$ (100 nM) or short incubation times (2 and 5 minutes) with and without limiting target concentrations (10 nM, 100 nM). Four rounds of selection were performed.

Example 24

Affinity Screening of VEGF-R2-Binding Muteins Using a High-Throughput ELISA Screen Screening was performed as described in Example 3 with the modification that monoclonal anti-T7 tag antibody (Novagen) was coated onto the ELISA plate in order to capture the produced Tlc muteins and binding of VEGF-R2-Fc (R&D Systems, 3 nM and 1 nM) to the captured muteins was detected using a HRP-conjugated antibody against the Fc domain of VEGF-R2-Fc.

A large number of clones were identified having improved affinity compared to the muteins S175.4 H11, which served as the basis for affinity maturation. Using this approach the clones S197.7-N1, S197.2-I18, S197.2-L22, S197.7-B6 and S197.2-N24 (SEQ ID NOs:35-39) were identified.

Example 25

Production of VEGF-R2 Binding Muteins

Production was performed essentially as described in Example 7.

Example 26

Affinity Determination of VEGF-R2-Specific Muteins Using Biacore

Affinity measurements were performed essentially as described in Example 8 with the modifications that approximately 500 RU of VEGF-R2-Fc (R&D Systems) was captured and 80 µl of mutein was injected at a concentration of 1.5 µM.

Results from the measurements employing S175.4-H11, S197.7-N1, S197.2-I18, S197.2-L22, S197.7-B6 and S197.2-N24 (SEQ ID NOs:35-39) are summarized in Table VII.

TABLE VII

Affinities of selected muteins of the invention for VEGF-R2 as determined by Biacore measurements.

| Clone | $k_{on}$ [$10^4$ 1/Ms] | $k_{off}$ [$10^{-5}$ 1/s] | Affinity [nM] |
|---|---|---|---|
| S175.4-H11 | 0.9 | 36 | 35 |
| S197.7-N1 | 2.1 | 11 | 5.5 |
| S197.2-I18 | 2.7 | 8.3 | 3.1 |
| S197.2-L22 | 1.2 | 2.4 | 3.3 |
| S197.7-B6 | 2.3 | 13 | 6 |
| S197.2-N24 | 2.4 | 6.4 | 2.7 |

Example 27

Identification of Antagonists of VEGF Using an Inhibition ELISA

Inhibition of the interaction between VEGF and VEGF-R2 by the VEGF-R2-specific muteins was evaluated in an inhibition ELISA. Therefore, a constant concentration of VEGF-R2 (4 nM VEGF-R2-Fc, R&D Systems) was incubated with a dilution series of the respective mutein and the amount of VEGF-R2 with an unoccupied VEGF binding site was quantified in an ELISA where $VEGF_{8-109}$ had been coated. Bound VEGF-R2 was detected using HRP-conjugated anti-human Fc antibody (Dianova) and compared to a standard curve of defined amounts of VEGF-R2-Fc. Results from measurements of S175.4-H11, S197.7-N1, S197.2-I18, S197.2-L22, S197.7-B6 and S197.2-N24 (SEQ ID NOs:35-39) are summarized in Table VIII.

TABLE VIII

Antagonistic ability and affinities for VEGF-R2 of selected tear lipocalin muteins of the invention as determined by competition ELISA.

| Clone | Affinity competition ELISA Ki [nM] |
|---|---|
| S175.4-H11 | 12.9 |
| S197.7-N1 | 12 |
| S197.2-I18 | 5.5 |
| S197.2-L22 | 3.5 |
| S197.7-B6 | 3.8 |
| S197.2-N24 | 2.3 |

Example 28

Site-Specific Modification of IL-4 Receptor Alpha-Specific Muteins with Polyethylene Glycol (PEG)

An unpaired cysteine residue was introduced instead of the amino acid Glu at position 131 of the IL-4 receptor alpha-specific mutein S148.3 J14 (SEQ ID NO:2) by point mutation in order to provide a reactive group for coupling with activated PEG. The recombinant mutein carrying the free Cys residue was subsequently produced in E. coli as described in Example 7.

For coupling of the mutein S148.3 J14 with PEG, 5.1 mg polyethylene glycol maleimide (average molecular weight 20 kDa, linear carbon chain; NOF) was mixed with 3 mg of the protein in PBS and stirred for 3 h at ambient temperature. The reaction was stopped by the addition of beta-mercaptoethanol to a final concentration of 85 μM. After dialysis against 10 mM Tris-HCl (pH 7.4), the reaction mixture was applied to a HiTrap Q-XL Sepharose column (Amersham) and the flow-through was discarded. The PEGylated mutein was eluted and separated from unreacted protein applying a linear salt gradient from 0 mM to 100 mM NaCl.

Example 29

Affinity Measurement of the PEGylated Mutein S148.3 J14 Using Biacore

Figure 22:
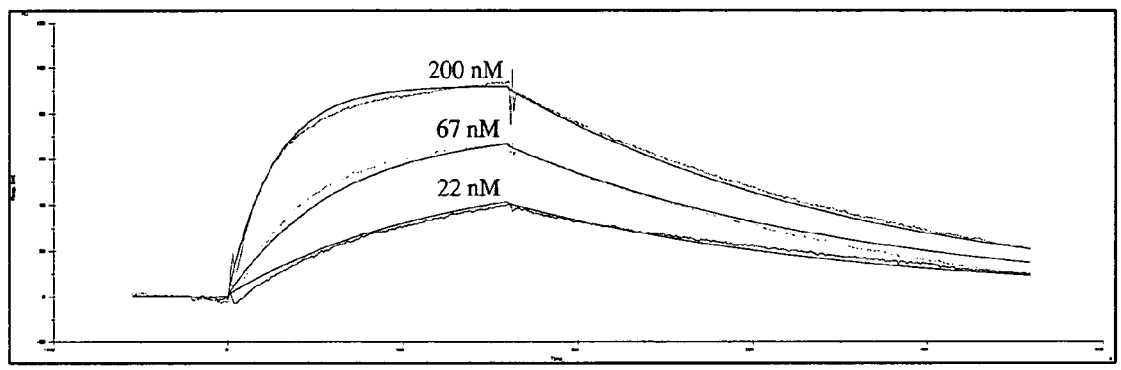
FIG. 22 shows BIAcore measurements of the binding of a PEGylated human tear lipocalin mutein of the invention (S148.3 J14; SEQ ID NO:2) to IL-4 receptor alpha.

Affinity measurements were performed essentially as described in Example 8 with the modifications that approximately 500 RU of IL-4 receptor alpha-Fc (R&D Systems) was immobilized and 80 μl of the purified PEGylated mutein was injected at concentrations of 200 nM, 67 nM and 22 nM. The result of the measurement is depicted in FIG. 22 and summarized in Table IX. The affinity of the mutein S148.3 J14 in its PEGylated form (ca. 30 nM) is almost unchanged as compared to the non-PEGylated mutein (ca. 37 nM, cf. Example 8).

TABLE IX

Affinity of the PEGylated mutein of the invention S148.3 J14 for IL-4 receptor alpha as determined by Biacore.

| Clone | $k_{on}$ [$10^5$ 1/Ms] | $k_{off}$ [$10^{-3}$ 1/s] | Affinity [nM] |
| --- | --- | --- | --- |
| S148.3 J14-PEG | 1.64 | 4.93 | 30 |

Example 30

Affinity Maturation of the Mutein S209.6-H10 Using a Site-Directed Random Approach A library of variants based on the mutein S209.6-H10 (SEQ ID NO:30) was designed by randomization of the residue positions 26, 69, 76, 87, 89 and 106 to allow for all 20 amino acids on these positions. The library was constructed essentially as described in Example 1 with the modification that the deoxynucleotides TL107 (covering position 26), TL109 (covering positions 87 and 89), TL110 (covering position 106) and TL111 (covering positions 69 and 76) were used instead of TL46, TL47, TL48 and TL49, respectively. Phagemid selection was carried out essentially as described in Example 13 using either limited target concentration (10 pM and 2 pM and 0.5 pM of VEGF$_{8-109}$) or combined with a competitive monoclonal antibody against VEGF (Avastin®). Four rounds of selection were performed.

TL107
(SEQ ID NO: 40)
GAAGGCCATGACGGTGGACNNSGGCGCGCTGAGGTGCCTC

TL109
(SEQ ID NO: 41)
GGCCATCGGGGGCATCCACGTGGCANNSATCNNSAGGTCGCACGTGAAGG
AC

TL110
(SEQ ID NO: 42)
CACCCCTGGGACCGGGACCCCSNNCAAGCAGCCCTCAGAG

TL111
(SEQ ID NO: 43)
CCCCCGATGGCCGTGTASNNCCCCGGCTCATCAGTTTTSNNCAGGACGGC
CCTCACCTC

Example 31

Affinity Screening of VEGF-Binding Muteins Using High-Throughput ELISA Screening Screening was performed as described in Example 14 with the modification that a concentration of 1 μg/ml VEGF was used and the additions that
i) a monoclonal anti-T7 tag antibody (Novagen) was coated onto the ELISA plate in order to capture the produced muteins and binding of biotinylated VEGF (3 nM and 1 nM) to the captured muteins of tear lipocalin was detected using a HRP (horseradish peroxidase)-conjugated extravidin. Additionally, in alternative screening setups
ii) instead of human VEGF$_{8-109}$ mouse VEGF$_{164}$ (R&D Systems) was directly coated to the microtiter plate (1 μg/ml).
iii) the extract containing the VEGF-binding muteins was heated to 60° C. for 1 hour.
iv) mAB293 (R&D Systems, 5 μg/ml) was coated onto the ELISA plate and biotinylated VEGF$_{8-109}$ was preincubated with the expressed muteins. Binding of VEGF$_{8-109}$ to mAB293 was detected using HRP (horseradish peroxidase)-conjugated extravidin.

A large number of clones were identified having improved affinity as compared to the mutein S209.6-H10, which served as the basis for affinity maturation. Using this approach clones S236.1-A22, S236.1-J20, S236.1-M11 and S236.1-L03 (SEQ ID NOs:44-47) were identified.

In this context it is noted that due to the deletion of the first 4 amino acids of tear lipocalin in the muteins of the invention, the amino acid sequence is depicted starting from sequence position 5 (alanine) of the deposited wild type tear lipocalin sequence of tear lipocalin, so that Ala5 is depicted as N-terminal amino acid. In addition, the C-terminal amino acid Asp158 of the wild type tear lipocalin is replaced by an alanine residue (residue 154 in SEQ ID NO: 44-47, see also the other muteins of the invention such as SEQ ID NO:26-40). Furthermore, the amino acid sequence of muteins S236.1-A22, S236.1-J20, S236.1-M11 and S236.1-L03 together with the STREP-TAG® II that is fused to the C-terminus of tear lipocalin for the construction of the naïve library of Example 1 is shown in SEQ ID NO:52 (S236.1-A22-strep), SEQ ID NO: 53 (S236.1-J20-strep), SEQ ID NO: 54 (S236.1-M11-strep) and SEQ ID NO: 55 (S236.1-L03-step). Also this illustrates the variability of the sequence of tear lipocalin muteins of the invention apart from the indicated mutated positions/mutations that are necessary to provide the respective mutein with the ability to specifically bind the given target such as VEGF, or VEGF-R2 or interleukin 4 receptor alpha chain (IL-4 receptor alpha).

Example 32

Production of VEGF Binding Muteins

Production was performed essentially as described in Example 7.

Example 33

Affinity Determination of VEGF-Specific Muteins Employing Biacore

Figure 23:
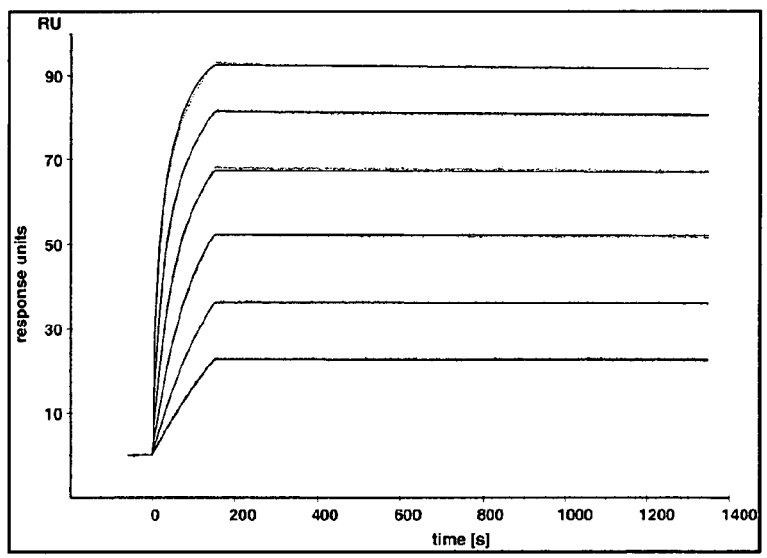
FIG. 23 shows BIAcore measurements of the binding of a human tear lipocalin mutein of the invention (S236.1-A22, SEQ ID NO:44) to immobilized $VEGF_{8-109}$.

Affinity measurements were performed essentially as described in Example 18. (See also FIG. 23 in which Biacore measurements of the binding of human tear lipocalin mutein S236.1-A22 (SEQ ID NO:44) to immobilized $VEGF_{8-109}$ are illustrated). Briefly, $VEGF_{8-109}$ was immobilized on a CM5 chip using standard amine chemistry. Lipocalin mutein was applied with a flow rate of 30 µl/min at six concentrations from 500 nM to 16 nM. Evaluation of sensorgrams was performed with BIA T100 software to determine Kon, Koff and KD of the respective muteins.

TABLE X

Affinities of selected muteins of the invention for VEGF as determined by Biacore measurements at 25° C.

| Mutein | $k_{on}$ [$10^4$ 1/Ms] | $k_{off}$ [$10^{-5}$ 1/s] | Affinity [nM] |
|---|---|---|---|
| S236.1-A22 | 8.8 | 2.2 | 0.25 |
| S236.1-J20 | 7.9 | 2.2 | 0.28 |
| S236.1-L03 | 6.8 | 4.4 | 0.64 |
| S236.1-M11 | 7.3 | 2.3 | 0.31 |

Example 34

Identification of Antagonists of VEGF Using an Inhibition ELISA

Inhibition of the interaction between VEGF and VEGF Receptor 2 (VEGF-R2) was evaluated in an inhibition ELISA essentially as described in Example 19 with the modification that the incubation time of 1 hour was reduced to 10 minutes. Inhibition constants are summarized in the following Table:

TABLE XI

Antagonistic ability and affinities for VEGF of selected tear lipocalin muteins of the invention as determined by competition ELISA.

| Mutein | Affinity Competition ELISA Ki [nM] |
|---|---|
| S236.1-A22 | 5.8 |
| S236.1-J20 | 6.3 |
| S236.1-L03 | 9.4 |
| S236.1-M11 | 6.4 |

Example 35

Determination of Cross-Reactivity of VEGF-Specific Muteins S236.1-A22 Using Biacore Affinity measurements were performed essentially as described in Example 18 with the modification that mutein S236.1-A22 (SEQ ID NO:44) was immobilized on the sensor chip. 70 µl of sample was injected at a concentration of 250 nM.

Figure 24:
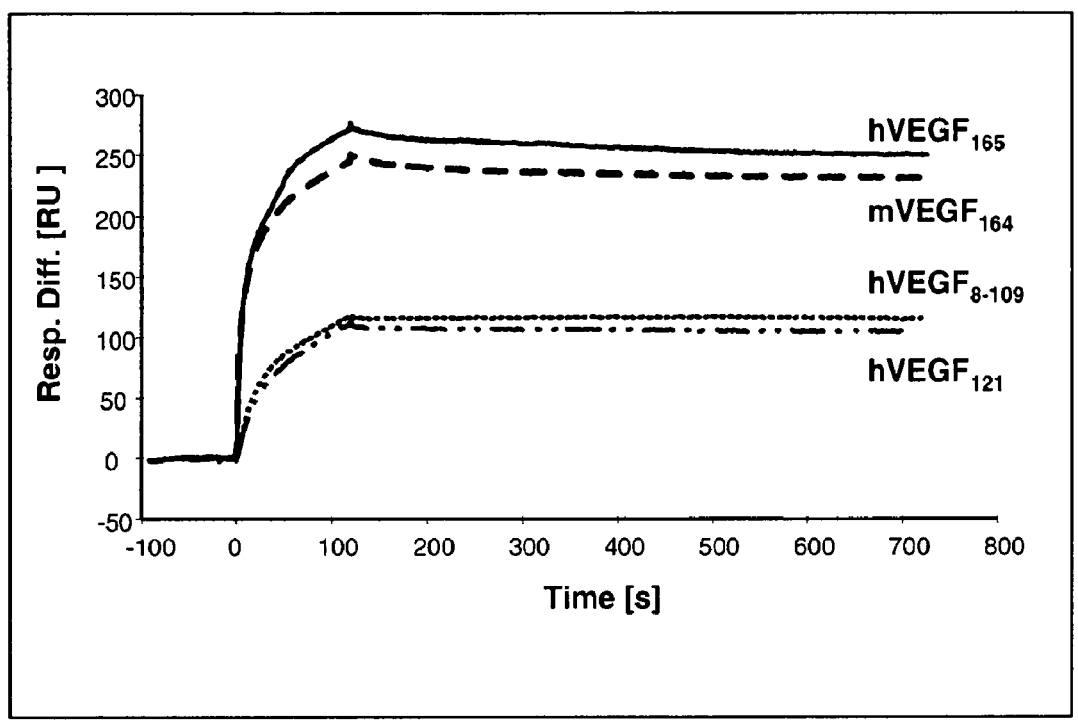
FIG. 24 shows BIAcore measurements of the binding of $hVEGF_{8-109}$, $hVEGF_{121}$, splice form $hVEGF_{165}$, and the respective mouse ortholog $mVEGF_{164}$ to the human tear lipocalin mutein S236.1-A22 (SEQ ID NO:44).

The qualitative comparison of the results as shown in FIG. 24 illustrate that the truncated form $hVEGF_{8-109}$ and $hVEGF_{121}$ show basically identical sensorgrams indicating similar affinity to the tear lipocalin mutein S236.1-A22 (SEQ ID NO:44). The splice form $hVEGF_{165}$ also shows strong binding to the lipocalin mutein, while the respective mouse ortholog mVEGF164 has slightly reduced affinity. Isoforms VEGF-B, VEGF-C and VEGF-D and the related protein P1GF show no binding in this experiment (data not shown).

Example 36

Determination of Thermal Denaturation for VEGF-Binding Muteins by Use of CD Spectroscopy Circular dichroism measurements were performed essentially as described in Example 14 of the International patent application WO2006/056464, with the modification that the wavelength used was 228 nM. The melting temperature $T_m$ of the tear lipocalin mutein S236.1-A22 (SEQ ID NO:44) for example was determined to be 75° C.

Example 37

Stability Test of S236.1-A22

Stability of VEGF-binding mutein S236.1-A22 at 37° C. in PBS and human serum was tested essentially as described in Example 15 of the International patent application WO2006/056464 except that the concentration utilized was 1 mg/ml. No alteration of the mutein could be detected during the seven day incubation period in PBS as judged by HPLC-SEC (data not shown). Incubation of the lipocalin mutein in human serum resulted in a drop of affinity after 7 days to approx. 70% compared to the reference (See also FIG. 25a).

Example 38

Fusion of Anti-VEGF Muteins with an Albumin-Binding Domain

Figure 26:
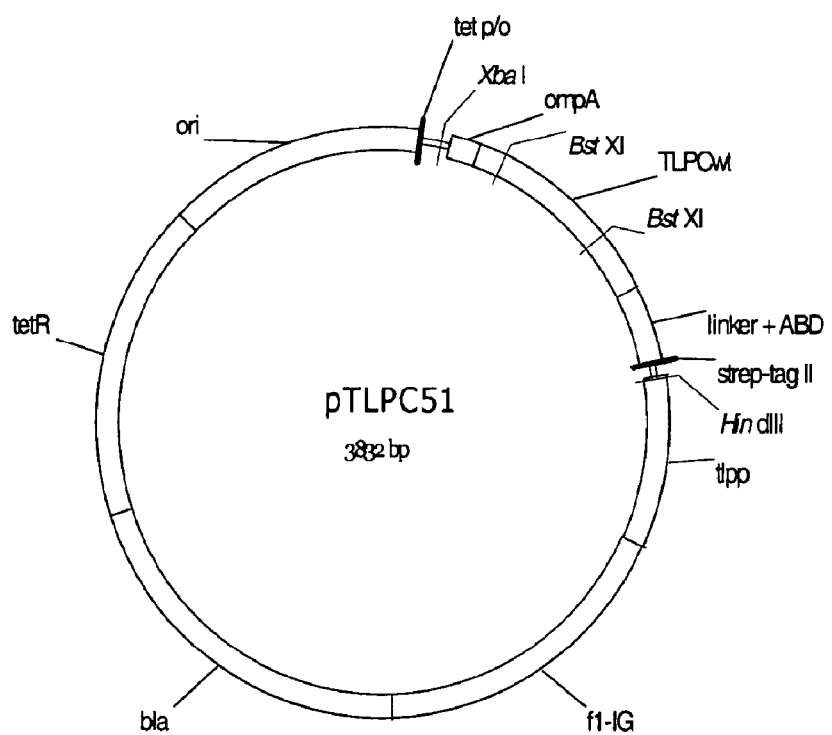
FIG. 26 shows the expression vector pTLPC51 which encodes a fusion protein comprising the OmpA signal sequence (OmpA), a mutated human tear lipocalin (Tlc) fused to an albumin-binding domain (abd), followed by a Strep-tag II.

For serum half-life extension purposes anti-VEGF muteins were C-terminally fused with an albumin-binding domain (ABD). The genetic construct used for expression is termed pTLPC51_S236.1-A22 (SEQ ID NO:50). (See FIG. 26)

The preparative production of VEGF-specific mutein-ABD fusions or Tlc-ABD (as control) was performed essentially as described in Example 7.

Figure 27:
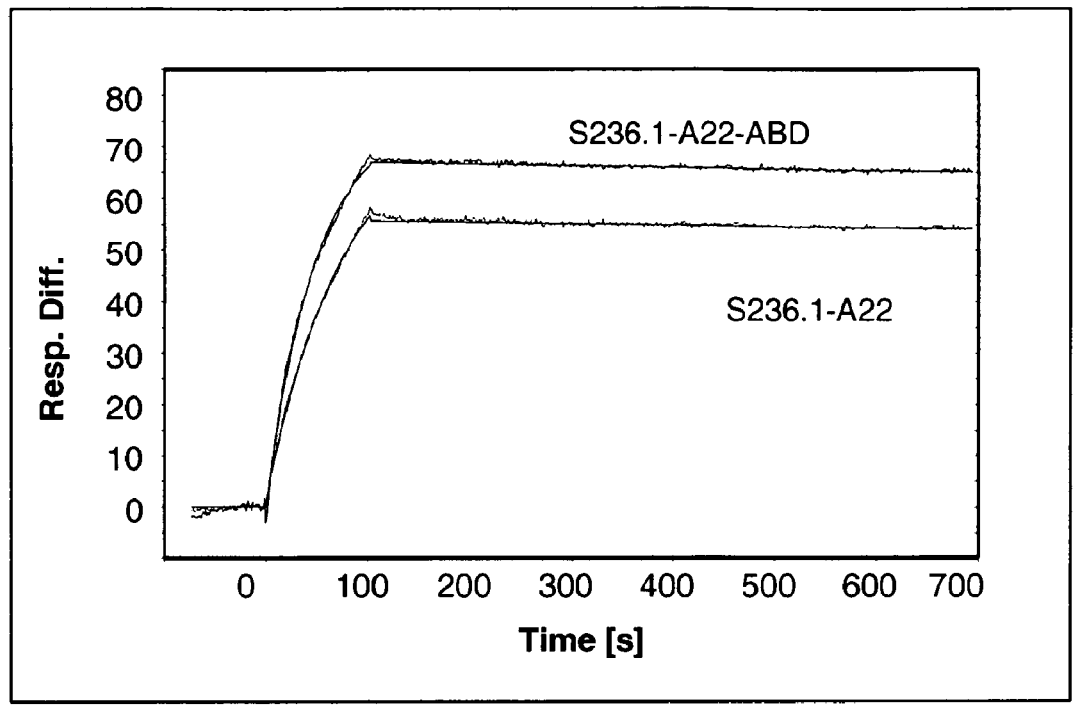
FIG. 27 shows BIAcore measurements of the binding of tear lipocalin mutein S236.1-A22 (SEQ ID NO:44) and a fusion protein of mutein S236.1-A22 with ABD (SEQ ID NO:51) to recombinant VEGF.

Affinity measurements using surface plasmon resonance (Biacore) were performed essentially as described in Example 18. The affinity of the ABD-fusion of tear lipocalin mutein S236.1-A22 (A22-ABD) (SEQ ID NO: 51) (200 pM) towards recombinant VEGF was found basically unaltered and measured to be 260 pM (see FIG. 27).

Additionally, the integrity of the ABD-domain was tested by the same method, as described in Example 8, with the modification that approximately 850 RU of human serum albumin was directly coupled to the sensor chip using standard amine chemistry. 60 µl of mutein-ABD fusions (A22-ABD (SEQ ID NO: 51) or wildtype Tlc-ABD (SEQ ID NO:49)) were injected at a concentration of 500 nM. Their affinity was measured to be approx. 20 nM The stability of the ABD-fusion of S236.1-A22 (SEQ ID NO: 51) in human serum was tested essentially as described in Example 37. No loss of activity could be detected during the seven day incubation period. (See FIG. 25b)

Figure 28:
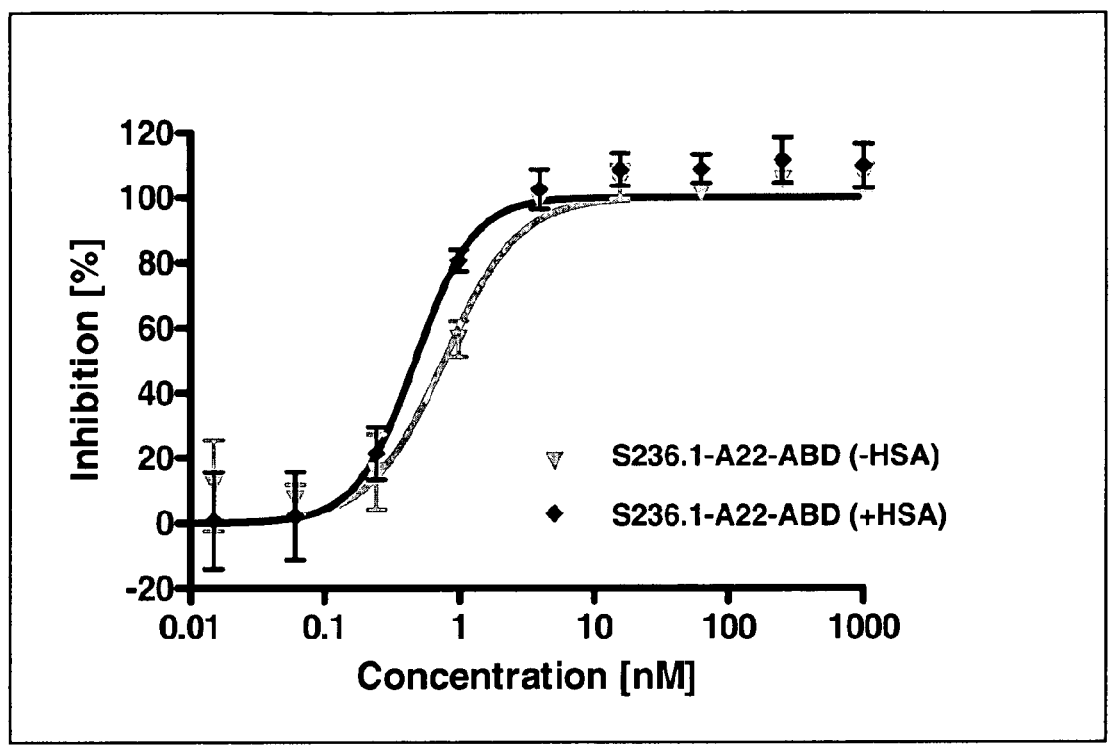
FIG. 28 shows the inhibition of VEGF induced HUVEC proliferation by S236.1-A22 with ABD (SEQ ID NO:51) in the absence or presence of human serum albumin (HSA).

The functionality of the lipocalin mutein A22-ABD (ABD-fusion of S236.1-A22) in the presence of human serum albumin was tested by its ability to inhibit VEGF induced HUVEC proliferation. The assay was performed as described in Example 39 except that human serum albumin (HSA, 5 µM) was added where indicated. At 5 µM HSA, >99.8% of A22-ABD is associated with HSA at any given time due to the nanomolar affinity of A22-ABD for HSA (see FIG. 28). IC50 values were determined to be as follows:

| | |
|---|---|
| S236.1-A22-ABD | IC50: 760 pM |
| S236.1-A22-ABD (+HSA) | IC50: 470 pM |

Example 39

Inhibition of VEGF Induced HUVEC Proliferation

Figure 29:
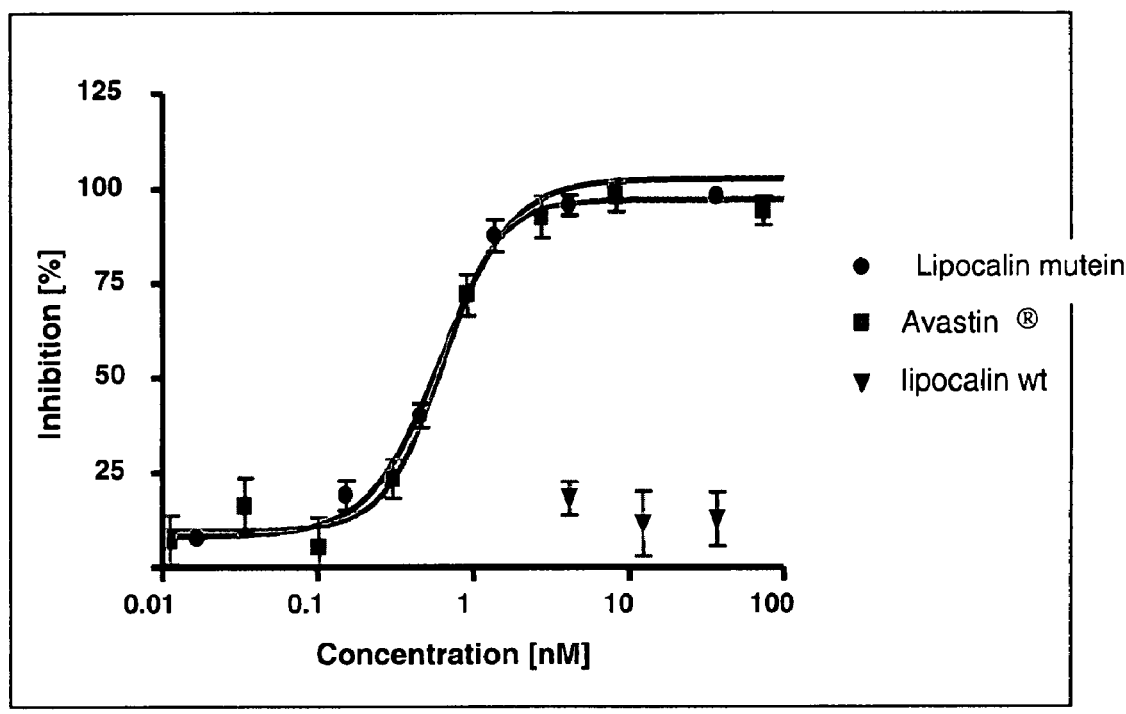
FIG. 29 shows the inhibition of VEGF induced proliferation of endothelial cells cultured from human umbilical vein (HUVEC) by the lipocalin mutein S236.1-A22 (SEQ ID NO:44) compared to the inhibition achieved by Avastin® and wildtype tear lipocalin.

HUVEC (Promocell) were propagated on gelatine-coated dishes and used between passages P2 and P8. On day 1, 1400 cells were seeded per well in a 96 well plate in complete medium. On day 2, cells were washed and 100 µl of basal medium containing 0.5% FCS, hydrocortisone and gentamycin/amphotericin was added. Proliferation was stimulated with 20 ng/ml VEGF165 or 10 ng/ml FGF-2 which were mixed with the lipocalin mutein S236.1-A22 (SEQ ID NO:44), incubated for 30 min and added to the wells. Viability was determined on day 6, the results are expressed as % inhibition. IC50 values were determined to be as follows (see also FIG. 29).

| | |
|---|---|
| S236.1-A22 | IC50: 0.51 nM |
| Avastin | IC50: 0.56 nM |

FGF-2 mediated stimulation was unaffected by VEGF antagonists (data not shown).

Example 40

Inhibition of VEGF-Mediated MAP Kinase Activation in HUVEC

Figure 30:
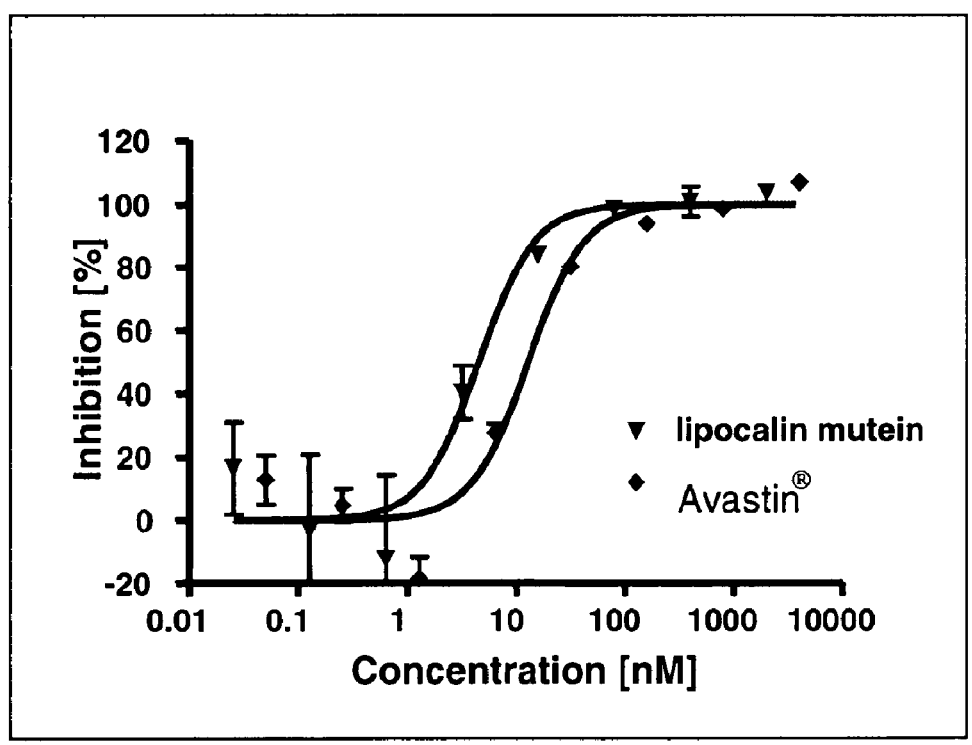
FIG. 30 shows the inhibition of VEGF mediated MAP kinase activation in HUVEC by the lipocalin mutein S236.1-A22 (SEQ ID NO:44) compared to the inhibition achieved by Avastin®.

HUVEC were seeded in 96-well plates at 1,400 cells per well in standard medium (Promocell, Heidelberg). On the following day, FCS was reduced to 0.5% and cultivation was continued for 16 h. Cells were then starved in 0.5% BSA in basal medium for 5 h. HUVEC were stimulated with $VEGF_{165}$ (Reliatech, Braunschweig) for 10 min in the presence of increasing concentrations of tear lipocalin mutein A22 or Avastin (bevacizumab, Genentech/Roche) in order to obtain a dose-response curve. Phosphorylation of the MAP kinases ERK1 and ERK2 was quantified using an ELISA according to the manufacturer's manual (Active Motif, Rixensart, Belgium). The IC 50 value was determined to be 4.5 nM for the mutein A22 (SEQ ID NO:44) and 13 nM for Avastin® (see FIG. 30).

Example 41

Figure 31:
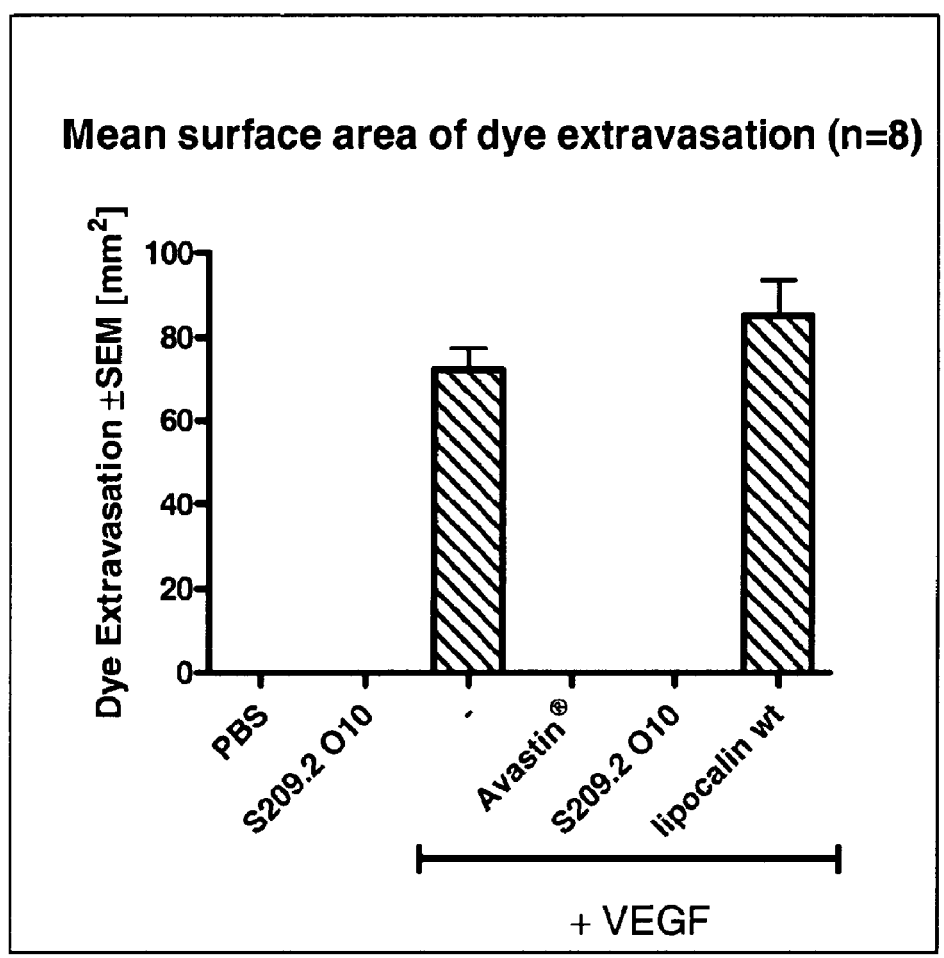
FIG. 31 shows the results of a vascular permeability assay with local administration of the tear lipocalin mutein S209.2_O10 (SEQ ID NO:33) compared to Avastin® and wildtype tear lipocalin.

Vascular Permeability Assay with Local Administration of Tear Lipocalin Mutein Duncan-Hartley guinea pigs weighing 350±50 g were shaved on the shoulder and on the dorsum. The animals received an intravenous injection via the ear vein of 1 ml of 1% Evan's Blue dye. Thirty minutes later 20 ng $VEGF_{165}$ (Calbiochem) was mixed with test substance or control article at a tenfold molar excess and injected intradermally on a 3×4 grid. Thirty minutes later, animals were euthanized by $CO_2$ asphyxiation. One hour after the VEGF injections, the skin containing the grid pattern was removed and cleaned of connective tissue. The area of dye extravasation was quantified by use of an image analyzer (Image Pro Plus 1.3, Media Cybernetics) (see FIG. 31).

Example 42

CAM (Chick Chorioallantoic Membrane) Assay

Figure 32:
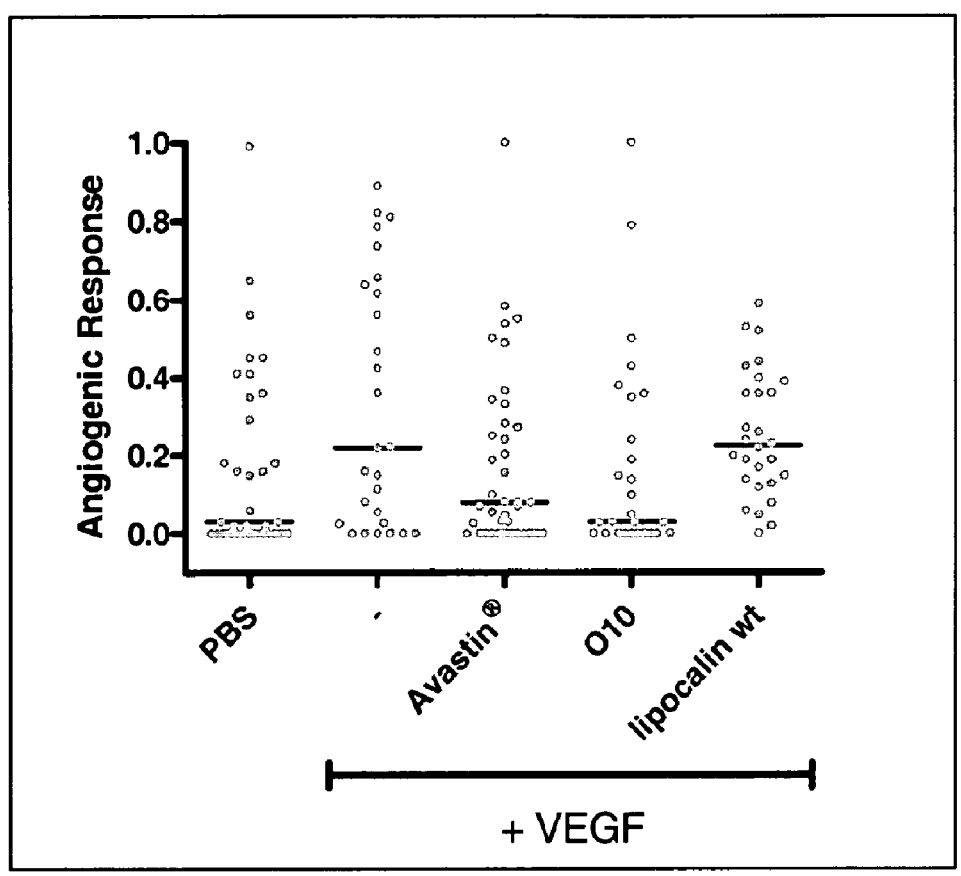
FIG. 32 shows the results of a CAM assay comparing the median angionic index for the tear lipocalin mutein S209.2_O10 (SEQ ID NO:33) and Avastin® and wild type tear lipocalin.

Collagen onplants containing FGF-2 (500 ng), VEGF (150 ng) and tear lipocalin mutein (1.35 µg) or Avastin (10 µg) as indicated were placed onto the CAM of 10 day chicken embryos (4/animal, 10 animals/group). At 24 h the tear lipocalin mutein or Avastin were reapplied topically to the onplant at the same dose. After 72 h onplants were collected and images were captured. The percentage of positive grids containing at least one vessel was determined by a blinded observer. The median angiogenic index is reported for the VEGF antagonists S209.2-O10 (SEQ ID NO:33) and Avastin® as well as wild type tear lipocalin control as the fraction of positive grids (see FIG. 32).

Example 43

Figure 33:
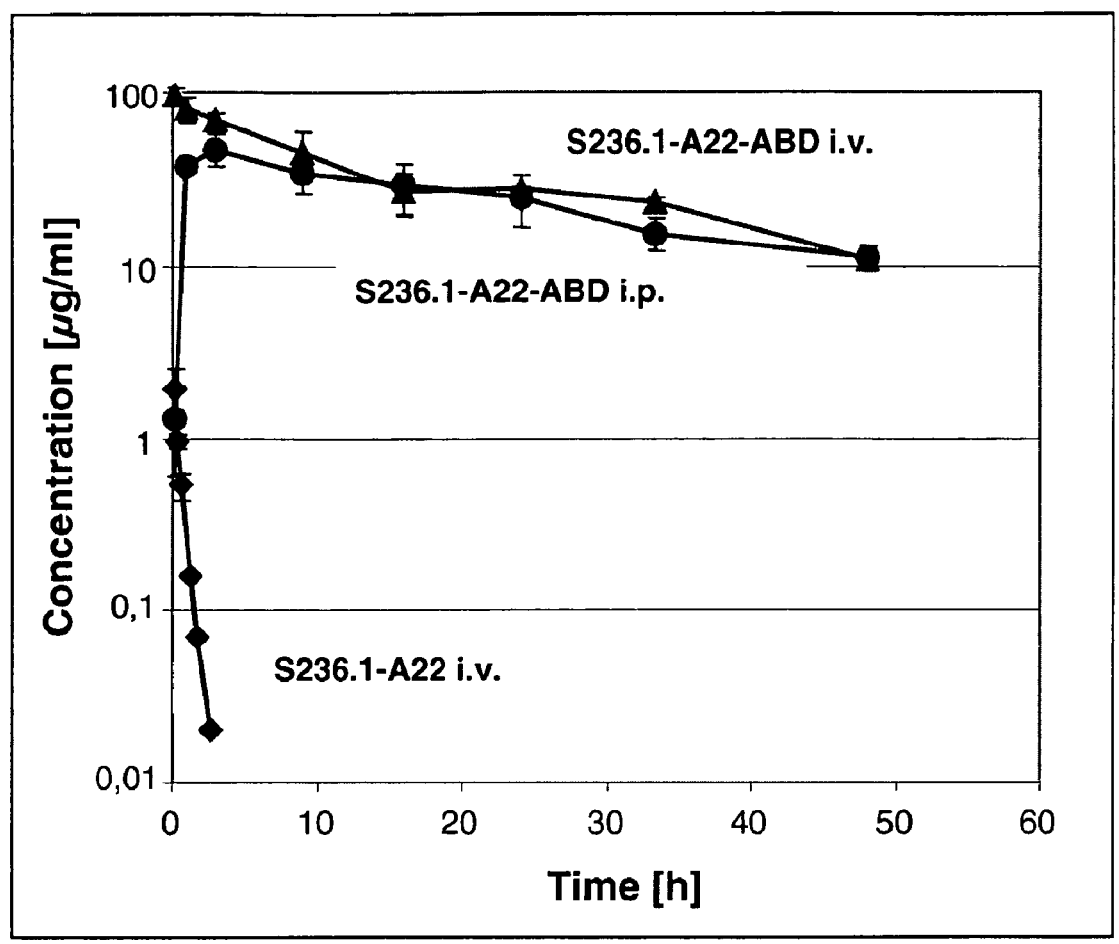
FIG. 33 shows the concentration of lipocalin mutein in plasma in NMRI mice for the tear lipocalin mutein S236.1-A22 (SEQ ID NO:44) and a fusion protein of mutein S236.1-A22 with ABD (SEQ ID NO:51).

Determination of Pharmacokinetic (PK) Parameters for A22 and A22-ABD in Mice Pharmacokinetic (PK) parameters (half-life plasma concentration, bioavailibity) for tear lipocalin mutein S236.1 A22 (SEQ ID NO:44) (4 mg/kg) after i.v. and the fusion protein of muteiin S236.1 A22 with ABD (SEQ ID NO:51) (5.4 mg/kg) following i.v. or i.p. single bolus administration were determined in NMRI mice. Plasma was prepared from terminal blood samples taken at pre-determined timepoints and the concentrations of the lipocalin mutein were determines by ELISA. Results were analyzed using WinNonlin software (Pharsight Corp., Mountain View, USA). $T_{1/2}$ A22 i.v.: 0.42 h; $T_{1/2}$ A22-ABD i.v.: 18.32 h; $T_{1/2}$ A22-ABD i.p.: 20.82 h. The bioavailability following i.p. administration of the fusion protein A22-ABD was 82.5% (see FIG. 33).

Example 44

Figure 34:
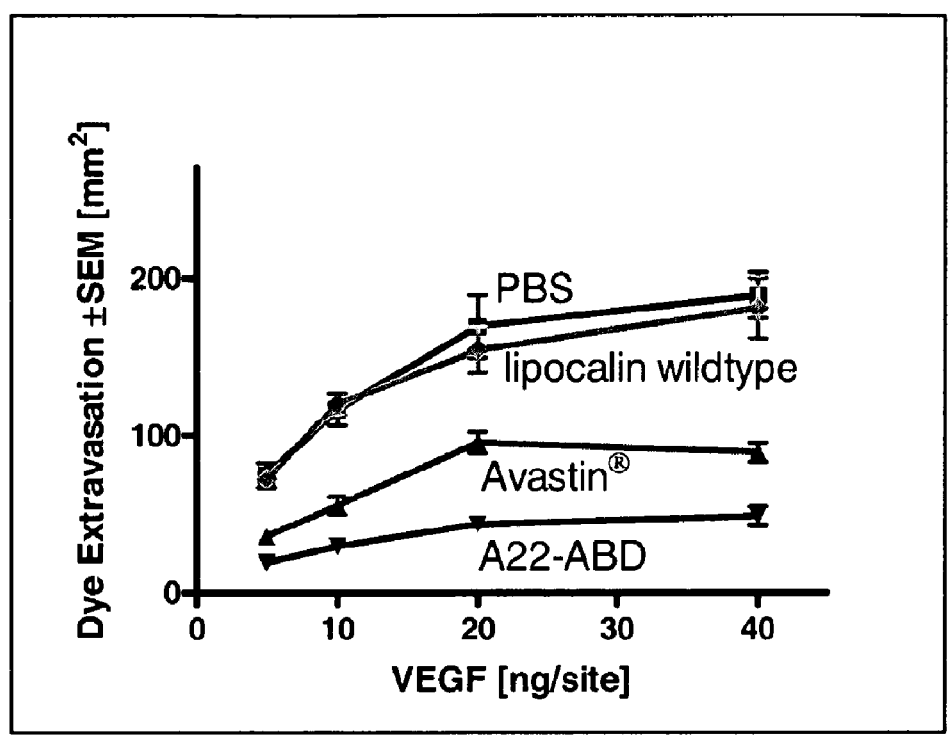
FIG. 34 shows the results of a vascular permeability assay after systemic administration of a fusion protein of tear lipocalin mutein S236.1-A22 with ABD (SEQ ID NO:51) compared to wildtype tear lipocalin, PBS buffer and Avastin®.

Vascular Permeability Assay with Systemic Administration of Tear Lipocalin Mutein Twelve hours prior to the experiment, test substances or controls were injected intravenously into 3 animals per group. Group 1: PBS vehicle; Group 2: Avastin, 10 mg/kg; Group 3: mutein S236.1 A22-ABD, 6.1 mg/kg; Group 4: TLPC51: 6.1 mg/kg. At time=0 Evan's Blue was injected. Thirty minutes later, 4 doses of VEGF (5, 10, 20 or 40 ng) were injected intradermally in triplicate on a 3×4 grid. Thirty minutes after the VEGF injections the animals were sacrificed and dye extravasation was quantified as above (see FIG. 34).

Example 45

Tumor Xenograft Model

Figure 35:
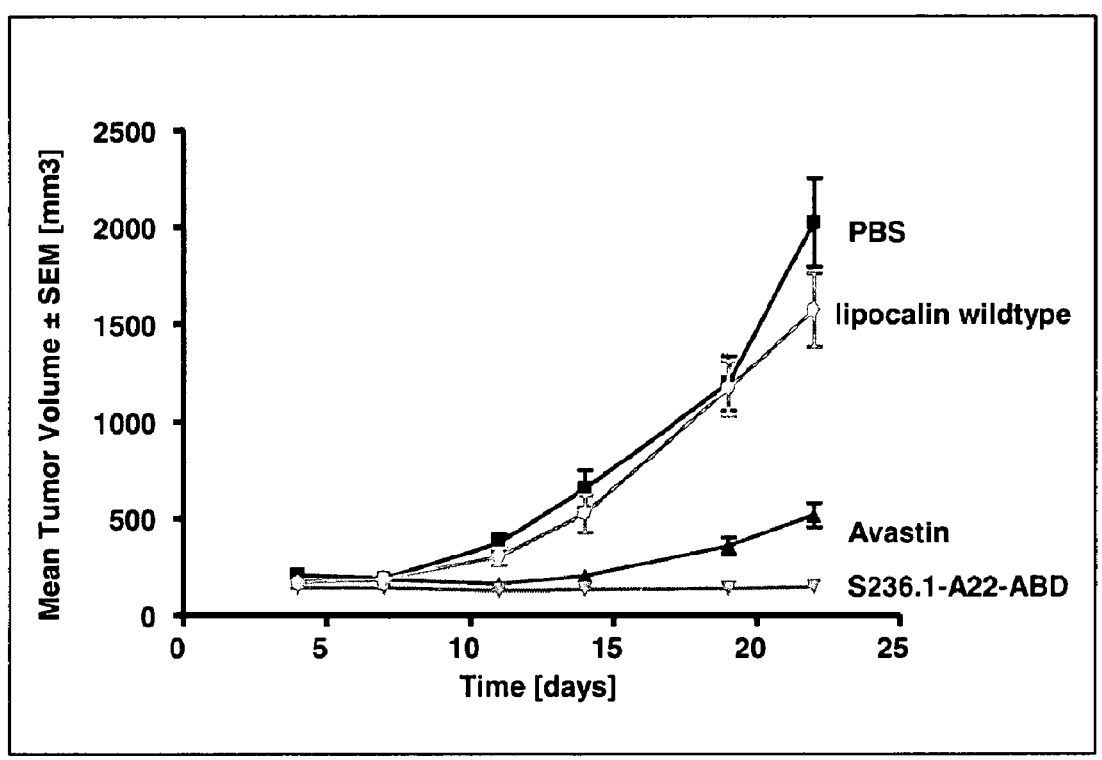
FIG. 35 shows the results of a tumor xenograft model (Swiss nude mice) for intraperitoneal administration of a fusion protein of tear lipocalin mutein S236.1-A22 with ABD (SEQ ID NO:51) compared to wildtype tear lipocalin, PBS buffer and Avastin®.

Irradiated (2.5 Gy, $Co^{60}$) Swiss nude mice were inoculated subcutaneously with $1\times10^7$ A673 rhabdomyosarcoma cells (ATTC) in matrigel into the right flank (n=12 per group). Treatments were administered intraperitoneally and were initiated on the same day and continued for 21 days. Group 1: PBS vehicle, daily; Group 2: Avastin (bevacizumab, Genentech/Roche), 5 mg/kg every 3 days; Group 3: mutein A22-ABD (SEQ ID NO:51), daily, 3.1 mg/kg; Group 4: TLPC51, daily, 3.1 mg/kg. The dose of the lipocalin A22-ABD was chosen to achieve the constant presence of an equimolar number of VEGF binding sites of the mutein and Avastin based on the A22-ABD PK data and estimated serum half life of antibodies in mice. Tumor size was measured twice weekly with a calliper and the tumor volume was estimated according to the formula (length×width²)/2. Mice were sacrificed when the tumor volume exceeded 2,000 mm³ (see FIG. 35).

Example 46

Screening of Lipocalin Mutein-Cys Variants

In order to provide a reactive group for coupling with e.g. activated PEG, an unpaired cysteine residue was introduced by site-directed mutagenesis. The recombinant mutein carrying the free Cys residue was subsequently produced in *E. coli* as described in Example 7, the expression yield determined and the affinity measured by ELISA essentially as described in Example 14. Exemplary, results from the Cys-screening of the VEGF-specific mutein S236.1-A22 (SEQ ID NO:44) are given in the table below. Cystein was introduced instead of the amino acids Thr 40, Glu 73, Asp 95, Arg 90 and Glu 131 using the following oligonucleotides

```
A22_D95C forward:
                                    (SEQ ID NO: 56)
GAGGTCGCACGTGAAGTGCCACTACATCTTTTACTCTGAGG, A22_D95C reverse:
                                    (SEQ ID NO: 57)
CCTCAGAGTAAAAGATGTAGTGGCACTTCACGTGCGACCTC, A22_T40C forward:
                                    (SEQ ID NO: 58)
GGGTCGGTGATACCCACGTGCCTCACGACCCTGGAAGGG, A22_T40C reverse:
                                    (SEQ ID NO: 59)
CCCTTCCAGGGTCGTGAGGCACGTGGGTATCACCGACCC, A22_E73C forward:
                                    (SEQ ID NO: 60)
CCGTCCTGAGCAAAACTGATTGCCCGGGGATCTACACGG, A22_E73C reverse:
                                    (SEQ ID NO: 61)
CCGTGTAGATCCCCGGGCAATCAGTTTTGCTCAGGACGG, A22_E131C forward:
                                    (SEQ ID NO: 62)
GCCTTGGAGGACTTTTGTAAAGCCGCAGGAG, A22_E131C reverse:
                                    (SEQ ID NO: 63)
CTCCTGCGGCTTTACAAAAGTCCTCCAAGGC, A22_R90C forward:
                                    (SEQ ID NO: 64)
CGTGGCAAAGATCGGGTGCTCGCACGTGAAGGACC,
and A22_R90C reverse:
                                    (SEQ ID NO: 65)
GGTCCTTCACGTGCGAGCACCCGATCTTTGCCACG.
```

TABLE XII

Affinity of the muteins S236.1-A22 and its Thr 40→Cys (SEQ ID NO: 66), Glu 73→Cys (SEQ ID NO: 67), Asp 95→Cys (SEQ ID NO: 68), Arg 90→Cys (SEQ ID NO: 69), and Glu 131→Cys (SEQ ID NO: 70) mutants for VEGF as determined by ELISA.

| Clone | Yield [μg/L] | Affinity [nM] |
|---|---|---|
| S236.1-A22 | 1000 | 10 |
| S236.1-A22 T40C | 420 | 14 |
| S236.1-A22 E73C | 300 | 13 |
| S236.1-A22 D95C | 750 | 10 |

TABLE XII-continued

Affinity of the muteins S236.1-A22 and its Thr 40→Cys (SEQ ID NO: 66), Glu 73→Cys (SEQ ID NO: 67), Asp 95→Cys (SEQ ID NO: 68), Arg 90→Cys (SEQ ID NO: 69), and Glu 131→Cys (SEQ ID NO: 70) mutants for VEGF as determined by ELISA.

| Clone | Yield [μg/L] | Affinity [nM] |
|---|---|---|
| S236.1-A22 R90C | 470 | 10 |
| S236.1-A22 E131C | 150 | >100 |

Example 47

Eotaxin-3 Secretion Assay

Figure 36:
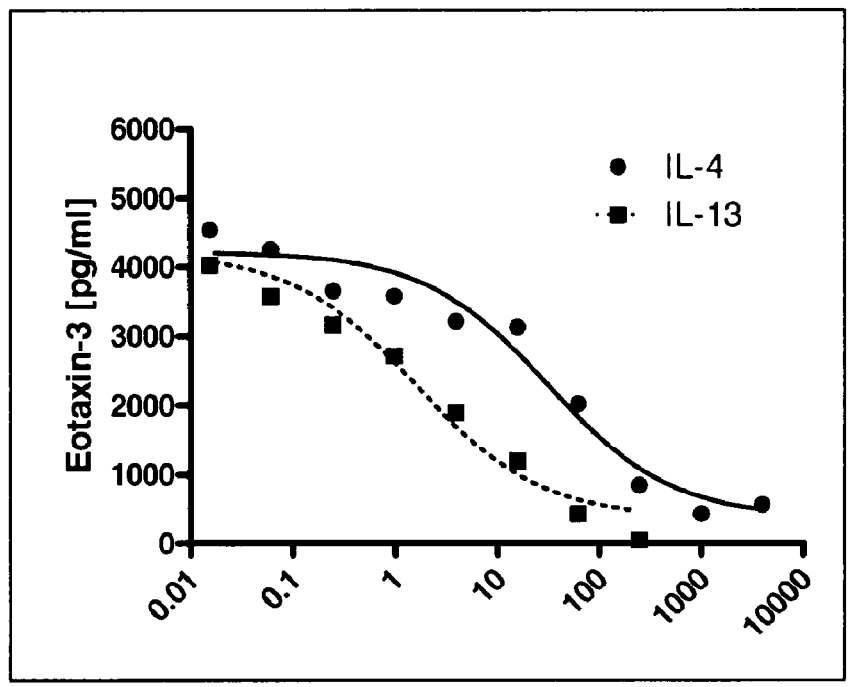
FIG. 36 shows the results of an Eotaxin-3 secretion assay with A549 cells stimulated with IL-4 or IL-13 in the absence and presence of increasing concentrations of the IL-4 receptor alpha binding mutein S191.4 B24 (SEQ ID NO:4).
Figure 37:
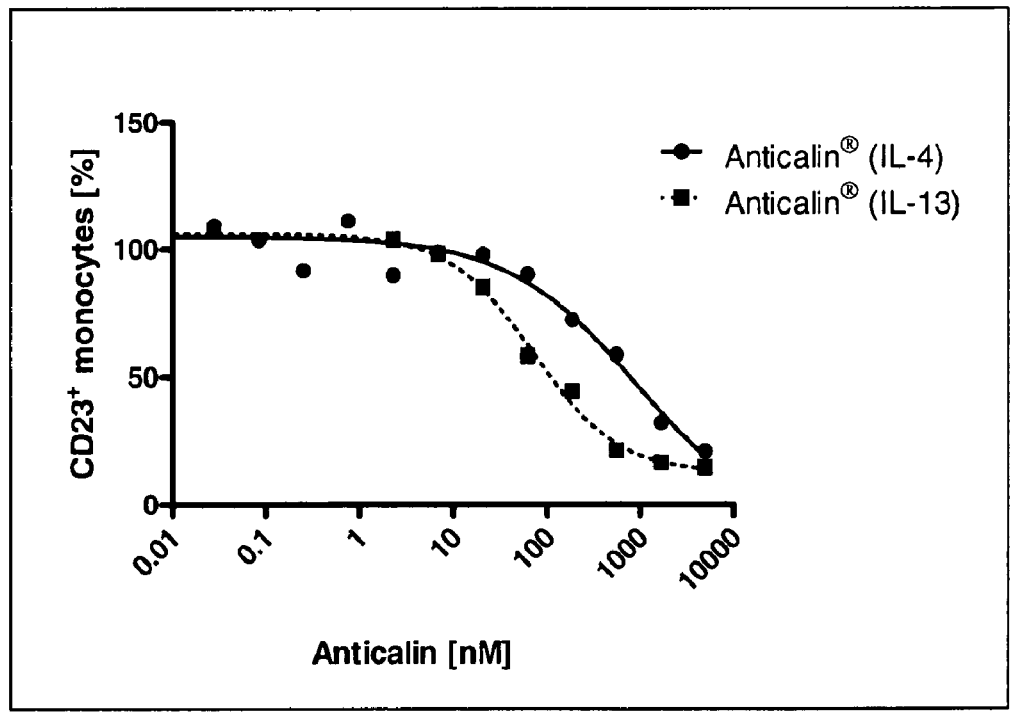
FIG. 37 shows the IL-4/IL-13 induced CD23 expression on stimulated peripheral blood mononuclear cells (PBMCs) in the absence and presence of increasing concentrations of the IL-4 receptor alpha binding mutein S191.4 B24 (SEQ ID NO:4).

An Eotaxin-3 secretion assay was performed on A549 cells over 72 hours. Lung epithelial cells, such as A549 cells, secrete eotaxin-3 upon IL-4/IL-13 stimulation. Thus, A549 cells were treated with increasing concentrations of the IL-4 receptor alpha binding mutein S191.4 B24 (SEQ ID NO:4) and stimulated with 0.7 nM IL-4 or 0.83 nM IL-13, respectively. Eotaxin-3 secretion was assessed after 72 hours using a commercial sandwich ELISA (R&D Systems). The results (FIG. 36) demonstrate that the IL-4 receptor alpha binding mutein S191.4 B24 inhibits IL-4 and IL-13 mediated eotaxin-3 secretion in A549 cells with an $IC_{50}$ value of 32 and 5.1 nM, respectively (Table XIII).

TABLE XIII $IC_{50}$ values of S191.4 B24 for IL-4 and IL-13 mediated eotaxin-3 secretion in A549 cells.

| | $IC_{50}$ (nM) |
|---|---|
| IL-4 | 32 |
| IL-13 | 5.1 |

Example 48

IL-4/IL-13 Mediated CD23 Induction on Peripheral Blood Mononuclear Cells

Total human PBMCs were isolated from buffy coat. PBMCs were treated with increasing concentrations of the IL-4 receptor alpha binding mutein S191.4 B24 and IL-4 or IL-13 were added to a final concentration of 1.0 nM and 2.5 nM, respectively. PBMCs were cultured for 48 hours in RPMI medium containing 10% FCS. Cells were stained with anti-CD 14-FITC and anti-CD23-PE antibodies and analyzed by flow cytometry. For each point, the percentage of double-positive cells out of all CD14 positive monocytes was determined and plotted as a function of mutein concentration.

From the obtained results, the $IC_{50}$ values of the mutein S191.4 B24 for inhibiting IL-4 and IL-13 mediated CD23 expression on monocytes was calculated (Table XIV).

TABLE XIV $IC_{50}$ values of S191.4 B24 for IL-4 and IL-13 mediated CD23 expression in PBMCs.

| | $IC_{50}$ (nM) |
|---|---|
| IL-4 | 905 |
| IL-13 | 72 |

Example 49

Schild Analysis of the Affinity of the IL-4 Receptor Alpha Binding Mutein S191.4 B24

Figure 38:
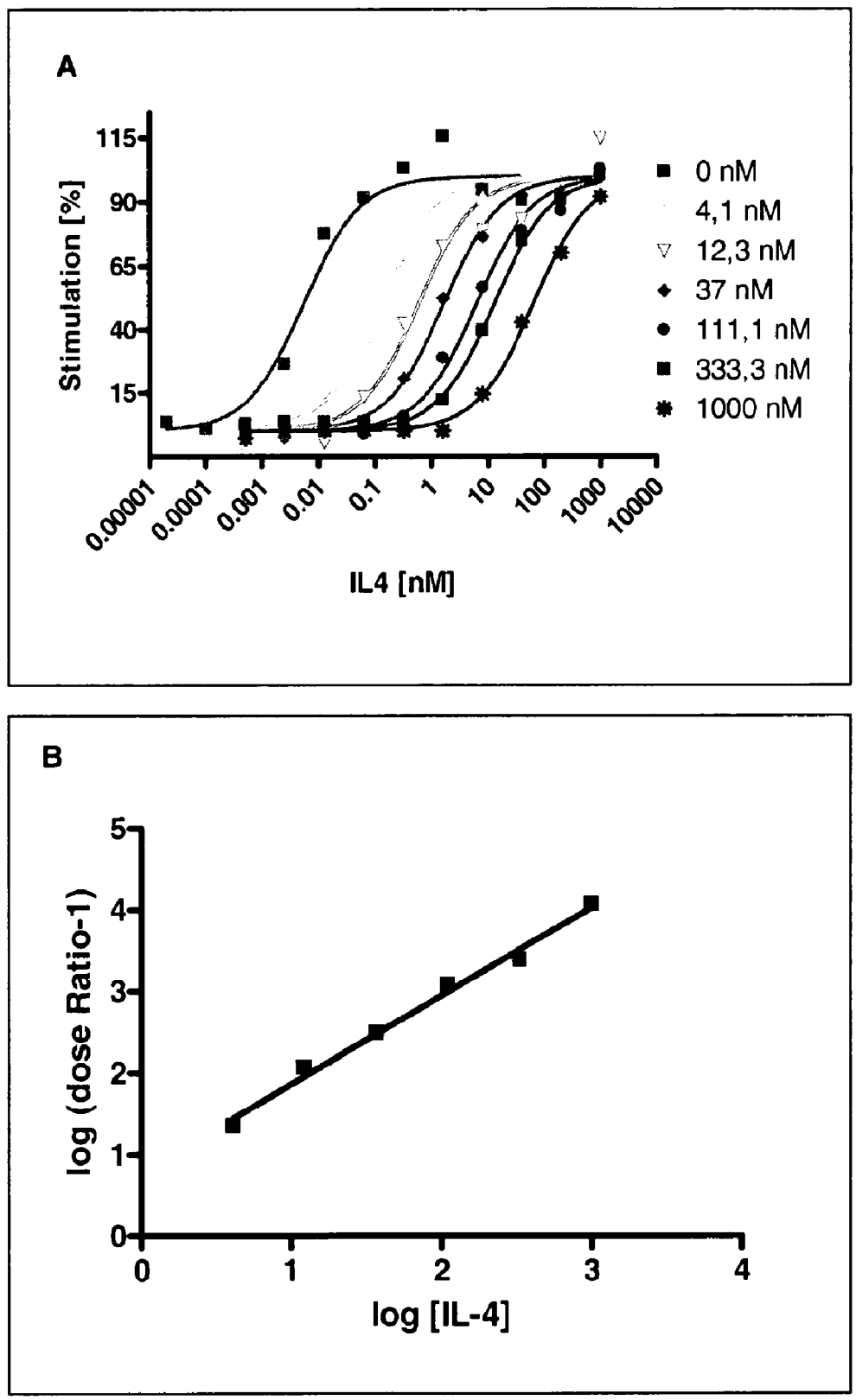
FIG. 38 shows the results of a Schild analysis of the IL-4 receptor alpha binding mutein S191.4 B24 (SEQ ID NO:4). IL-4 dose dependent proliferation of TF-1 cells was assessed in the absence or presence of several fixed concentrations of the IL-4 receptor alpha binding mutein S191.4 B24 (FIG. 38A). The Schild analysis of the obtained results (FIG. 38B) yielded a $K_d$ of 192 pM (linear regression) and 116 pM (non-linear regression).

A Schild analysis was carried out to confirm the hypothesized competitive binding mode of the muteins and to determine the $K_d$ on cells. TF-1 cells were treated with a fixed concentration of the IL-4 receptor alpha binding mutein S191.4 B24 (0, 4.1, 12.3, 37, 111.1, 333.3 or 1000 nM) and titrated with IL-4 and cell viability was assessed after 4 days (FIG. 38A). $EC_{50}$ values were determined by non-linear regression. Traditional Schild analysis of the obtained results (FIG. 38B) yielded a Kd of 192 pM (linear regression) and the more accurate non-linear regression yielded 116 pM. The Schild slope of 1.084 indicates a competitive inhibition, i.e. the mutein and IL-4 compete for the IL-4 receptor alpha binding.

Example 50

Picomolar Binding of the Mutein S191.4 B24 to Primary B Cells

Figure 39:
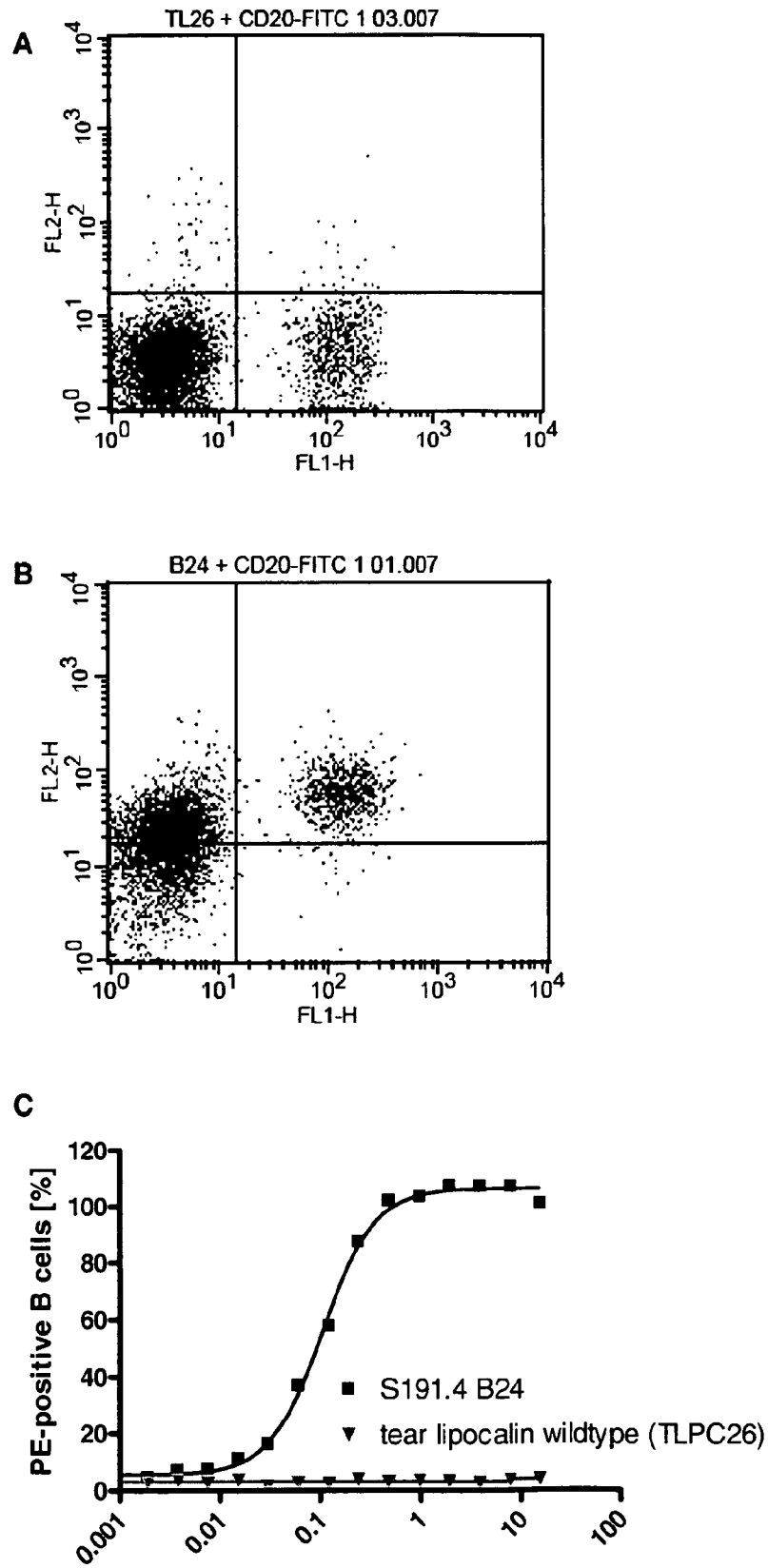
FIG. 39 shows the result of an affinity assessment of the IL-4 receptor alpha binding mutein S191.4 B24 (SEQ ID NO:4) for human primary B cells. PBMCs were isolated from human blood and incubated with different concentrations of the IL-4 receptor alpha binding human tear lipocalin mutein S191.4 B24 or the wild-type human tear lipocalin (TLPC26). Cells were then stained with anti-CD20-FITC monoclonar antibodies and a biotinylated anti-lipocalin antiserum, followed by streptavidin-PE. Results for the wild-type lipocalin and the IL-4 receptor alpha binding lipocalin mutein S191.4 B24 are shown in FIGS. 39 A and B, respectively. The determined percentage of PE-positive B cells was fitted against the concentration of the lipocalins (FIG. 39C) and the $EC_{50}$ calculated from the obtained curve. The $EC_{50}$ of the IL-4 receptor alpha binding mutein S191.4 B24 (SEQ ID NO:4) was calculated as 105 pM.
Figure 40:
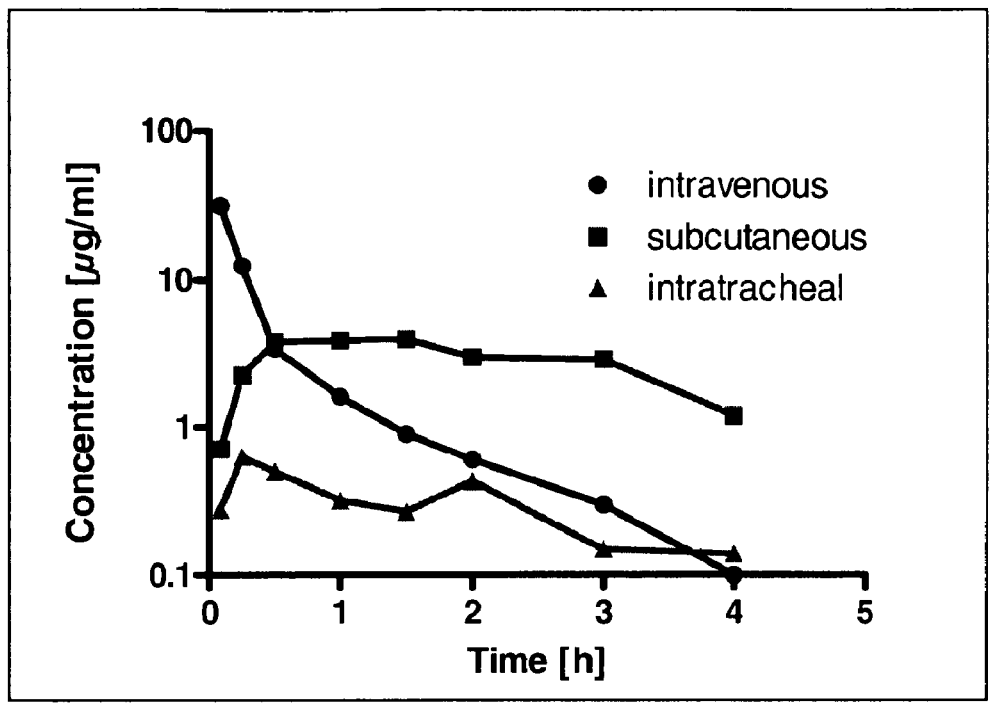
FIG. 40 shows the results of a bioavailability test of the IL-4 receptor alpha binding mutein S191.4 B24 after intravenous, subcutaneous or intratracheal administration.
Figure 41:
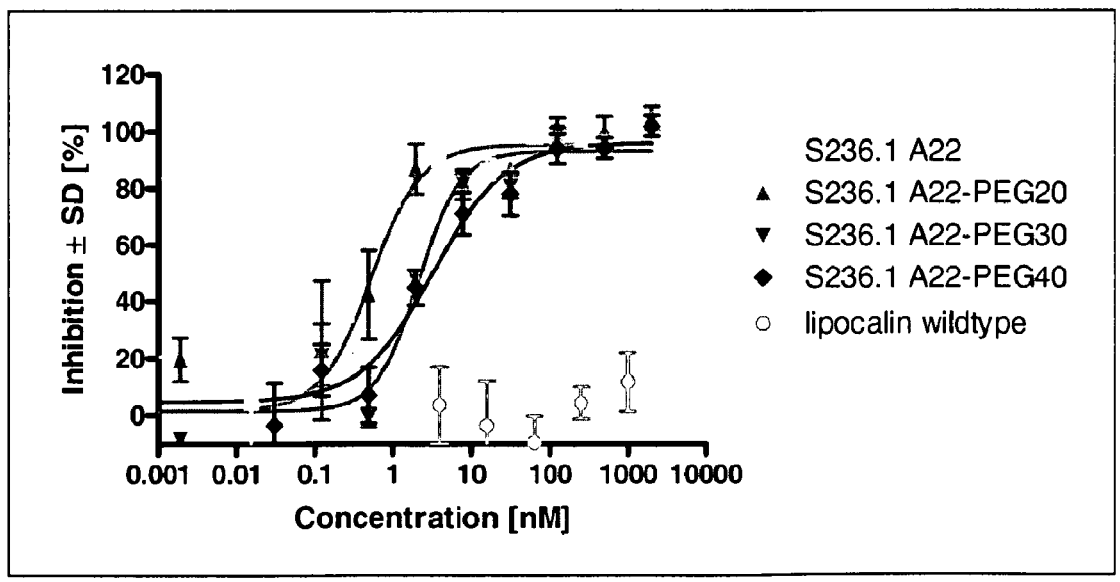
FIG. 41 shows an in vitro potency assessment of the mutein S236.1-A22 (SEQ ID NO:44) with and without PEGylation with PEG20, PEG30 or PEG40 in a VEGF-stimulated HUVEC proliferation assay.

PBMCs were isolated from human blood and incubated with different concentrations of the IL-4 receptor alpha binding human tear lipocalin mutein S191.4 B24 or the wild-type human tear lipocalin (TLPC26). Cells were then stained with anti-CD20-FITC monoclonar antibodies and a biotinylated anti-lipocalin antiserum followed by streptavidin-PE. Results for the wild-type lipocalin and the IL-4 receptor alpha binding lipocalin mutein S191.4 B24 are shown in FIGS. 39 A and B, respectively. The determined percentage of PE-positive B cells was fitted against the concentration of the lipocalin muteins (FIG. 39C) and the $EC_{50}$ calculated from the obtained curve. The $EC_{50}$ of the IL-4 receptor alpha binding mutein S191.4 B24 (SEQ ID NO:4) for binding to primary B cells was calculated as 105 pM.

Example 51

Bioavailability of the Muteins after Subcutaneous and Intratracheal Administration The bioavailability of the IL-4 receptor alpha binding mutein S191.4 B24 was determined after intravenous, subcutaneous or intratracheal administration, by monitoring the plasma concentrations of the mutein S191.4 B24 for 4 hours after a 4 mg/kg bolus injection in rats. Intratracheal administration was carried out using a commercially available intratrachial dosing device (MicroSprayer®, Penn-Century Inc, Philiadelphia, Pa., USA) that generates an aerosol from the tip of a long, thin tube attached to a syringe. The aerosol size was about 20 μm. The results of the non-compartmental pharmacokinetic (PK) analysis demonstrate 100% bioavailability upon subcutaneous injection and that, in contrast to antibodies, the pulmonary delivery of the human tear lipocalin muteins appears to be feasible. The obtained results are shown in Table XV.

TABLE XV

Half-life and bioavailability of S191.4 B24 after intravenous (i.v.), subcutaneous (s.c.) and intratracheal (i.t.) administration.

| | i.v. | s.c. | i.t. |
|---|---|---|---|
| $t_{1/2}$ [h] | 0.78 | 1.6 | 2.36 |
| bioavailability ($AUC_{last}$) | n/a | 97.2% | 10% |
| bioavailability ($AUC_{inf}$) | n/a | 119% | 13.8% |

Example 52

In Vitro Potency of PEGylated VEGF Antagonists Using a HUVEC Proliferation Assay Inhibition of VEGF stimulated HUVEC cell proliferation was assessed essentially as described in Example 20 with the following modifications: The VEGF-specific mutein S236.1-A22 (SEQ ID NO:44) was coupled to PEG 20, PEG 30 or PEG 40 at position 95C as described in Example 28 above. The mutein, its PEGylated derivatives and wildtype tear lipocalin (gene product of pTLPC26; as control) were added in a dilution series to VEGF165 and incubated for 30 min. at room temperature. The mixtures were added to HUVEC cells in triplicate wells to yield a final concentration of 20 ng/ml VEGF and concentrations between 0.003 nM and 2,000 nM as indicated. Viability of the cells was assessed after 6 days with CellTiter-Glo (Promega) according to the manufacturer's instructions.

Results from measurements employing the above-mentioned muteins are shown in FIG. 41. S236.1-A22 (SEQ ID NO:44) and its PEGylated derivatives show marked inhibition of VEGF-induced proliferation of HUVEC cells decreasing with the molecular weight of the attached PEG moiety, whereas wildtype tear lipocalin does not inhibit VEGF-induced cell proliferation (Table XVI).

TABLE XVI $IC_{50}$ values of S236.1-A22 (SEQ ID NO: 44) and its derivatives PEGylated with PEG 20, PEG 30 or PEG 40 for HUVEC cell proliferation inhibition.

| | $IC_{50}$ (nM) |
|---|---|
| S236.1-A22 | 0.4 |
| S236.1-A22-PEG20 | 0.53 |
| S236.1-A22-PEG30 | 2.13 |
| S236.1-A22-PEG40 | 3.27 |

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

What is claimed is:

1. A method for the generation of one or more mutein(s) of human tear lipocalin, wherein the one or more mutein(s) bind a given non-natural ligand of human tear lipocalin with detectable binding affinity, comprising:
   (a) subjecting a nucleic acid molecule encoding a human tear lipocalin to mutagenesis at least 12, 14, or 16 of the codons of any of the amino acid sequence positions 26-34, 56-58, 80, 83, 104-106 and 108 of the linear wild type amino acid sequence of mature human tear lipocalin (SEQ ID NO: 71), wherein at least one of the codons encoding cysteine residues at sequence positions 61 and 153 of the linear wild type amino acid sequence of the mature human tear lipocalin (SEQ ID NO: 71) has been mutated to encode any other amino acid residue, thereby obtaining a plurality of nucleic acids encoding muteins of human tear lipocalin,
   (b) expressing the nucleic acid molecule(s) obtained in (a) in an expression system, thereby obtaining one or more mutein(s); wherein the expression system comprises a bacterial or isolated eukaryotic host cell, or an in vitro translation system,
   (c) contacting the one or more muteins of step (b) with a non-natural ligand of human tear lipocalin to allow formation of complexes between said ligand and one or more mutein(s) having binding affinity for said ligand, wherein the non-natural ligand is a compound selected from the group consisting of a chemical compound in free or conjugated form that exhibits features of an immunological hapten, a peptide, a protein or another macromolecule, and
   (d) selecting the one or more mutein(s) that have detectable binding affinity to said non-natural ligand.

2. The method according to claim 1, wherein all 18 of the codons of amino acid sequence positions 26, 27, 28, 29, 30, 31, 32, 33, 34, 56, 57, 58, 80, 83, 104, 105, 106, and 108 of the linear wild type amino acid sequence of mature human tear lipocalin set forth in SEQ ID NO: 71 are mutated.

3. The method according to claim 1, wherein at least one of the codons encoding amino acid sequence positions 61 and 153 of the linear wild type amino acid sequence of mature human tear lipocalin set forth in SEQ ID NO: 71 is mutated to encode at position 61 an alanine, phenylalanine, lysine, arginine, threonine, asparagine, tyrosine, methionine, serine, proline or tryptophan and/or at position 153 a serine or alanine.

4. The method according to any claim 1, wherein the codons encoding amino acid sequence positions 111 and 114 of the linear wild type amino acid sequence of mature human tear lipocalin set forth in SEQ ID NO: 71 are mutated to encode at position 111 an arginine and at position 114 a tryptophan.

5. The method according to claim 1, wherein the codon encoding the cysteine at position 101 of the linear wild type amino acid sequence of mature human tear lipocalin set forth in SEQ ID NO: 71 is mutated to encode any other amino acid.

6. The method according to claim 5, wherein the codon encoding the cysteine at position 101 of the linear polypeptide sequence of mature human tear lipocalin is mutated to encode a serine.

7. The method according to claim 1, wherein the ligand is a protein or a fragment thereof.

8. The method according to claim 1, wherein the selection in step (c) is carried out under competitive conditions.

9. The method according to claim 1, wherein each of the plurality of nucleic acids coding for the plurality of muteins of human tear lipocalin, is operably fused at the 3' end with a gene coding for the coat protein pIII of a filamentous bacteriophage of the M13-family or for a fragment of this coat protein, in order to select at least one mutein for the binding of a given ligand.

10. The method according to claim 1, wherein the expression system in step (b) is an isolated bacterial or eukaryotic host cell.

11. A mutein of human tear lipocalin having detectable binding affinity to a non-natural ligand of human tear lipocalin, wherein at least one of the cysteine residues occurring at sequence positions 61 and 153 of the linear wild type amino acid sequence of mature human tear lipocalin (SEQ ID NO: 71) is replaced by other amino acids and wherein at least 12, 14, or 16 mutated amino acid residues are present at any of the sequence positions 26-34, 56-58, 80, 83, 104-106, and 108 of the linear wild type amino acid sequence of mature human tear lipocalin set forth in SEQ ID NO: 71.

12. The mutein of human tear lipocalin according to claim 11, wherein the cysteine residues occurring at sequence positions 61 and 153 of the linear wild type amino acid sequence of the mature human tear lipocalin are replaced by other amino acids and wherein at least 12, 14, or 16 mutated amino acid residues are present at any of the sequence positions 26-34, 56-58, 80, 83, 104-106, and 108 of the linear wild type amino acid sequence of mature human tear lipocalin.

13. The mutein according to claim 11, wherein the mutein comprises mutated amino acid residues at all 18 of the sequence positions 26, 27, 28, 29, 30, 31, 32, 33, 34, 56, 57, 58, 80, 83, 104, 105, 106, and 108.

14. The mutein according to claim 11, wherein the mutein comprises at least one of the amino acid substitutions Cys 61→Ala, Phe, Lys, Arg, Thr, Asn, Tyr, Met, Ser, Pro or Trp and Cys 153→Ser or Ala.

15. The mutein according to claim 11, wherein the mutein further comprises an amino acid substitution of the cysteine residue at position 101 of the linear wild type amino acid sequence of the mature human tear lipocalin.

16. The mutein according to claim 15, wherein the mutein comprises the mutation Cys 101→Ser.

17. The mutein according to claim 11, wherein the mutein is at its N-terminus or its C-tetniinus operably fused to a member selected from the group consisting of an enzyme, a protein or a protein domain, a peptide, a signal sequence and an affinity tag.

18. The mutein according to claim 11, wherein the mutein is fused to a moiety that extends the serum half-life of the mutein.

19. The mutein according to claim 18, wherein the moiety that extends the serum half-life is selected from the group consisting of an Fc part of an immunoglobulin, a CH3 domain of an immunoglobulin, a CH4 domain of an immunoglobulin, albumin or an albumin fragment, an albumin binding peptide, an albumin binding protein and transferrin.

20. The mutein according to claim 19, wherein the albumin binding protein is selected from the group consisting of a bacterial albumin binding protein, an antibody directed against albumin, an antibody fragment directed against albumin, and a lipocalin mutein with binding activity for albumin.

21. The mutein according to claim 20, wherein the bacterial albumin protein is an albumin binding domain of streptococcal protein G.

22. The mutein according to claim 11, wherein the mutein is conjugated to a label selected from the groups consisting of organic molecules, enzyme labels, radioactive labels, fluorescent labels, chromogenic labels, luminescent labels, haptens, digoxigenin, biotin, metal complexes, metals, colloidal gold and a moiety that extends the serum half-life of the mutein.

23. The mutein according to claim 22, wherein the moiety that extends the serum half-life is selected from the group consisting of a polyalkylene glycol molecule, hydroxyethyl starch, palmitic acid or other fatty acid molecules, an Fc part of an immunoglobulin, a CH3 domain of an immunoglobulin, a CH4 domain of an immunoglobulin, albumin or an albumin fragment, an albumin binding peptide, an albumin binding protein, and transferrin.

24. The mutein according to claim 23, wherein the albumin binding protein is a bacterial albumin binding protein or a lipocalin mutein with binding activity for albumin.

25. The mutein according to claim 24, wherein the bacterial albumin protein is an albumin binding domain of streptococcal protein G.

26. The mutein according to claim 23, wherein the polyalkylene glycol molecule is polyethylene glycol (PEG) or an activated derivative thereof.

27. The mutein according to claim 11, wherein said non-natural ligand is a protein or a fragment thereof.

28. The mutein of claim 27, wherein the protein or fragment thereof is selected from the group of vascular endothelial growth factor receptor 2 (VEGF-R2), and interleukin 4 receptor alpha chain (IL-4 receptor alpha).

29. The mutein according to claim 28, wherein the protein is IL-4 receptor alpha.

30. The mutein according to claim 29, wherein the protein is selected from the group consisting of human IL-4 receptor alpha, an extracellular region of IL-4 receptor alpha and a domain of IL-4 receptor alpha.

31. The mutein according to claim 30, wherein the mutein acts as an interleukin 13 (IL-13) antagonist.

32. The mutein according to claim 31, wherein the mutein acts as an antagonist of human IL-13.

33. The mutein according to claim 29, wherein the mutein acts as an IL-4 antagonist.

34. The mutein according to claim 33, wherein the mutein acts as an antagonist of human IL-4.

35. The mutein according claim 29, wherein the mutein is cross-reactive with cynomolgus IL-4 receptor alpha.

36. The mutein according to claim 29, wherein the mutein comprises at least two amino acid substitutions of native amino acids by cysteine residues at any of positions 26-34, 56-58, 80, 83, 104-106, and 108 with respect to the amino acid sequence of mature human tear lipocalin.

37. The mutein according to claim 29, wherein the mutein binds an extracellular region or a domain of IL-4 receptor alpha with a $K_D$ selected from the group of a $K_D$ of 200 nM or less, a $K_D$ of 100 nM or less, a $K_D$ of 20 nM or less, and a $K_D$ of 1 nM or less.

38. The mutein according to claim 29, wherein the mutein comprises at least 12, 14 or 16 amino acid substitutions with respect to the amino acid sequence of mature human tear lipocalin, which are selected from the group consisting of Arg 26→Ser, Pro; Glu 27→Arg; Phe 28→Cys; Glu 30→Arg; Met 31→Ala; Asn 32→Tyr, His; Leu 33→Tyr; Glu 34→Gly, Ser, Ala, Asp, Lys, Asn, Thr, Arg; Leu 56→Gln; Ile 57→Arg; Ser 58→Ile, Ala, Arg, Val, Thr, Asn, Lys, Tyr, Leu, Met; Asp 80→Ser; Lys 83→Arg; Glu 104→Leu; Leu 105→Cys; His 106→Pro; and Lys 108→Gln.

39. The mutein according to claim 38, further comprising at least one amino acid substitution selected from the group consisting of Met 39→Val; Thr 42→Met, Ala; Thr 43→Ile, Pro, Ala; Glu 45→Lys, Gly; Asn 48→Asp, His, Ser, Thr; Val 53→Leu, Phe, Ile, Ala, Gly, Ser; Thr 54→Ala, Leu; Met 55→Leu, Ala, Ile, Val, Phe, Gly, Thr, Tyr; Glu 63→Lys, Gln, Ala, Gly, Arg; Val 64→Gly, Tyr, Met, Ser, Ala, Lys, Arg, Leu, Asn, His, Thr, Ile; Ala 66→Ile, Leu, Val, Thr, Met; Glu 69→Lys, Gly; Lys 70→Arg, Gln, Glu; Thr 78→Ala; Ile 89→Val; Asp 95→Asn, Ala, Gly; and Tyr 100→His.

40. The mutein according to claim 38, wherein the mutein comprises the amino acid substitutions: Arg 26→Ser; Glu 27→Arg; Phe 28→Cys; Glu 30→Arg; Met 31→Ala; Leu 33→Tyr; Leu 56→Gln; Ile 57→Arg; Asp 80→Ser; Lys 83→Arg; Glu 104→Leu; Leu 105→Cys; His 106→Pro; and Lys 108→Gln.

41. The mutein of claim 38, wherein the mutein comprises one of the following sets of amino acid substitutions:

(1) Arg 26→Ser; Glu 27→Arg; Phe 28→Cys; Glu 30→Arg; Met 31→Ala; Asn 32→Tyr; Leu 33→Tyr; Glu 34→Gly; Leu 56→Gln; Ile 57→Arg; Ser 58→Ile; Asp 80→Ser; Lys 83→Arg; Glu 104→Leu; Leu 105→Cys; His 106→Pro; Lys 108→Gln;

(2) Arg 26→Ser; Glu 27→Arg; Phe 28→Cys; Glu 30→Arg; Met 31→Ala; Asn 32→Tyr; Leu 33→Tyr; Glu 34→Lys; Leu 56→Gln; Ile 57→Arg; Ser 58→Asn; Asp 80→Ser; Lys 83→Arg; Glu 104→Leu; Leu 105→Cys; His 106→Pro; Lys 108→Gln;

(3) Arg 26→Ser; Glu 27→Arg; Phe 28→Cys, Glu 30→Arg; Met 31→Ala; Asn 32→Tyr; Leu 33→Tyr; Leu 56→Gln; Ile 57→Arg; Ser 58→Arg; Asp 80→Ser; Lys 83→Arg; Glu 104→Leu; Leu 105→Cys; His 106→Pro; Lys 108→Gln;

(4) Arg 26→Ser; Glu 27→Arg; Phe 28→Cys; Glu 30→Arg; Met 31→Ala; Asn 32→Tyr; Leu 33→Tyr; Glu 34→Ser; Leu 56→Gln; Ile 57→Arg; Asp 80→Ser; Lys 83→Arg; Glu 104→Leu; Leu 105→Cys; His 106→Pro; Lys 108→Gln;

(5) Arg 26→Ser; Glu 27→Arg; Phe 28→Cys; Glu 30→Arg; Met 31→Ala; Asn 32→His; Leu 33→Tyr; Glu 34→Ser; Leu 56→Gln; Ile 57→Arg; Ser 58→Ala; Asp 80→Ser; Lys 83→Arg; Glu 104→Leu; Leu 105→Cys; His 106→Pro; Lys 108→Gln;

(6) Arg 26→Ser; Glu27→Arg; Phe28→Cys; Glu 30→Arg; Met 31→Ala; Asn 32→Tyr; Leu 33→Tyr; Glu 34→Asp; Leu 56→Gln; Ile 57→Arg; Ser 58→Lys; Asp 80→Ser; Lys 83→Arg; Glu 104→Leu; Leu 105→Cys; His 106→Pro; Lys 108→Gln; and (7) Arg 26→Ser; Glu 27→Arg; Phe 28→Cys; Glu 30→Arg; Met 31→Ala; Asn 32→Tyr; Leu 33→Tyr; Glu 34→Gly; Leu 56→Gln; Ile 57→Arg; Asp 80→Ser; Lys 83→Arg; Glu 104→Leu; Leu 105→Cys; His 106→Pro; Lys 108→Gln.

42. The mutein according to claim 29, wherein the mutein has an amino acid sequence as set forth in any one of SEQ ID NOs: 2-8.

43. A pharmaceutical composition comprising a mutein of human tear lipocalin as recited in claim 11 and a pharmaceutically acceptable excipient.

44. A method for producing a mutein of human tear lipocalin having detectable binding affinity to a non-natural ligand of human tear lipocalin, comprising:

(i) expressing a nucleic acid encoding the mutein in an expression system which comprises a bacterial or isolated eukaryotic host cell, or an in vitro translation system, and (ii) isolating the mutein from the host cell or its culture, or the in vitro translation system;

wherein the mutein of human tear lipocalin having detectable binding affinity to a non-natural ligand of human tear lipocalin is mutated in at least one of the cysteine residues occurring at sequence positions 61 and 153 of the linear wild type amino acid sequence of mature human tear lipocalin (SEQ ID NO: 71) by replacement with other amino acids; and at least 12, 14, or 16 mutated amino acid residues are present at any of the sequence positions 26-34, 56-58, 80, 83, 104-106, and 108 of the linear wild type amino acid sequence of mature human tear lipocalin set forth in SEQ ID NO: 71.

* * * * *

UNITED STATES PATENT AND TRADEMARK OFFICE
CERTIFICATE OF CORRECTION

| | |
|---|---|
| PATENT NO. | : 8,313,924 B2 |
| APPLICATION NO. | : 12/309820 |
| DATED | : November 20, 2012 |
| INVENTOR(S) | : Jensen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 424 days.

Signed and Sealed this
Twenty-third Day of April, 2013

Teresa Stanek Rea
*Acting Director of the United States Patent and Trademark Office*

SEQUENCE LISTING

```
<160> NUMBER OF SEQ ID NOS: 71

<210> SEQ ID NO 1
<211> LENGTH: 3700
<212> TYPE: DNA
<213> ORGANISM: Artificial
<220> FEATURE:
<223> OTHER INFORMATION: Expression vector pTLPC10

<400> SEQUENCE: 1
ccatcgaatg gccagatgat taattcctaa tttttgttga cactctatca ttgatagagt      60
tattttacca ctccctatca gtgatagaga aaagtgaaat gaatagttcg acaaaaatct    120
agataacgag ggcaaaaaat gaaaaagaca gctatcgcga ttgcagtggc actggctggt    180
ttcgctaccg tagcgcaggc cgacgcatcg atgaccggtg gtcagcagat gggtgcctca    240
gacgaggaga ttcaggatgt gtcagggacg tggtatctga aggccatgac ggtggacagg    300
gagttccctg agatgaatct ggaatcggtg acacccatga ccctcacgac cctggaaggg    360
ggcaacctgg aagccaaggt caccatgctg ataagtggcc ggagccagga ggtgaaggcc    420
gtcctggaga aaactgacga gccgggaaaa tacacggccg acggggcaa gcacgtggca    480 tacatcatca ggtcgcacgt gaaggaccac tacatctttt actctgaggg cgagctccac    540
gggaagccgg tcccaggggt gtggctcgtg ggcagagacc caagaacaa cctggaagcc    600 ttggaggact tgagaaagc cgcaggagcc cgcggactca gcacggagag catcctcatc    660
cccaggcaga gcgaaaccag ctctccaggg agcgcttggt ctcacccgca gttcgaaaaa    720
taataagctt gacctgtgaa gtgaaaaatg gcgcacattg tgcgacattt ttttgtctg    780 ccgtttaccg ctactgcgtc acggatctcc acgcgccctg tagcggcgca ttaagcgcgg    840
cgggtgtggt ggttacgcgc agcgtgaccg ctacacttgc cagcgcccta gcgcccgctc    900
ctttcgcttt cttcccttcc tttctcgcca cgttcgccgg ctttccccgt caagctctaa    960 atcggggggct ccctttaggg ttccgattta gtgctttacg gcacctcgac cccaaaaaac   1020
ttgattaggg tgatggttca cgtagtgggc catcgccctg atagacggtt tttcgccctt   1080
tgacgttgga gtccacgttc tttaatagtg gactcttgtt ccaaactgga acaacactca   1140
accctatctc ggtctattct tttgatttat aagggatttt gccgatttcg gcctattggt   1200
taaaaaatga gctgatttaa caaaaattta acgcgaattt taacaaaata ttaacgctta   1260
caatttcagg tggcactttt cggggaaatg tgcgcggaac ccctatttgt ttatttttct   1320
aaatacattc aaatatgtat ccgctcatga gacaataacc ctgataaatg cttcaataat   1380
attgaaaaag gaagagtatg agtattcaac atttccgtgt cgcccttatt cccttttttg   1440
cggcattttg ccttcctgtt tttgctcacc cagaaacgct ggtgaaagta aaagatgctg   1500
aagatcagtt gggtgcacga gtgggttaca tcgaactgga tctcaacagc ggtaagatcc   1560
ttgagagttt tcgccccgaa gaacgttttc caatgatgag cacttttaaa gttctgctat   1620
gtggcgcggt attatcccgt attgacgccg ggcaagagca actcggtcgc cgcatacact   1680
attctcagaa tgacttggtt gagtactcac cagtcacaga aaagcatctt acggatggca   1740
```

```
tgacagtaag agaattatgc agtgctgcca taaccatgag tgataacact gcggccaact   1800
tacttctgac aacgatcgga ggaccgaagg agctaaccgc ttttttgcac aacatggggg   1860
atcatgtaac tcgccttgat cgttgggaac cggagctgaa tgaagccata ccaaacgacg   1920
agcgtgacac cacgatgcct gtagcaatgg caacaacgtt gcgcaaacta ttaactggcg   1980
aactacttac tctagcttcc cggcaacaat tgatagactg gatggaggcg ataaagttg    2040 caggaccact tctgcgctcg gcccttccgg ctggctggtt tattgctgat aaatctggag   2100
ccggtgagcg tggctctcgc ggtatcattg cagcactggg gccagatggt aagccctccc   2160
gtatcgtagt tatctacacg acggggagtc aggcaactat ggatgaacga atagacaga    2220 tcgctgagat aggtgcctca ctgattaagc attggtagga attaatgatg tctcgtttag   2280
ataaaagtaa agtgattaac agcgcattag agctgcttaa tgaggtcgga atcgaaggtt   2340
taacaacccg taaactcgcc cagaagctag gtgtagagca gcctacattg tattggcatg   2400
taaaaaataa gcgggctttg ctcgacgcct tagccattga gatgttagat aggcaccata   2460 ctcactttg cccttagaa ggggaaagct ggcaagattt tttacgtaat aacgctaaaa     2520
gttttagatg tgctttacta agtcatcgcg atggagcaaa agtacattta ggtacacggc   2580
ctacagaaaa acagtatgaa actctcgaaa atcaattagc cttttatgc caacaaggtt    2640 tttcactaga gaatgcatta tatgcactca gcgcagtggg gcatttttact ttaggttgcg  2700 tattggaaga tcaagagcat caagtcgcta aagaagaaag ggaaacacct actactgata   2760
gtatgccgcc attattacga caagctatcg aattatttga tcaccaaggt gcagagccag   2820
ccttcttatt cggccttgaa ttgatcatat gcggattaga aaaacaactt aaatgtgaaa   2880
gtgggtctta aaagcagcat aacctttttc cgtgatggta acttcactag tttaaaagga   2940
tctaggtgaa gatcctttt gataatctca tgaccaaaat cccttaacgt gagttttcgt    3000
tccactgagc gtcagacccc gtagaaaaga tcaaaggatc ttcttgagat ccttttttc    3060 tgcgcgtaat ctgctgcttg caaacaaaaa accaccgct accagcggtg tttgtttgc     3120 cggatcaaga gctaccaact ctttttccga aggtaactgg cttcagcaga gcgcagatac   3180
caaatactgt ccttctagtg tagccgtagt taggccacca cttcaagaac tctgtagcac   3240
cgcctacata cctcgctctg ctaatcctgt taccagtggc tgctgccagt ggcgataagt   3300
cgtgtcttac cgggttggac tcaagacgat agttaccgga taaggcgcag cggtcgggct   3360 gaacggggg ttcgtgcaca cagcccagct tggagcgaac gacctacacc gaactgagat    3420
acctacagcg tgagctatga gaaagcgcca cgcttcccga aggagaaag gcggacaggt    3480 atccggtaag cggcagggtc ggaacaggag agcgcacgag ggagcttcca ggggggaaacg  3540 cctggtatct ttatagtcct gtcgggtttc gccacctctg acttgagcgt cgatttttgt   3600
gatgctcgtc aggggggcgg agcctatgga aaaacgccag caacgcggcc ttttttacggt  3660 tcctggcctt ttgctggcct tttgctcaca tgacccgaca                         3700
```

<210> SEQ ID NO 2
<211> LENGTH: 152
<212> TYPE: PRT
<213> ORGANISM: Artificial
<220> FEATURE:
<223> OTHER INFORMATION: Mutein of human tear lipocalin with binding
      affinity for IL-4R alpha -continued

```
<400> SEQUENCE: 2

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Gly Ser Val
            20                  25                  30

Thr Pro Met Thr Leu Thr Thr Leu Glu Gly Gly Asn Leu Glu Ala Lys
        35                  40                  45

Val Thr Met Gln Arg Ile Gly Arg Ser Gln Glu Val Lys Ala Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe Tyr
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 3
<211> LENGTH: 152
<212> TYPE: PRT
<213> ORGANISM: Artificial
<220> FEATURE:
<223> OTHER INFORMATION: Mutein of human tear lipocalin with binding
      affinity for IL-4R alpha

<400> SEQUENCE: 3

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Lys Ser Val
            20                  25                  30

Thr Pro Met Thr Leu Thr Thr Leu Glu Gly Gly Asn Leu Glu Ala Lys
        35                  40                  45

Phe Thr Ala Gln Arg Asn Gly Arg Trp Gln Glu Leu Lys Leu Val Leu
    50                  55                  60

Glu Lys Thr Asp Glu Pro Gly Lys Tyr

```
<220> FEATURE:
<223> OTHER INFORMATION: Mutein of human tear lipocalin with binding
      affinity for IL-4R alpha

<400> SEQUENCE: 4

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Glu Ser Val
                20                  25                  30

Thr Pro Met Thr Leu Thr Thr Leu Glu Gly Gly Asn Leu Glu Ala Lys
            35                  40                  45

Phe Thr Leu Gln Arg Arg Gly Arg Trp Gln Glu Gly Lys Leu Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe Tyr
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 5
<211> LENGTH: 152
<212> TYPE: PRT
<213> ORGANISM: Artificial
<220> FEATURE:
<223> OTHER INFORMATION: Mutein of human tear lipocalin with binding
      affinity for IL-4R alpha

<400> SEQUENCE: 5

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Ser Ser Val
                20                  25                  30

Thr Pro Met Thr Leu Thr Thr Leu Glu Gly Gly Asn Leu Glu Ala Lys
            35                  40                  45

Phe Thr Ala Gln Arg Ser Gly Arg Trp Gln Glu Tyr Lys Leu Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 6
<211> LENGTH: 152
<212> TYPE: PRT
<213> ORGANISM: Artificial
<220> FEATURE:
<223> OTHER INFORMATION: Mutein of human tear lipocalin with binding
      affinity for IL-4R alpha

<400> SEQUENCE: 6

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala His Tyr Ser Ser Val
                20                  25                  30

Thr Pro Met Thr Leu Thr Thr Leu Glu Gly Gly Asn Leu Glu Ala Lys
            35                  40                  45

Leu Thr Leu Gln Arg Ala Gly Arg Trp Gln Gly Lys Ile Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe Tyr
                85                  90                  95

Ser Glu Gly Leu Cys Pro Gly Gln Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 7
<211> LENGTH: 152
<212> TYPE: PRT
<213> ORGANISM: Artificial
<220> FEATURE:
<223> OTHER INFORMATION: Mutein of human tear lipocalin with binding
      affinity for IL-4R alpha

<400> SEQUENCE: 7

Ala Ser Asp Glu Glu Ile Gln Asp Val Ser G

```
<210> SEQ ID NO 8
<211> LENGTH: 152
<212> TYPE: PRT
<213> ORGANISM: Artificial
<220> FEATURE:
<223> OTHER INFORMATION: Mutein of human tear lipocalin with binding
      affinity for IL-4R alpha

<400> SEQUENCE: 8

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Gly Ser Val
            20                  25                  30

Thr Pro Met Thr Leu Thr Thr Leu Glu Gly Gly Asn Leu Glu Ala Lys
        35                  40                  45

Leu Thr Leu Gln Arg Ser Gly Arg Trp Gln Glu Ser Lys Val Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe Tyr
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 9
<211> LENGTH: 4041
<212> TYPE: DNA
<213> ORGANISM: Artificial
<220> FEATURE:
<223> OTHER INFORMATION: Phasmid vector pTlc27

<400> SEQUENCE: 9
ccataacgct cggttgccgc cgggcgtttt ttattggcca gatgattaat tcctaatttt      60
tgttgacact ctatcattga tagagttatt ttaccactcc ctatcagtga tagagaaaag     120
tgaaatgaat agttcgacaa aaatctagat aacgagggca aaaaatgaaa aagacagcta    180
tcgcgattgc agtggcactg gctggtttcg ctaccgtagc gcaggccgcc tcagacgagg    240
agattcagga tgtgtcaggg acgtggtatc tgaaggccat gacggtggac agggagttcc    300
ctgagatgaa tctggaatcg gtgacaccca tgaccctcac gaccctggaa ggggcaacc     360 tggaagccaa ggtcaccatg ctgataagtg gccggagcca ggaggtgaag gccgtcctgg    420
agaaaactga cgagccggga aaatacacgg ccgacggggg caagcacgtg gcatacatca    480
tcaggtcgca cgtgaaggac cactacatct tttactctga gggcgagctc cacgggaagc    540
cggtcccagg ggtgtggctc gtgggcagag accccaagaa caacctggaa gccttggagg    600
actttgagaa agccgcagga gcccgcggac tcagcacgga gagcatcctc atccccaggc    660
agagcgaaac cagctctcca gggagcgctt ggtctcaccc gcagttcgaa aaataggctg    720
gcggcggctc tggtggtggt tctggcggcg gctctgaggg tggtggctct gagggtggcg    780
gttctgaggg tggcggctct gagggaggcg gttccggtgg tggctctggt tccggtgatt    840
ttgattatga aaagatggca aacgctaata agggggctat gaccgaaaat gccgatgaaa    900
```

-continued

```
acgcgctaca gtctgacgct aaaggcaaac ttgattctgt cgctactgat tacggtgctg    960
ctatcgatgg tttcattggt gacgtttccg gccttgctaa tggtaatggt gctactggtg   1020
attttgctgg ctctaattcc caaatggctc aagtcggtga cggtgataat tcacctttaa   1080
tgaataattt ccgtcaatat ttaccttccc tccctcaatc ggttgaatgt cgccttttg    1140
tctttggcgc tggtaaacca tatgaatttt ctattgattg tgacaaaata aacttattcc   1200
gtggtgtctt tgcgtttctt ttatatgttg ccacctttat gtatgtattt tctacgtttg   1260
ctaacatact gcgtaataag gagtcttaat aagcttgacc tgtgaagtga aaaatggcgc   1320
acattgtgcg acatttttt tgtctgccgt ttaccgctac tgcgtcacgg atctccacgc    1380
gccctgtagc ggcgcattaa gcgcggcggg tgtggtggtt acgcgcagcg tgaccgctac   1440
acttgccagc gccctagcgc ccgctccttt cgctttcttc ccttcctttc tcgccacgtt   1500
cgccggcttt ccccgtcaag ctctaaatcg ggggctccct ttagggttcc gatttagtgc   1560
tttacggcac ctcgacccca aaaaacttga ttagggtgat ggttcacgta gtgggccatc   1620
gccctgatag acgttttttc gcccttggac gttggagtcc acgttcttta atagtggact   1680
cttgttccaa actggaacaa cactcaaccc tatctcggtc tattcttttg atttataagg   1740
gattttgccg atttcggcct attggttaaa aaatgagctg atttaacaaa aatttaacgc   1800
gaattttaac aaaatttggc gaaaatgaga cgttgatcgg cacgtaagag gttccaactt   1860
tcaccataat gaaataagat cactaccggg cgtattttt gagttatcga ttttcagg     1920
agctaaggaa gctaaaatgg agaaaaaat cactggatat accaccgttg atatatccca   1980
atggcatcgt aaagaacatt tgaggcatt tcagtcagtt gctcaatgta cctataacca   2040
gaccgttcag ctggatatta cggcctttt aaagaccgta agaaaaata agcacaagtt    2100
ttatccggcc tttattcaca ttcttgcccg cctgatgaat gctcatccgg aattccgtat   2160
ggcaatgaaa gacggtgagc tggtgatatg ggatagtgtt cacccttgtt acaccgtttt   2220
ccatgagcaa actgaaacgt tttcatcgct ctggagtgaa taccacgacg atttccggca   2280
gtttctacac atatattcgc aagatgtggc gtgttacggt gaaaacctgg cctatttccc   2340
taaagggttt attgagaata tgtttttcgt ctcagccaat ccctgggtga gtttcaccag   2400
ttttgattta aacgtggcca atatggacaa cttcttcgcc cccgttttca ctatgggcaa   2460
atattatacg caaggcgaca aggtgctgat gccgctggcg attcaggttc atcatgccgt   2520
ttgtgatggc ttccatgtcg gcagaatgct taatgaatta caacagtact gcgatgagtg   2580
gcagggcggg gcgtaatagg aattaatgat gtctcgttta gataaaagta agtgattaa    2640
cagcgcatta gagctgctta atgaggtcgg aatcgaaggt ttaacaaccc gtaaactcgc   2700
ccagaagcta ggtgtagagc agcctacatt gtattggcat gtaaaaaata gcgggcttt    2760
gctcgacgcc ttagccattg agatgttaga taggcaccat actcactttt gccctttaga   2820
aggggaaagc tggcaagatt ttttacgtaa taacgctaaa agttttagat gtgctttact   2880
aagtcatcgc gatggagcaa aagtacattt aggtacacgg cctacagaaa aacagtatga   2940
aactctcgaa aatcaattag cctttttatg ccaacaaggt ttttcactag agaatgcatt   3000
atatgcactc agcgcagtgg ggcatttttac tttaggttgc gtattggaag tcaagagca    3060
tcaagtcgct aaagaagaaa gggaaacacc tactactgat agtatgccgc cattattacg   3120
acaagctatc gaattatttg atcaccaagg tgcagagcca gccttcttat tcggccttga   3180
attgatcata tgcggattag aaaaacaact taaatgtgaa agtgggtctt aaaagcagca   3240
taaccttttt ccgtgatggt aacttcacta gtttaaaagg atctaggtga agatcctttt   3300
```

-continued

```
tgataatctc atgaccaaaa tcccttaacg tgagttttcg ttccactgag cgtcagaccc    3360
cgtagaaaag atcaaaggat cttcttgaga tcctttttt ctgcgcgtaa tctgctgctt     3420
gcaaacaaaa aaaccaccgc taccagcggt ggtttgtttg ccggatcaag agctaccaac    3480 tcttttccg aaggtaactg gcttcagcag agcgcagata ccaaatactg tccttctagt     3540
gtagccgtag ttaggccacc acttcaagaa ctctgtagca ccgcctacat acctcgctct    3600
gctaatcctg ttaccagtgg ctgctgccag tggcgataag tcgtgtctta ccgggttgga   3660
ctcaagacga tagttaccgg ataaggcgca gcggtcgggc tgaacggggg gttcgtgcac    3720
acagcccagc ttggagcgaa cgacctacac cgaactgaga tacctacagc gtgagctatg    3780
agaaagcgcc acgcttcccg aagggagaaa ggcggacagg tatccggtaa gcggcagggt    3840
cggaacagga gagcgcacga gggagcttcc aggggggaaac gcctggtatc tttatagtcc    3900
tgtcgggttt cgccacctct gacttgagcg tcgatttttg tgatgctcgt caggggggcg    3960
gagcctatgg aaaaacgcca gcaacgcggc cttttacgg ttcctggcct tttgctggcc     4020
ttttgctcac atgacccgac a                                              4041
```

<210> SEQ ID NO 10
<211> LENGTH: 63
<212> TYPE: DNA
<213> ORGANISM: Artificial
<220> FEATURE:
<223> OTHER INFORMATION: Oligonucleotide primer TL46 (loop 1/2 forward)
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 10

```
aaggccatga cggtggacnn snnsnnsnns nnsnnsnnsn nsnnstcggt gacacccatg    60
acc                                                                  63
```

```
<210> SEQ ID NO 11
<211> LENGTH: 45
<212> TYPE: DNA
<213> ORGANISM: Artificial
<220> FEATURE:
<223> OTHER INFORMATION: Oligonucleotide primer TL47 (loop 1/2 reverse)
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 11
cacctcctgg gaccggccsn nsnnsnncat ggtgaccttg gcttc            45

<210> SEQ ID NO 12
<211> LENGTH: 54
<212> TYPE: DNA
<213> ORGANISM: Artificial
<220> FEATURE:
<223> OTHER INFORMATION: Oligonucleotide primer TL48 (loop 3/4 forward)
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 12
gacgagccgg gaaaatacac ggccnnsggg ggcnnscacg tggcatacat catc            54

<210> SEQ ID NO 13
<211> LENGTH: 56
<212> TYPE: DNA
<213> ORGANISM: Artificial
<220> FEATURE:
<223> OTHER INFORMATION: Oliogonucleotide primer TL49 (loop 3/4 reverse)
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t

<400> SEQUENCE: 13
cgagccacac ccctgggacc ggsnncccsn nsnnsnngcc ctcagagtaa aagatg            56

<210> SEQ ID NO 14
<211> LENGTH: 56
<212> TYPE: DNA
<213> ORGANISM: Artificial
<220> FEATURE:
<223> OTHER INFORMATION: Oligonucleotide primer AN-14
```

-continued

<400> SEQUENCE: 14
gtattttccc ggctcatcag ttttctccag gacggccttc acctcctggg accggc    56

<210> SEQ ID NO 15
<211> LENGTH: 24
<212> TYPE: DNA
<213> ORGANISM: Artificial
<220> FEATURE:
<223> OTHER INFORMATION: Oligonucleotide primer TL50bio (assembly 5')

<400> SEQUENCE: 15
tatctgaagg ccatgacggt ggac    24

<210> SEQ ID NO 16
<211> LENGTH: 24
<212> TYPE: DNA
<213> ORGANISM: Artificial
<220> FEATURE:
<223> OTHER INFORMATION: Oligonucleotide primer TL51bio (assembly 3')

<400> SEQUENCE: 16
tgcccacgag ccaccccct ggga    24

<210> SEQ ID NO 17
<211> LENGTH: 64
<212> TYPE: DNA
<213> ORGANISM: Artificial
<220> FEATURE:
<223> OTHER INFORMATION: Oligonucleotide primer TL70 random primer loop
     1
<220> FEATURE:
<221> NAME/KEY: misc_feature
<222> LOCATION: (44)..(45)
<223> OTHER INFORMATION: n is a, c, g, or t

<400> SEQUENCE: 17
gaaggccatg acggtggact cccgctgccc gcgggcgtac tacnnstcgg tgacacccat    60
gacc    64

<210> SEQ ID NO 18
<211> LENGTH: 78
<212> TYPE: DNA
<213> ORGANISM: Artificial
<220> FEATURE:
<223> OTHER INFORMATION: Oligonucleotide primer TL71 random primer loop
     2
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t

```
<400> SEQUENCE: 18
catcagtttt ctccaggacs nncttsnnct cctgsnnccg gccsnnccgc tgsnnggtsn    60
ncttggcttc caggttgc                                                 78

<210> SEQ ID NO 19
<211> LENGTH: 25
<212> TYPE: DNA
<213> ORGANISM: Artificial
<220> FEATURE:
<223> OTHER INFORMATION: Oligonucleotide primer TL72 assembly primer

<400> SEQUENCE: 19
tcctggagaa aactgatgag ccggg                                         25

<210> SEQ ID NO 20
<211> LENGTH: 825
<212> TYPE: PRT
<213> ORGANISM: Homo sapiens

<400> SEQUENCE: 20
```

| Met<br>1 | Gly | Trp | Leu | Cys<br>5 | Ser | Gly | Leu | Leu | Phe<br>10 | Pro | Val | Ser | Cys | Leu<br>15 | Val |
|---|---|---|---|---|---|---|---|---|---|---|---|---|---|---|---|
| Leu | Leu | Gln | Val<br>20 | Ala | Ser | Ser | Gly | Asn<br>25 | Met | Lys | Val | Leu | Gln<br>30 | Glu | Pro |
| Thr | Cys | Val<br>35 | Ser | Asp | Tyr | Met | Ser<br>40 | Ile | Ser | Thr | Cys | Glu<br>45 | Trp | Lys | Met |
| Asn | Gly<br>50 | Pro | Thr | Asn | Cys | Ser<br>55 | Thr | Glu | Leu | Arg | Leu<br>60 | Leu | Tyr | Gln | Leu |
| Val<br>65 | Phe | Leu | Leu | Ser | Glu<br>70 | Ala | His | Thr | Cys | Ile<br>75 | Pro | Glu | Asn | Asn | Gly<br>80 |
| Gly | Ala | Gly | Cys | Val<br>85 | Cys | His | Leu | Leu | Met<br>90 | Asp | Asp | Val | Val | Ser<br>95 | Ala |
| Asp | Asn | Tyr | Thr<br>100 | Leu | Asp | Leu | Trp | Ala<br>105 | Gly | Gln | Gln | Leu | Leu<br>110 | Trp | Lys |
| Gly | Ser | Phe<br>115 | Lys | Pro | Ser | Glu | His<br>120 | Val | Lys | Pro | Arg | Ala<br>125 | Pro | Gly | Asn |
| Leu | Thr<br>130 | Val | His | Thr | Asn | Val<br>135 | Ser | Asp | Thr | Leu | Leu<br>140 | Leu | Thr | Trp | Ser |
| Asn<br>145 | Pro | Tyr | Pro | Pro | Asp<br>150 | Asn | Tyr | Leu | Tyr | Asn<br>155 | His | Leu | Thr | Tyr | Ala<br>160 |
| Val | Asn | Ile | Trp | Ser<br>165 | Glu | Asn | Asp | Pro | Ala<br>170 | Asp | Phe | Arg | Ile | Tyr<br>175 | Asn |
| Val | Thr | Tyr | Leu<br>180 | Glu | Pro | Ser | Leu | Arg<br>185 | Ile | Ala | Ala | Ser | Thr<br>190 | Leu | Lys |
| Ser | Gly | Ile<br>195 | Ser | Tyr | Arg | Ala | Arg<br>200 | Val | Arg | Ala | Trp | Ala<br>205 | Gln | Cys | Tyr |
| Asn | Thr<br>210 | Thr | Trp | Ser | Glu | Trp<br>215 | Ser | Pro | Ser | Thr | Lys<br>220 | Trp | His | Asn | Ser |
| Tyr<br>225 | Arg | Glu | Pro | Phe | Glu<br>230 | Gln | His | Leu | Leu | Leu<br>235 | Gly | Val | Ser | Val | Ser<br>240 |
| Cys | Ile | Val | Ile | Leu<br>245 | Ala | Val | Cys | Leu | Leu<br>250 | Cys | Tyr | Val | Ser | Ile<br>255 | Thr |
| Lys | Ile | Lys | Lys<br>260 | Glu | Trp | Trp | Asp | Gln<br>265 | Ile | Pro | Asn | Pro | Ala<br>270 | Arg | Ser |
| Arg | Leu | Val<br>275 | Ala | Ile | Ile | Ile | Gln<br>280 | Asp | Ala | Gln | Gly | Ser<br>285 | Gln | Trp | Glu |

```
Lys Arg Ser Arg Gly Gln Glu Pro Ala Lys Cys Pro His Trp Lys Asn
    290                 295                 300
Cys Leu Thr Lys Leu Leu Pro Cys Phe Leu Glu His Asn Met Lys Arg
305                 310                 315                 320
Asp Glu Asp Pro His Lys Ala Ala Lys Glu Met Pro Phe Gln Gly Ser
                325                 330                 335
Gly Lys Ser Ala Trp Cys Pro Val Glu Ile Ser Lys Thr Val Leu Trp
            340                 345                 350
Pro Glu Ser Ile Ser Val Val Arg Cys Val Glu Leu Phe Glu Ala Pro
        355                 360                 365
Val Glu Cys Glu Glu Glu Glu Val Glu Glu Lys Gly Ser Phe
    370                 375                 380
Cys Ala Ser Pro Glu Ser Ser Arg Asp Asp Phe Gln Glu Gly Arg Glu
385                 390                 395                 400
Gly Ile Val Ala Arg Leu Thr Glu Ser Leu Phe Leu Asp Leu Leu Gly
                405                 410                 415
Glu Glu Asn Gly Gly Phe Cys Gln Gln Asp Met Gly Glu Ser Cys Leu
            420                 425                 430
Leu Pro Pro Ser Gly Ser Thr Ser Ala His Met Pro Trp Asp Glu Phe
        435                 440                 445
Pro Ser Ala Gly Pro Lys Glu Ala Pro Pro Trp Gly Lys Glu Gln Pro
    450                 455                 460
Leu His Leu Glu Pro Ser Pro Pro Ala Ser Pro Thr Gln Ser Pro Asp
465                 470                 475                 480
Asn Leu Thr Cys Thr Glu Thr Pro Leu Val Ile Ala Gly Asn Pro Ala
                485                 490                 495
Tyr Arg Ser Phe Ser Asn Ser Leu Ser Gln Ser Pro Cys Pro Arg Glu
            500                 505                 510
Leu Gly Pro Asp Pro Leu Leu Ala Arg His Leu Glu Glu Val Glu Pro
        515                 520                 525
Glu Met Pro Cys Val Pro Gln Leu Ser Glu Pro Thr Thr Val Pro Gln
    530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
                565                 570                 575
Glu Phe Val His Ala Val Glu Gln Gly Gly Thr Gln Ala Ser Ala Val
            580                 585                 590
Val Gly Leu Gly Pro Pro Gly Glu Ala Gly Tyr Lys Ala Phe Ser Ser
        595                 600                 605
Leu Leu Ala Ser Ser Ala Val Ser Pro Glu Lys Cys Gly Phe Gly Ala
    610                 615                 620
Ser Ser Gly Glu Glu Gly Tyr Lys Pro Phe Gln Asp Leu Ile Pro Gly
625                 630                 635                 640
Cys Pro Gly Asp Pro Ala Pro Val Pro Val Pro Leu Phe Thr Phe Gly
                645                 650                 655
Leu Asp Arg Glu Pro Pro Arg Ser Pro Gln Ser Ser His Leu Pro Ser
            660                 665                 670
Ser Ser Pro Glu His Leu Gly Leu Glu Pro Gly Glu Lys Val Glu Asp
        675                 680                 685
Met Pro Lys Pro Pro Leu Pro Gln Glu Gln Ala Thr Asp Pro Leu Val
    690                 695                 700
Asp Ser Leu Gly Ser Gly Ile Val Tyr Ser Ala Leu Thr Cys His Leu
705                 710                 715                 720
```

-continued

```
Cys Gly His Leu Lys Gln Cys His Gly Gln Glu Asp Gly Gly Gln Thr
                725                 730                 735

Pro Val Met Ala Ser Pro Cys Cys Cys Cys Gly Asp Arg Ser
        740                 745                 750

Ser Pro Pro Thr Thr Pro Leu Arg Ala Pro Asp Pro Ser Pro Gly Gly
        755                 760                 765

Val Pro Leu Glu Ala Ser Leu Cys Pro Ala Ser Leu Ala Pro Ser Gly
770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
        820                 825

<210> SEQ ID NO 21
<211> LENGTH: 1356
<212> TYPE: PRT
<213> ORGANISM: Homo sapiens

<400> SEQUENCE: 21

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270
```

-continued

```
Val Asn Arg Asp Leu Lys Thr Gln Ser Gly Ser Glu Met Lys Lys Phe
        275                 280                 285
Leu Ser Thr Leu Thr Ile Asp Gly Val Thr Arg Ser Asp Gln Gly Leu
290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
                340                 345                 350
Lys Tyr Leu Gly Tyr Pro Pro Glu Ile Lys Trp Tyr Lys Asn Gly
                355                 360                 365
Ile Pro Leu Glu Ser Asn His Thr Ile Lys Ala Gly His Val Leu Thr
370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
                420                 425                 430
Asp Ser Tyr Gln Tyr Gly Thr Thr Gln Thr Leu Thr Cys Thr Val Tyr
                435                 440                 445
Ala Ile Pro Pro Pro His His Ile His Trp Tyr Trp Gln Leu Glu Glu
450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
                500                 505                 510
Thr Val Ser Thr Leu Val Ile Gln Ala Ala Asn Val Ser Ala Leu Tyr
                515                 520                 525
Lys Cys Glu Ala Val Asn Lys Val Gly Arg Gly Glu Arg Val Ile Ser
530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
                595                 600                 605
Leu Trp Lys Leu Asn Ala Thr Met Phe Ser Asn Ser Thr Asn Asp Ile
610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
                675                 680                 685
Thr Ala Ser Gly Asn Pro Pro Pro Gln Ile Met Trp Phe Lys Asp Asn
690                 695                 700
```

-continued

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
            725                 730                 735

Cys Gln Ala Cys Ser Val Leu Gly Cys Ala Lys Val Glu Ala Phe Phe
        740                 745                 750

Ile Ile Glu Gly Ala Gln Glu Lys Thr Asn Leu Glu Ile Ile Ile Leu
    755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
    930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

```
Asp Tyr Thr Thr Pro Glu Met Tyr Gln Thr Met Leu Asp Cys Trp
        1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 22
<211> LENGTH: 232
<212> TYPE: PRT
<213> ORGANISM: Homo sapiens

<400> SEQUENCE: 22

Met Asn Phe Leu Leu Ser Trp Val His Trp Ser Leu Ala Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125
```

-continued

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 23
<211> LENGTH: 207
<212> TYPE: PRT
<213> ORGANISM: Homo sapiens

<400> SEQUENCE: 23

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
                20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
        50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
                100                 105                 110

Glu Met Ser Leu Glu Glu His Ser Gln Cys Glu Cys Arg Pro Lys Lys
            115                 120                 125

Lys Asp Ser Ala Val Lys Pro Asp Arg Ala Ala Thr Pro His His Arg
130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 24
<211> LENGTH: 419
<212> TYPE: PRT
<213> ORGANISM: Homo sapiens -continued

```
<400> SEQUENCE: 24

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400
```

```
Tyr Ser Glu Glu Val Cys Arg Cys Val Pro Ser Tyr Trp Lys Arg Pro
                405                 410                 415
Gln Met Ser

<210> SEQ ID NO 25
<211> LENGTH: 354
<212> TYPE: PRT
<213> ORGANISM: Homo sapiens

<400> SEQUENCE: 25

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Ile Arg Ala Ala Ser
        35                  40                  45

Ser Leu Glu Glu Leu Leu Arg Ile Thr His Ser Glu Asp Trp Lys Leu
50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro
```

```
<210> SEQ ID NO 26
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 26

Ala Ser Asp Glu Glu Ile Gln Asp Val Ser Gly Thr Trp Tyr Leu Lys
1               5                   10                  15

Ala Met Thr Val Asp Ser Gly Ala Leu Arg Cys Leu Ala Gly Ser Val
            20                  25                  30

Thr Pro Met Thr Leu Thr Thr Leu Glu Gly Gly Asn Leu Glu Ala Lys
        35                  40                  45

Val Thr Met His Ile Lys Gly Arg Ser Gln Glu Val Lys Ala Val Leu
    50                  55                  60

Glu Lys Thr Asp Glu Pro Gly Lys Tyr Thr Ala Ile Gly Gly Ile His
65                  70                  75                  80

Val Ala Tyr Ile Ile Arg Ser His Val Lys Asp His Tyr Ile Phe Tyr
                85                  90                  95

Ser Glu Gly Cys Leu Asn Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 27
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 27

Ala Ser Asp Glu Glu Ile Gln Asp Val Ser Gly Thr Trp Tyr Leu Lys
1               5                   10                  15

Ala Met Thr Val Asp Pro Gly Ala Leu Arg Cys Leu Ala Gly Ser Val
            20                  25                  30

Thr Pro Thr Thr Leu Thr Thr Leu Glu Gly Gly Asn Leu Glu Ala Lys
        35                  40                  45

Val Thr Met His Ile Glu Gly Arg Ser Gln Glu Val Lys Val Val Leu
    50                  55                  60

Gly Lys Thr Asp Glu Pro Gly Lys Tyr Thr Ala Ile Gly Gly Ile His
65                  70                  75                  80

Val Ala Tyr Ile Ile Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 28
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 28

Ala Ser Asp Glu Glu Ile Gln Asp Val Ser Gly Thr Trp Tyr Leu Lys
1               5                   10                  15

Ala Met Thr Val Asp Ser Gly Ala Leu Arg Cys Leu Ala Gly Ser Val
                20                  25                  30

Thr Pro Thr Thr Leu Thr Thr Leu Glu Gly Gly Asn Leu Glu Val Lys
            35                  40                  45

Val Thr Met His Ile Lys Gly Arg Ser Gln Glu Val Lys Ala Val Leu
        50                  55                  60

Gly Lys Thr Asp Glu Pro Gly Lys Tyr Thr Ala Ile Gly Gly Ile His
65                  70                  75                  80

Val Ala His Ile Thr Arg Ser His Val Lys Asp His Tyr Val Phe Tyr
                85                  90                  95

Ser Glu Gly Cys Leu Asn Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 29
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 29

Ala Ser Asp Glu Glu Ile Gln Asp Val Ser Gly Thr Trp Tyr Leu Lys
1               5                   10                  15

Ala Met Thr Val Asp Pro Gly Ala Leu Arg Cys Leu Ala Gly Ser Ala
                20                  25                  30

Thr Pro Met Ala Leu Thr Thr Leu Glu Gly Gly Asn Leu Glu Ala Arg
            35                  40                  45

Val Thr Val Arg Ile Lys Gly Arg Ser Gln Glu Val Lys Ala Ile Leu
        50                  55                  60

Glu Lys Thr Asp Glu Pro Gly Arg Tyr Thr Ala Ile Gly Gly Ile His
65                  70                  75                  80

Val Ala Tyr Ile Thr Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 30
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 30

Ala Ser Asp Glu Glu Ile Gln Asp Val Ser Gly Thr Trp Tyr Leu Lys
1               5                   10                  15

Ala Met Thr Val Asp Pro Gly Ala Leu Arg Cys Leu Ala Gly Ser Val
                20                  25                  30

Ala Pro Met Ala Leu Thr Thr Leu Glu Gly Gly Asn Leu Glu Ala Lys
            35                  40                  45

Val Thr Met His Ile Lys Gly Arg Ser Gln Glu Val Lys Ala Ile Leu
    50                  55                  60

Glu Lys Thr Asp Glu Pro Gly Lys Tyr Thr Ala Ile Gly Gly Ile His
65                  70                  75                  80

Val Ala Arg Ile Ile Gly Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 31
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 31

Ala Ser Asp Glu Glu Ile Gln Asp Val Ser Gly Thr Trp Tyr Leu Lys
1               5                   10                  15

Ala Met Thr Val Asp Pro Gly Ala Leu Arg Cys Leu Ala Gly Ser Val
                20                  25                  30

Thr Pro Met Thr Leu Thr Thr Leu Glu Gly Gly Asn Leu Glu Ala Lys
            35                  40                  45

Val Val Val His Ile Lys Gly Arg Ser Gln Glu Val Arg Ala Val Leu
    50                  55                  60

Gly Lys Thr Asp Glu Pro Gly Lys Tyr Thr Ala Ile Gly Gly Ile His
65                  70                  75                  80

Val Ala Tyr Ile Thr Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 32
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 32

Ala Ser Asp Glu Glu Ile Gln Asp Val Ser Gly Thr Trp Tyr Leu Lys
1               5                   10                  15

Ala Met Thr Val Asp Pro Gly Ala Leu Arg Cys Leu Ala Gly Ser Val
                20                  25                  30

Thr Pro Met Thr Leu Thr Thr Leu Glu Gly Gly Asn Leu Glu Ala Lys
            35                  40                  45

Val Thr Met His Ile Lys Gly Arg Pro Gln Glu Val Lys Ala Val Leu
50                  55                  60

Gly Lys Thr Asp Glu Pro Gly Lys Tyr Thr Ala Ile Gly Gly Ile His
65                  70                  75                  80

Val Ala Tyr Ile Val Arg Ser His Val Lys Asp His Tyr Ile Phe Tyr
                85                  90                  95

Ser Glu Gly Cys Leu Ser Glu Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 33
<211> LENGTH: 152
<212> TYPE: PRT
<213> ORGANISM: Artificial
<220> FEATURE:
<223> OTHER INFORMATION: Mutein of human tear lipocalin with binding
      affinity for VEGF

<400> SEQUENCE: 33

Ala Ser Asp Glu Glu Ile Gln Asp Val Ser Gly Thr Trp Tyr Leu Lys
1               5                   10                  15

Ala Met Thr Val Asp Ser Gly Ala Leu Arg Cys Leu Ala Gly Ser Val
                20                  25                  30

Ile Pro Thr Thr Leu Thr Thr Leu Glu Gly Gly Asn Leu Glu Ala Lys
            35                  40                  45

Val Thr Met His Ile Lys Gly Arg Ser Gln Glu Val Lys Ala Val Leu
50                  55                  60

Glu Lys Thr Asp Glu Pro Gly Lys Tyr Thr Ala Ile Gly Gly Ile His
65                  70                  75                  80

Val Ala His Ile Ile Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 34
<211> LENGTH: 152
<212> TYPE: PRT
<213> ORGANISM: Artificial
<220> FEATURE:
<223> OTHER INFORMATION: Mutein of human tear lipocalin with binding
      affinity for VEGFR2

<400> SEQUENCE: 34

Ala Ser Asp Glu Glu Ile Gln Asp Val Ser Gly Thr Trp Tyr Leu Lys
1               5                   10                  15

Ala Met Thr Val Asp Ser Ile Phe Pro Ser Gly Arg Ile Tyr Ser Val
            20                  25                  30

Thr Pro Met Thr Leu Thr Thr Leu Glu Gly Gly Asn Leu Glu Ala Lys
        35                  40                  45

Val Thr Met Lys Phe Arg Gly Arg Ser Gln Glu Val Lys Ala Val Leu
    50                  55                  60

Glu Lys Thr Asp Glu Pro Gly Lys Tyr Thr Ala Ser Gly Gly Glu His
65                  70                  75                  80

Val Ala Tyr Ile Ile Arg Ser His Val Lys Asp His Tyr Ile Phe Tyr
                85                  90                  95

Ser Glu Gly Leu Ala Val Gly Thr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 35
<211> LENGTH: 152
<212> TYPE: PRT
<213> ORGANISM: Artificial
<220> FEATURE:
<223> OTHER INFORMATION: Mutein of human tear lipocalin with binding
      affinity for VEGFR2

<400> SEQUENCE: 35

Ala Ser Asp Glu Glu Ile Gln Asp Val Ser Gly Thr Trp Tyr Leu Lys
1               5                   10                  15

Ala Met Thr Val Asp Ser Ile Phe Pro Ser Gly Arg Ile Tyr Ser Val
            20                  25                  30

Thr Pro Met Thr Leu Thr Thr Leu Glu Gly Gly Asn Leu Glu Ala Lys
        35                  40                  45

Val Thr Met Glu Phe Arg Gly Arg Ser Gln Glu Val Lys Ala Val Leu
    50                  55                  60

Glu Lys Thr Asp Glu Pro Gly Lys Tyr Thr Ala Ser Gly Gly Glu His
65                  70                  75                  80

Val Ala Tyr Ile Ile Arg Ser His Val Lys Asp His Tyr Ile Phe Tyr
                85                  90                  95

Ser Glu Gly Leu Ala Val Arg Thr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 36
<211> LENGTH: 152
<212> TYPE: PRT
<213> ORGANISM: Artificial
<220> FEATURE:
<223> OTHER INFORMATION: Mutein of human tear lipocalin with binding
      affinity for VEGFR2

<400> SEQUENCE: 36

Ala Ser Asp Glu Glu Ile Gln Asp Val Ser Gly Thr Trp Tyr Leu Lys
1               5                   10                  15

Ala Met Thr Val Asp Ser Ile Phe Pro Ser Gly Arg Ile Tyr Ser Val
            20                  25                  30

Thr Pro Met Thr Leu Thr Thr Leu Glu Gly Gly Asn Leu Glu Ala Lys
        35                  40                  45

Val Thr Met Ala Phe Arg Gly Arg Ser Gln Glu Met Lys Ala Val Leu
    50                  55                  60

Glu Lys Thr Asp Glu Pro Gly Lys Tyr Thr Ala Ser Gly Gly Glu His
65                  70                  75                  80

Val Ala Tyr Ile Ile Arg Ser His Val Lys Asp His Tyr Ile Phe Tyr
                85                  90                  95

Ser Glu Gly Leu Ala Val Gly Thr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 37
<211> LENGTH: 152
<212> TYPE: PRT
<213> ORGANISM: Artificial
<220> FEATURE:
<223> OTHER INFORMATION: Mutein of human tear lipocalin with binding
      affinity for VEGFR2

<400> SEQUENCE: 37

Ala Ser Asp Glu Glu Ile Gln Asp Val Ser Gly Thr Trp Tyr Leu Lys
1               5                   10                  15

Ala Met Thr Val Asp Ser Ile Phe Pro Ser Gly Arg Ile Tyr Ser Val
            20                  25                  30

Thr Pro Met Thr Leu Thr Thr Leu Glu Gly Gly Asn Leu Glu Ala Lys
        35                  40                  45

Val Thr Met Glu Phe Arg Gly Arg Ser Gln Glu Val Lys Ala Val Leu
    50                  55                  60

Glu Lys Thr Gly Glu Pro Gly Lys Tyr Thr Ala Pro Gly Gly Glu His
65                  70                  75                  80

Val Ala Tyr Ile Ile Arg Ser His Val Lys Asp His Tyr Ile Phe Tyr
                85                  90                  95

Ser Glu Gly Leu Ala Val Gly Thr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

-continued

```
<210> SEQ ID NO 38
<211> LENGTH: 152
<212> TYPE: PRT
<213> ORGANISM: Artificial
<220> FEATURE:
<223> OTHER INFORMATION: Mutein of human tear lipocalin with binding
      affinity for VEGFR2

<400> SEQUENCE: 38

Ala Ser Asp Glu Glu Ile Gln Asp Val Ser Gly Thr Trp Tyr Leu Lys
1               5                   10                  15

Ala Met Thr Val Asp Ser Ile Phe Pro Ser Gly Arg Ile Tyr Ser Val
                20                  25                  30

Thr Pro Met Thr Leu Thr Thr Leu Glu Gly Gly Asn Leu Glu Ala Lys
            35                  40                  45

Val Thr Met Glu Phe Arg Gly Arg Ser Gln Glu Val Lys Ala Val Leu
    50                  55                  60

Glu Lys Thr Asp Glu Pro Gly Arg Tyr Thr Ala Ser Gly Gly Glu His
65                  70                  75                  80

Val Ala Tyr Ile Thr Arg Ser His Val Lys Asp His Tyr Ile Phe Tyr
                85                  90                  95

Ser Glu Gly Leu Ala Val Lys Thr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 39
<211> LENGTH: 152
<212> TYPE: PRT
<213> ORGANISM: Artificial
<220> FEATURE:
<223> OTHER INFORMATION: Mutein of human tear lipocalin with binding
      affinity for VEGFR2

<400> SEQUENCE: 39

Ala Ser Asp Glu Glu Ile Gln Asp Val Ser Gly Thr Trp Tyr Leu Lys
1               5                   10                  15

Ala Met Thr Val Asp Ser Ile Phe Pro Ser Gly Arg Ile Tyr Ser Val
                20                  25                  30

Thr Pro Met Thr Leu Thr Thr Leu Glu Gly Gly Asn Leu Glu Ala Lys
            35                  40                  45

Val Thr Met Glu Phe Arg Gly Arg Ser Gln Lys Val Lys Ala Val Leu
    50                  55                  60

Glu Lys Thr Asp Glu Pro Gly Lys Tyr Thr Ala Ser Gly Gly Glu His
65                  70                  75                  80

Val Ala Tyr Ile Ile Lys Ser His Val Lys Asp His Tyr Ile Phe Tyr
                85                  90                  95

Ser Glu Gly Leu Ala Val Glu Thr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 40
<211> LENGTH: 40
<212> TYPE: DNA
<213> ORGANISM: Artificial
<220> FEATURE:
<223> OTHER INFORMATION: Oligonucleotide primer TL 107
<220> FEATURE:
<221> NAME/KEY: misc_feature
<222> LOCATION: (20)..(21)
<223> OTHER INFORMATION: n is a, c, g, or t

<400> SEQUENCE: 40
gaaggccatg acggtggacn nsggcgcgct gaggtgcctc                            40

<210> SEQ ID NO 41
<211> LENGTH: 52
<212> TYPE: DNA
<213> ORGANISM: Artificial
<220> FEATURE:
<223> OTHER INFORMATION: Oligonucleotide primer TL 109
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 41
ggccatcggg ggcatccacg tggcannsat cnnsaggtcg cacgtgaagg ac              52

<210> SEQ ID NO 42
<211> LENGTH: 40
<212> TYPE: DNA
<213> ORGANISM: Artificial
<220> FEATURE:
<223> OTHER INFORMATION: Oligonucleotide primer TL 110
<220> FEATURE:
<221> NAME/KEY: misc_feature
<222> LOCATION: (23)..(24)
<223> OTHER INFORMATION: n is a, c, g, or t

<400> SEQUENCE: 42
cacccctggg accgggaccc csnncaagca gccctcagag                            40

<210> SEQ ID NO 43
<211> LENGTH: 59
<212> TYPE: DNA
<213> ORGANISM: Artificial
<220> FEATURE:
<223> OTHER INFORMATION: Oligonucleotide primer TL 111
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 43
cccccgatgg ccgtgtasnn ccccggctca tcagttttsn ncaggacggc cctcacctc       59

<210> SEQ ID NO 44
<211> LENGTH: 152
<212> TYPE: PRT
<213> ORGANISM: Artificial
<220> FEATURE:
<223> OTHER INFORMATION: S236.1-A22
```

<400> SEQUENCE: 44

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30

Ile Pro Thr Thr Leu Thr Thr Leu Glu Gly Gly Asn Leu Glu Ala Lys
            35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 45
<211> LENGTH: 152
<212> TYPE: PRT
<213> ORGANISM: Artificial
<220> FEATURE:
<223> OTHER INFORMATION: S236.1-J20

<400> SEQUENCE: 45

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30

Ile Pro Thr Thr Leu Thr Thr Leu Glu Gly Gly Asn Leu Glu Ala Lys
            35                  40                  45

Val Thr Met His Ile Lys Gly Arg Pro Gln Glu Val Lys Ala Val Leu
    50                  55                  60

Thr Lys Thr Asp Glu Pro Gly Ala Tyr Thr Ala Ile Gly Gly Ile His
65                  70                  75                  80

Val Ala Gln Ile His Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 46
<211> LENGTH: 152
<212> TYPE: PRT
<213> ORGANISM: Artificial
<220> FEATURE:
<223> OTHER INFORMATION: S236.1-M11

```
<400> SEQUENCE: 46

Ala Ser Asp Glu Glu Ile Gln Asp Val Ser Gly Thr Trp Tyr Leu Lys
1               5                   10                  15

Ala Met Thr Val Asp Leu Gly Ala Leu Arg Cys Leu Ala Gly Ser Val
            20                  25                  30

Ile Pro Thr Ser Leu Thr Thr Leu Glu Gly Gly Asp Leu Glu Ala Lys
        35                  40                  45

Val Thr Met His Ile Lys Gly Arg Ser Gln Glu Val Lys Ala Val Leu
    50                  55                  60

Ser Lys Thr Asp Glu Pro Gly Met Tyr Thr Ala Ile Gly Gly Ile His
65                  70                  75                  80

Val Ala Arg Ile Met Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 47
<211> LENGTH: 152
<212> TYPE: PRT
<213> ORGANISM: Artificial
<220> FEATURE:
<223> OTHER INFORMATION: S236.1-L03

<400> SEQUENCE: 47

Ala Ser Asp Glu Glu Ile Gln Asp Val Ser Gly Thr Trp Tyr Leu Lys
1               5                   10                  15

Ala Met Thr Val Asp Ile Gly Ala Leu Arg Cys Leu Ala Gly Ser Val
            20                  25                  30

Thr Pro Met Thr Leu Thr Thr Leu Glu Gly Gly Asn Leu Glu Ala Lys
        35                  40                  45

Val Val Val His Ile Lys Gly Arg Ser Gln Glu Val Arg Ala Val Leu
    50                  55                  60

Ser Lys Thr Asp Glu Pro Gly Pro Tyr Thr Ala Ile Gly Gly Ile His
65                  70                  75                  80

Val Ala Lys Ile Lys Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 48
<211> LENGTH: 745
<212> TYPE: DNA
<213> ORGANISM: Artificial
<220> FEATURE:
<223> OTHER INFORMATION: pTLPC51 118-862 XbaI/HindIII nt
```

<400> SEQUENCE: 48

```
tctagataac gagggcaaaa aatgaaaaag acagctatcg cgattgcagt ggcactggct      60
ggtttcgcta ccgtagcgca ggccgcctca gacgaggaga ttcaggatgt gtcaggacg     120
tggtatctga aggccatgac ggtggacagg gagttccctg agatgaatct ggaatcggtg    180
acacccatga ccctcacgac cctggaaggg gcaacctgg aagccaaggt caccatgctg     240
ataagtggcc ggagccagga ggtgaaggcc gtcctggaga aaactgacga gccgggaaaa    300
tacacggccg acgggggcaa gcacgtggca tacatcatca ggtcgcacgt gaaggaccac    360
tacatctttt actctgaggg cgagctccac gggaagccgg tcccagggt gtggctcgtg     420
ggcagagacc ccaagaacaa cctggaagcc ttggaggact ttgagaaagc cgcaggagcc    480
cgcggactca gcacggagag catcctcatc cccaggcaga gcgaaaccag ctctccaggg    540
agcgctggtg ccgtcgacgc taactctctg gctgaagcta agttctggc taaccgtgaa     600
ctggacaaat acggtgtttc cgactactac aaaaacctca tcaacaacgc taaaaccgtt    660
gaaggtgtta agctctgat cgacgaaatt ctcgcagcac tgccgagcgc ttggtctcac     720
ccgcagttcg aaaaataata agctt                                          745
```

<210> SEQ ID NO 49
<211> LENGTH: 238
<212> TYPE: PRT
<213> ORGANISM: Artificial
<220> FEATURE:
<223> OTHER INFORMATION: Fusion protein OmpA signal sequence - human tear lipocalin - albumin-binding domain (abd) - Strep-Tag II

<400> SEQUENCE: 49

```
Met Lys Lys Thr Ala Ile Ala Ile Ala Val Ala Leu Ala Gly Phe Ala
1               5                  10                  15

Thr Val Ala Gln Ala Ala Ser Asp Glu Glu Ile Gln Asp Val Ser Gly
            20                  25                  30

Thr Trp Tyr Leu Lys Ala Met Thr Val Asp Arg Glu Phe Pro Glu Met
        35                  40                  45

Asn Leu Glu Ser Val Thr Pro Met Thr Leu Thr Thr Leu Glu Gly Gly
    50                  55                  60

Asn Leu Glu Ala Lys Val Thr Met Leu Ile Ser Gly Arg Ser Gln Glu
65                  70                  75                  80

Val Lys Ala Val Leu Glu Lys Thr Asp Glu Pro Gly Lys Tyr Thr Ala
                85                  90                  95

Asp Gly Gly Lys His Val Ala Tyr Ile Ile Arg Ser His Val Lys Asp
            100                 105                 110

His Tyr Ile Phe Tyr Ser Glu Gly Glu Leu His Gly Lys Pro Val Pro
        115                 120                 125

Gly Val Trp Leu Val Gly Arg Asp Pro Lys Asn Asn Leu Glu Ala Leu
    130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Ser Ser Pro Gly Ser Ala Gly
                165                 170                 175

Ala Val Asp Ala Asn Ser Leu Ala Glu Ala Lys Val Leu Ala Asn Arg
            180                 185                 190

Glu Leu Asp Lys Tyr Gly Val Ser Asp Tyr Tyr Lys Asn Leu Ile Asn
        195                 200                 205
```

-continued

```
Asn Ala Lys Thr Val Glu Gly Val Lys Ala Leu Ile Asp Glu Ile Leu
    210                 215                 220

Ala Ala Leu Pro Ser Ala Trp Ser His Pro Gln Phe Glu Lys
225                 230                 235
```

<210> SEQ ID NO 50
<211> LENGTH: 745
<212> TYPE: DNA
<213> ORGANISM: Artificial
<220> FEATURE:
<223> OTHER INFORMATION: pTLPC51_S236.1-A22 118-862 XbaI/HindIII (nt
      sequence encoding a fusion protein of ompA, human tear lipocalin
      mutein S236.1-A22, abd and Strep-Tag II)

<400> SEQUENCE: 50

```
tctagataac gagggcaaaa aatgaaaaag acagctatcg cgattgcagt ggcactggct    60
ggtttcgcta ccgtagcgca ggccgcctca gacgaggaga ttcaggatgt gtcaggacg   120
tggtatctga aggccatgac ggtggacgtg ggcgcgctga ggtgcctcgc ggggtcggtg   180
atacccacga ccctcacgac cctggaaggg ggcaacctgg aagccaaggt caccatgcat   240
atcaagggcc ggtcccagga ggtgaaggcc gtcctgagca aaactgatga gccggggatc   300
tacacggcca tcgggggcat ccacgtggca agatcgggga ggtcgcacgt gaaggaccac   360
tacatctttt actctgaggg ctgcttgagc ggggtcccgg tcccaggggt gtggctcgtg   420
ggcagagacc ccaagaacaa cctggaagcc ttggaggact tgagaaagc cgcaggagcc   480
cgcggactca gcacggagag catcctcatc cccaggcaga gcgaaaccag ctctccaggg   540
agcgctggtg ccgtcgacgc taactctctg gctgaagcta agttctggc taaccgtgaa   600
ctggacaaat acggtgtttc cgactactac aaaaaccctca tcaacaacgc taaaaccgtt   660
gaaggtgtta agctctgat cgacgaaatt ctcgcagcac tgccgagcgc ttggtctcac   720
ccgcagttcg aaaaataata agctt                                          745
```

<210> SEQ ID NO 51
<211> LENGTH: 238
<212> TYPE: PRT
<213> ORGANISM: Artificial
<220> FEATURE:
<223> OTHER INFORMATION: Fusion protein of ompA, human tear lipocalin
      mutein S236.1-A22, albumin-binding domain (abd) and Strep-Tag II

<400> SEQUENCE: 51

```
Met Lys Lys Thr Ala Ile Ala Ile Ala Val Ala Leu Ala Gly Phe Ala
1               5                  10                  15

Thr Val Ala Gln Ala Ala Ser Asp Glu Glu Ile Gln Asp Val Ser Gly
            20                  25                  30

Thr Trp Tyr Leu Lys Ala Met Thr Val Asp Val Gly Ala Leu Arg Cys
        35                  40                  45

Leu Ala Gly Ser Val Ile Pro Thr Thr Leu Thr Thr Leu Glu Gly Gly
    50                  55                  60

Asn Leu Glu Ala Lys Val Thr Met His Ile Lys Gly Arg Ser Gln Glu
65                  70                  75                  80

Val Lys Ala Val Leu Ser Lys Thr Asp Glu Pro Gly Ile Tyr Thr Ala
                85                  90                  95

Ile Gly Gly Ile His Val Ala Lys Ile Gly Arg Ser His Val Lys Asp
            100                 105                 110

His Tyr Ile Phe Tyr Ser Glu Gly Cys Leu Ser Gly Val Pro Val Pro
        115                 120                 125
```

```
Gly Val Trp Leu Val Gly Arg Asp Pro Lys Asn Asn Leu Glu Ala Leu
            130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Ser Pro Gly Ser Ala Gly
                165                 170                 175

Ala Val Asp Ala Asn Ser Leu Ala Glu Ala Lys Val Leu Ala Asn Arg
            180                 185                 190

Glu Leu Asp Lys Tyr Gly Val Ser Asp Tyr Tyr Lys Asn Leu Ile Asn
            195                 200                 205

Asn Ala Lys Thr Val Gly Val Lys Ala Leu Ile Asp Glu Ile Leu
            210                 215                 220

Ala Ala Leu Pro Ser Ala Trp Ser His Pro Gln Phe Glu Lys
225                 230                 235

<210> SEQ ID NO 52
<211> LENGTH: 162
<212> TYPE: PRT
<213> ORGANISM: Artificial
<220> FEATURE:
<223> OTHER INFORMATION: S236.1-A22-strep

<400> SEQUENCE: 52

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30

Ile Pro Thr Thr Leu Thr Thr Leu Glu Gly Gly Asn Leu Glu Ala Lys
            35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala Trp Ser His Pro Gln Phe
145                 150                 155                 160

Glu Lys

<210> SEQ ID NO 53
<211> LENGTH: 162
<212> TYPE: PRT
<213> ORGANISM: Artificial
<220> FEATURE:
<223> OTHER INFORMATION: S236.1-J20-strep

<400> SEQUENCE: 53

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30
```

```
Ile Pro Thr Thr Leu Thr Thr Leu Glu Gly Gly Asn Leu Glu Ala Lys
            35                  40                  45

Val Thr Met His Ile Lys Gly Arg Pro Gln Glu Val Lys Ala Val Leu
         50                  55                  60

Thr Lys Thr Asp Glu Pro Gly Ala Tyr Thr Ala Ile Gly Gly Ile His
 65                  70                  75                  80

Val Ala Gln Ile His Arg Ser His Val Lys Asp His Tyr Ile Phe Tyr
                 85                  90                  95

Ser Glu Gly Cys Leu Ser Gly Val Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Ser Ala Trp Ser His Pro Gln Phe
145                 150                 155                 160

Glu Lys

<210> SEQ ID NO 54
<211> LENGTH: 162
<212> TYPE: PRT
<213> ORGANISM: Artificial
<220> FEATURE:
<223> OTHER INFORMATION: S236.1-M11-strep

<400> SEQUENCE: 54

Ala Ser Asp Glu Glu Ile Gln Asp Val Ser Gly Thr Trp Tyr Leu Lys
 1               5                  10                  15

Ala Met Thr Val Asp Leu Gly Ala Leu Arg Cys Leu Ala Gly Ser Val
             20                  25                  30

Ile Pro Thr Ser Leu Thr Thr Leu Glu Gly Gly Asp Leu Glu Ala Lys
            35                  40                  45

Val Thr Met His Ile Lys Gly Arg Ser Gln Glu Val Lys Ala Val Leu
         50                  55                  60

Ser Lys Thr Asp Glu Pro Gly Met Tyr Thr Ala Ile Gly Gly Ile His
 65                  70                  75                  80

Val Ala Arg Ile Met Arg Ser His Val Lys Asp His Tyr Ile Phe Tyr
                 85                  90                  95

Ser Glu Gly Cys Leu Ser Gly Val Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Ser Ala Trp Ser His Pro Gln Phe
145                 150                 155                 160

Glu Lys

<210> SEQ ID NO 55
<211> LENGTH: 162
<212> TYPE: PRT
<213> ORGANISM: Artificial
<220> FEATURE:
<223> OTHER INFORMATION: S236.1-L03
```

```
<400> SEQUENCE: 55

Ala Ser Asp Glu Glu Ile Gln Asp Val Ser Gly Thr Trp Tyr Leu Lys
1               5                   10                  15

Ala Met Thr Val Asp Ile Gly Ala Leu Arg Cys Leu Ala Gly Ser Val
            20                  25                  30

Thr Pro Met Thr Leu Thr Thr Leu Glu Gly Gly Asn Leu Glu Ala Lys
        35                  40                  45

Val Val Val His Ile Lys Gly Arg Ser Gln Glu Val Arg Ala Val Leu
    50                  55                  60

Ser Lys Thr Asp Glu Pro Gly Pro Tyr Thr Ala Ile Gly Gly Ile His
65                  70                  75                  80

Val Ala Lys Ile Lys Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
130                 135                 140

Gln Ser Glu Thr Ser Ser Pro Gly Ser Ala Trp Ser His Pro Gln Phe
145                 150                 155                 160

Glu Lys

<210> SEQ ID NO 56
<211> LENGTH: 41
<212> TYPE: DNA
<213> ORGANISM: Artificial
<220> FEATURE:
<223> OTHER INFORMATION: Oligonucleotide primer A22_D95C forward

<400> SEQUENCE: 56
gaggtcgcac gtgaagtgcc actacatctt ttactctgag g                41

<210> SEQ ID NO 57
<211> LENGTH: 41
<212> TYPE: DNA
<213> ORGANISM: Artificial
<220> FEATURE:
<223> OTHER INFORMATION: Oligonucleotide primer A22_D95C reverse

<400> SEQUENCE: 57
cctcagagta aaagatgtag tggcacttca cgtgcgacct c                41

<210> SEQ ID NO 58
<211> LENGTH: 39
<212> TYPE: DNA
<213> ORGANISM: Artificial
<220> FEATURE:
<223> OTHER INFORMATION: Oligonucleotide primer A22_T40C forward

<400> SEQUENCE: 58
gggtcggtga tacccacgtg cctcacgacc ctggaaggg                   39

<210> SEQ ID NO 59
<211> LENGTH: 39
<212> TYPE: DNA
<213> ORGANISM: Artificial
<220> FEATURE:
<223> OTHER INFORMATION: Oligonucleotide primer A22_T40C reverse
```

<400> SEQUENCE: 59
cccttccagg gtcgtgaggc acgtgggtat caccgaccc                                39

<210> SEQ ID NO 60
<211> LENGTH: 39
<212> TYPE: DNA
<213> ORGANISM: Artificial
<220> FEATURE:
<223> OTHER INFORMATION: Oligonucleotide primer A22_E73C forward

<400> SEQUENCE: 60
ccgtcctgag caaaactgat gcccgggga tctacacgg                                 39

<210> SEQ ID NO 61
<211> LENGTH: 39
<212> TYPE: DNA
<213> ORGANISM: Artificial
<220> FEATURE:
<223> OTHER INFORMATION: Oligonucleotide primer A22_E73C reverse

<400> SEQUENCE: 61
ccgtgtagat ccccgggcaa tcagttttgc tcaggacgg                                39

<210> SEQ ID NO 62
<211> LENGTH: 31
<212> TYPE: DNA
<213> ORGANISM: Artificial
<220> FEATURE:
<223> OTHER INFORMATION: Oligonucleotide primer A22_E131C forward

<400> SEQUENCE: 62
gccttggagg acttttgtaa agccgcagga g                                        31

<210> SEQ ID NO 63
<211> LENGTH: 31
<212> TYPE: DNA
<213> ORGANISM: Artificial
<220> FEATURE:
<223> OTHER INFORMATION: Oligonucleotide primer A22_E131C reverse

<400> SEQUENCE: 63
ctcctgcggc tttacaaaag tcctccaagg c                                        31

<210> SEQ ID NO 64
<211> LENGTH: 35
<212> TYPE: DNA
<213> ORGANISM: Artificial
<220> FEATURE:
<223> OTHER INFORMATION: Oligonucleotide primer A22_R90C forward

<400> SEQUENCE: 64
cgtggcaaag atcgggtgct cgcacgtgaa ggacc                                    35

<210> SEQ ID NO 65
<211> LENGTH: 35
<212> TYPE: DNA
<213> ORGANISM: Artificial
<220> FEATURE:
<223> OTHER INFORMATION: Oligonucleotide primer A22_R90C reverse

<400> SEQUENCE: 65
ggtccttcac gtgcgagcac ccgatctttg ccacg                                    35

```
<210> SEQ ID NO 66
<211> LENGTH: 154
<212> TYPE: PRT
<213> ORGANISM: Artificial
<220> FEATURE:
<223> OTHER INFORMATION: S236.1-A22 Thr 40-Cys

<400> SEQUENCE: 66

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30

Ile Pro Thr Cys Leu Thr Thr Leu Glu Gly Gly Asn Leu Glu Ala Lys
            35                  40                  45

Val Thr Met His Ile Lys Gly Arg Ser Gln Glu Val Lys Ala Val Leu
        50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150

<210> SEQ ID NO 67
<211> LENGTH: 154
<212> TYPE: PRT
<213> ORGANISM: Artificial
<220> FEATURE:
<223> OTHER INFORMATION: S236.1-A22 Glu73-Cys

<400> SEQUENCE: 67

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30

Ile Pro Thr Thr Leu Thr Thr Leu Glu Gly Gly Asn Leu Glu Ala Lys
            35                  40                  45

Val Thr Met His Ile Lys Gly Arg Ser Gln Glu Val Lys Ala Val Leu
        50                  55                  60

Ser Lys Thr Asp Cys Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150
```

<210> SEQ ID NO 68
<211> LENGTH: 154
<212> TYPE: PRT
<213> ORGANISM: Artificial
<220> FEATURE:
<223> OTHER INFORMATION: S236.1-A22 Asp95-Cys

<400> SEQUENCE: 68

```
Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
            20                  25                  30

Ile Pro Thr Thr Leu Thr Thr Leu Glu Gly Gly Asn Leu Glu Ala Lys
        35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Cys His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150
```

<210> SEQ ID NO 69
<211> LENGTH: 154
<212> TYPE: PRT
<213> ORGANISM: Artificial
<220> FEATURE:
<223> OTHER INFORMATION: S236.1-A22 Arg90-Cys

<400> SEQUENCE: 69

```
Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
            20                  25                  30

Ile Pro Thr Thr Leu Thr Thr Leu Glu Gly Gly Asn Leu Glu Ala Lys
        35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Cys Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150
```

```
<210> SEQ ID NO 70
<211> LENGTH: 154
<212> TYPE: PRT
<213> ORGANISM: Artificial
<220> FEATURE:
<223> OTHER INFORMATION: S236.1-A22 Glu131-Cys

<400> SEQUENCE: 70

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
                20                  25                  30

Ile Pro Thr Thr Leu Thr Thr Leu Glu Gly Gly Asn Leu Glu Ala Lys
            35                  40                  45

Val Thr Met His Ile Lys Gly Arg Ser Gln Glu Val Lys Ala Val Leu
        50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Cys Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150

<210> SEQ ID NO 71
<211> LENGTH: 158
<212> TYPE: PRT
<213> ORGANISM: Homo sapiens
<220> FEATURE:
<223> OTHER INFORMATION: mature human tear lipocalin

<400> SEQUENCE: 71

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
                20                  25                  30

Leu Glu Ser Val Thr Pro Met Thr Leu Thr Thr Leu Glu Gly Gly Asn
            35                  40                  45

Leu Glu Ala Lys Val Thr Met Leu Ile Ser Gly Arg Cys Gln Glu Val
        50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```